(12) United States Patent
Tsiperman et al.

(10) Patent No.: US 8,198,469 B2
(45) Date of Patent: Jun. 12, 2012

(54) CRYSTALLINE FORMS OF TIGECYCLINE AND PROCESSES FOR PREPARATION THEREOF

(75) Inventors: Evgeny Tsiperman, Be'er-Sheva (IL); Sofia Gorohovsky-Rosenberg, Beer Sheva (IL); Slavik Yurkovski, Kiryat Gat (IL); Sergei Fine, Qiriat-Arbaa (IL); Tamás Koltai, Netanya (IL); Sigalit Levi, Modi'in (IL); Leonid Metsger, Beer-Sheva (IL); Michal Rafilovich, Petach-Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1220 days.

(21) Appl. No.: 11/998,878

(22) Filed: Nov. 29, 2007

(65) Prior Publication Data

US 2009/0005453 A1    Jan. 1, 2009

Related U.S. Application Data

(60) Provisional application No. 60/861,625, filed on Nov. 29, 2006, provisional application No. 60/874,831, filed on Dec. 14, 2006, provisional application No. 60/879,475, filed on Jan. 9, 2007, provisional application No. 60/900,807, filed on Feb. 12, 2007, provisional application No. 60/904,913, filed on Mar. 5, 2007, provisional application No. 60/920,645, filed on Mar. 28, 2007, provisional application No. 60/927,959, filed on May 7, 2007, provisional application No. 60/930,136, filed on May 14, 2007, provisional application No. 60/959,389, filed on Jul. 13, 2007.

(51) Int. Cl.
| | |
|---|---|
| *C07C 43/00* | (2006.01) |
| *C07C 49/00* | (2006.01) |
| *C07C 233/01* | (2006.01) |
| *A61K 31/65* | (2006.01) |
| *A61K 31/167* | (2006.01) |
| *A61P 31/04* | (2006.01) |

(52) U.S. Cl. ......... 552/205; 514/152; 514/616; 564/157
(58) Field of Classification Search .................. 514/152, 514/616; 564/157; 552/205
See application file for complete search history.

(56) References Cited

U.S. PATENT DOCUMENTS

| | | | |
|---|---|---|---|
| 2,997,471 | A | 8/1961 | Cheney et al. |
| 4,024,272 | A | 5/1977 | Rogalski et al. |
| 5,284,963 | A | 2/1994 | Sum et al. |
| 5,401,863 | A | 3/1995 | Hlavka et al. |
| 5,494,903 | A | 2/1996 | Hlavka et al. |
| 5,495,031 | A | 2/1996 | Sum et al. |
| 5,675,030 | A | 10/1997 | Krishanan et al. |
| 2006/0183720 | A1 | 8/2006 | Sum et al. |
| 2007/0026080 | A1 | 2/2007 | Chanana et al. |
| 2007/0049560 | A1 | 3/2007 | Krishnan et al. |
| 2007/0049561 | A1 | 3/2007 | Krishnan et al. |
| 2007/0049562 | A1 | 3/2007 | Krishnan et al. |
| 2007/0049563 | A1 | 3/2007 | Krishnan et al. |
| 2007/0123497 | A1 | 5/2007 | Krishnan et al. |

FOREIGN PATENT DOCUMENTS

| | | |
|---|---|---|
| EP | 0 535 346 | 4/1993 |
| JP | 01-029346 | 1/1989 |
| WO | WO 02/072031 | 9/2002 |
| WO | WO 2006/128150 | 11/2006 |
| WO | WO 2006/130431 | 12/2006 |
| WO | WO 2006/130501 | 12/2006 |
| WO | WO 2007/127292 | 11/2007 |
| WO | WO 2008/155405 | 12/2008 |

OTHER PUBLICATIONS

R.E. Bleil. Organic Chemistry Lab Manual. Dakota State University (2005). Accessed on Jun. 28, 2011 at http://www.homepages.dsu.edu/bleilr/nporg.pdf.*
Measuring colour, 3rd Ed. / R.W.G. Hunt (1998).
Polymorphism in Pharmaceutical Solids, Drugs and the Pharmaceutical Sciences, vol. 95, 1999.
Anonymous, "Tygacil Scientific Discussion", EMEA 2006 http://www.infectiologie.com/site/medias/enseignment/du-lyon/Tygacil%20EPAR.pdf.
Databuse WPI Week 198910. Derwent Publications Ltd., London, GB: An 1989-074689, JP01029346A (Nippon Kayaku KK) Jan. 31, 1989 (Abstract).
J.Med.Chem 37: 184 (1994).
Nelson et al., "Versatile and Facile Synthesis of Diverse Semisynthetic Tetracycline Deriviatives vía Pd-Catalized Reactions", Journal of Organic Chemistry, 68: 5838-5851 (2003).
Sum et al., "Synthesis and Structure—Activity Relationship of Novel Glycylcycline Derivatives Leading to the DIscovery of GAR-936," *Biorganic & Medicinal Chemistry Letters*, 9: 1459-1462 (1999).
March's Advanced Organic Chemistry: Reactions, Mechanisms, and Structure; 5th Ed., 2001.

* cited by examiner

*Primary Examiner* — Barbara P Badio
*Assistant Examiner* — Sara E Townsley
(74) *Attorney, Agent, or Firm* — Kenyon & Kenyon LLP

(57) ABSTRACT

The present invention provides crystalline forms of Tigecycline, and methods of for preparation of crystalline forms and amorphous.

12 Claims, 47 Drawing Sheets

FIG. 37 A solid-state 13C NMR spectrum in the range of 90 to 210ppm for Tigecycline Form XI A solid-state 13C NMR spectrum in the range of 90 to 210ppm for Tigecycline Form XVIII 95.414
109.346
116.540
119.240
126.041
132.883
142.812
148.352
171.331
173.471
174.980
191.837
192.503
196.525

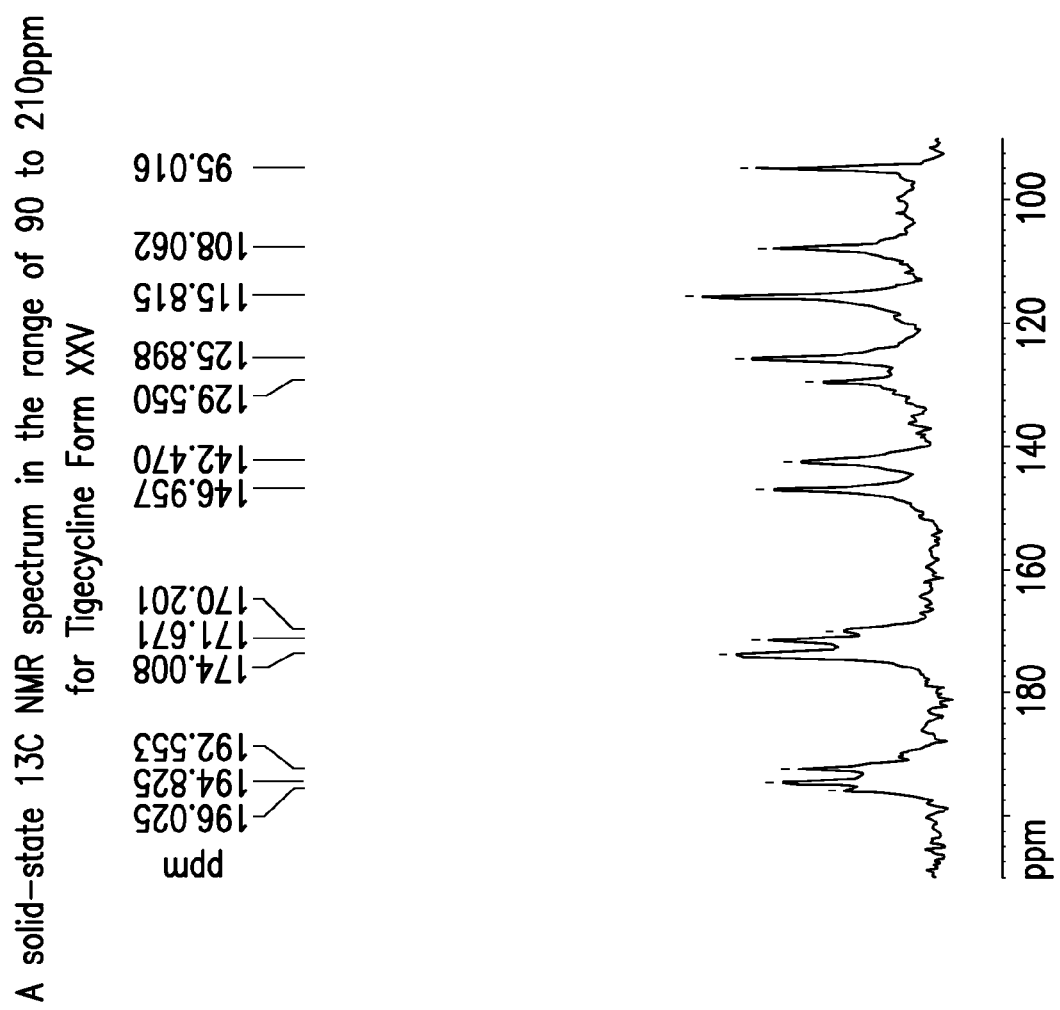

CRYSTALLINE FORMS OF TIGECYCLINE AND PROCESSES FOR PREPARATION THEREOF

CROSS-REFERENCE TO RELATED APPLICATIONS

This application claims the benefit of U.S. Provisional Application Nos. 60/861,625, filed Nov. 29, 2006; 60/874,831, filed Dec. 14, 2006; 60/879,475, filed Jan. 9, 2007; 60/900,807, filed Feb. 12, 2007; 60/904,913, filed Mar. 5, 2007; 60/920,645, filed Mar. 28, 2007; 60/927,959, filed May 7, 2007; 60/930,136, filed May 14, 2007; 60/959,389, filed Jul. 13, 2007. The contents of which are incorporated herein by reference.

FIELD OF THE INVENTION

The present invention relates to the solid state chemistry of Tigecycline.

BACKGROUND OF THE INVENTION

Tigecycline (CAS 220620-09-7), (4S,4aS,5aR,12aS)-9-(2-(tert-butylamino) acetamido)-4,7-bis(dimethylamino)-1,4,4a,5,5a,6,11,12a-octahydro-3,10,12,12a-tetrahydroxy-1,11-dioxo-2-naphthacenecarboxamide, is the first drug of a new generation of tetracycline antibiotics called glycylcyclines. Tigecycline has a wider range of bioactivity than the parent tetracycline and its analogues discovered so far, and it may be administrated less frequently and/or in lower doses.

Tigecycline has been introduced and marketed by Wyeth under the brand name TYGACIL® and it is especially indicated against acute lethal infections caused by Gram-negative bacteria. TYGACIL® is marketed as lyophilized powder or cake for intravenous injection and the drug substance does not contain excipients or preservatives.

Tigecycline has the following structure:

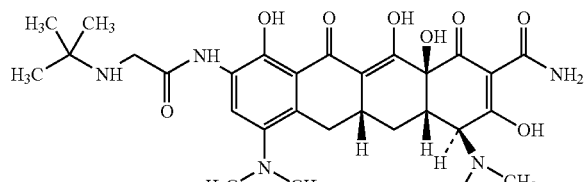

Tigecycline: $C_{29}H_{39}N_5O_8$
MW: 585.65 g/mol and was disclosed in U.S. Pat. Nos. 5,494,903 and 5,284,963. Tigecycline is typically orange in color, having a G:R ratio of more than 1.8.

U.S. Pat. No. 5,675,030 describes a specific method for obtaining solid Tigecycline by evaporation from a dichloromethane solution. The Tigecycline obtained from this method is amorphous. United States Publication No. 2007/0123497 describes crystalline forms of Tigecycline.

WO 2007/127292, herein referred to as WO'292, describes crystalline Forms I and II of Tigecycline.

According to WO '292, Form I of Tigecycline may be prepared by maintaining Tigecycline in a solvent selected from a group consisting of saturated or aromatic $C_5$-$C_8$ hydrocarbons, a low boiling point ketone, and a low boiling point ester.

The present invention relates to the solid state physical properties of Tigecycline. These properties can be influenced by controlling the conditions under which Tigecycline is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must necessitate the use of glidants such as colloidal silicon dioxide, talc, starch, or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulation syrups, elixirs, and other liquid medicaments. The solid state form of a compound can also affect its behavior on compaction and its storage stability.

These practical physical characteristics are influenced by the conformation and orientation of molecules in the unit cell, which define a particular polymorphic form of a substance. The polymorphic form can give rise to thermal behavior different from that of the amorphous material or another polymorphic form. Thermal behavior is measured in the laboratory by such techniques as capillary melting point, thermogravimetric analysis ("TGA"), and differential scanning calorimetry ("DSC") and can be used to distinguish some polymorphic forms from others. A particular polymorphic form can also give rise to distinct spectroscopic properties that can be detectable by powder x-ray crystallography, solid state $^{13}$C NMR spectrometry, and infrared spectrometry.

Generally, the crystalline solid has improved chemical and physical stability over the amorphous form, and forms with low crystallinity. They can also exhibit improved hygroscopicity, bulk properties, and/or flowability.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for crystalline Tigecycline and polymorphic forms thereof.

SUMMARY OF THE INVENTION

The present invention provides crystalline Tigecycline.

The present invention provides yet another crystalline form of Tigecycline, designated Form VI, characterized by a powder XRD pattern with peaks at about 4.6, 8.8, 13.3 and 16.2±0.2 degrees two-theta and optionally a peak at about 7.7±0.2 degrees two-theta. Tigecycline Form VI may be further characterized by data selected from the group consisting of: a powder XRD pattern with one or more peaks selected from the list consisting of about 18.2, 20.2 and 21.4±0.2 degrees two-theta; a powder XRD pattern substantially as depicted in FIG. 4; a solid-state 13C NMR spectrum with signals at about 194.7, 174.6, 141.9, 108.2, and 98.9±0.2 ppm; a solid-state 13C NMR spectrum having chemical shift differences between the signal exhibiting the lowest chemical shift and another in the chemical shift range of 90 to 210 ppm of about 95.8, 75.7, 43.0 and 9.3±0.1 ppm; a solid-state 13C NMR spectrum substantially as depicted in FIG. 28; and a solid-state 13C NMR spectrum depicted in FIG. 29. The signal exhibiting the lowest chemical shift in the chemical shift range of 90 to 210 ppm is, typically, at about 98.9±0.2 ppm.

The present invention provides yet another crystalline form of Tigecycline, designated Form VIII, characterized by data selected from the list consisting of: a powder XRD pattern with peaks at about 4.1, 9.1, 13.8 and 16.0±0.2 degrees two-theta; a powder XRD pattern with peaks at about 4.1, 8.2, 9.1, 13.8 and 16.0±0.2 degrees two-theta.; a powder XRD pattern substantially as depicted in FIG. 6; a solid-state 13C NMR spectrum with signals at about 195.0, 147.5, 142.1, 127.9, and 126.5±0.2 ppm; a solid-state 13C NMR spectrum having chemical shift differences between the signal exhibiting the lowest chemical shift and another in the chemical shift range of 90 to 210 ppm of about 100.2, 52.7, 47.3, 33.1, and 31.7±0.1 ppm; a solid-state 13C NMR spectrum depicted in FIG. 30; and a solid-state 13C NMR spectrum depicted in FIG. 31. The signal exhibiting the lowest chemical shift in the chemical shift range of 90 to 210 ppm is, typically, at about 94.8±1 ppm.

The present invention provides yet another crystalline form of Tigecycline, designated Form IX, characterized by data selected from the group consisting of a powder XRD pattern with peaks at about 5.2, 9.3, 13.1, 13.8 and 16.5±0.2 degrees two-theta; a powder XRD pattern substantially as depicted in FIG. 7; a solid-state 13C NMR spectrum with signals at about 204.4, 192.8, 177.2, 174.7, and 169.5±0.2 ppm; a solid-state 13C NMR spectrum having chemical shift differences between the signal exhibiting the lowest chemical shift and another in the chemical shift range of 90 to 210 ppm of about 108.6, 97.0, 81.4, 78.9, and 73.7±0.1 ppm; a solid-state 13C NMR spectrum depicted in FIG. 32; and a solid-state 13C NMR spectrum depicted in FIG. 33. The signal exhibiting the lowest chemical shift in the chemical shift range of 90 to 210 ppm is, typically, at about 95.8±1 ppm.

The present invention provides yet another crystalline form of Tigecycline, designated Form X, characterized by data selected from the group consisting of a powder XRD pattern with peaks at about 4.6, 9.4, 14.4, 15.5 and 16.5±0.2 degrees two-theta; a powder XRD pattern with peaks at about 4.6, 9.4, 10.7, 14.4, 15.5 and 16.5±0.2 degrees two-theta.; a powder XRD pattern substantially as depicted in FIG. 8; a solid-state 13C NMR spectrum with signals at about 194.2, 192.1, 147.9, 142.9, 125.8, and 116.0±0.2 ppm; a solid-state 13C NMR spectrum having chemical shift differences between the signal exhibiting the lowest chemical shift and another in the chemical shift range of 90 to 210 ppm of about 99.0, 96.9, 52.7, 47.7, and 30.6±0.1 ppm; a solid-state 13C NMR spectrum depicted in FIG. 34; and a solid-state 13C NMR spectrum depicted in FIG. 35. The signal exhibiting the lowest chemical shift in the chemical shift range of 90 to 210 ppm is, typically, at about 95.2±1 ppm.

The present invention provides yet another crystalline form of Tigecycline, designated Form XI, characterized by data selected from the group consisting of a powder XRD pattern with peaks at about 4.2, 8.4, 13.0 and 17.0±0.2 degrees two-theta; a powder XRD pattern with peaks at about 4.2, 8.4, 13.0, 17.0 and 18.5±0.2 degrees two-theta; a powder XRD pattern substantially as depicted in FIG. 9; a solid-state 13C NMR spectrum with signals at about 194.3, 177.9, 175.2, 142.1, and 131.9±0.2 ppm; a solid-state 13C NMR spectrum having chemical shift differences between the signal exhibiting the lowest chemical shift and another in the chemical shift range of 90 to 210 ppm of about 96.7, 80.3, 77.6, 44.5, and 34.3±0.1 ppm; a solid-state 13C NMR spectrum depicted in FIG. 36; and a solid-state 13C NMR spectrum depicted in FIG. 37. The signal exhibiting the lowest chemical shift in the chemical shift range of 90 to 210 ppm is, typically, at about 97.6±1 ppm.

The present invention provides yet another crystalline form of Tigecycline, designated Form XII, characterized by data selected from the group consisting of a powder XRD pattern with peaks at about 5.2, 8.2, 12.8 and 15.5±0.2 degrees two-theta; a powder XRD pattern with peaks at about 5.2, 8.2, 12.8, 15.5 and 20.4±0.2 degrees two-theta; a powder XRD pattern substantially as depicted in FIG. 10; a solid-state 13C NMR spectrum with signals at about 192.5, 174.2, 147.3, 131.0, and 114.5±0.2 ppm; a solid-state 13C NMR spectrum having chemical shift differences between the signal exhibiting the lowest chemical shift and another in the chemical shift range of 90 to 210 ppm of about 96.6, 78.3, 51.4, 35.1, and 18.6±0.1 ppm; a solid-state 13C NMR spectrum depicted in FIG. 38; and a solid-state 13C NMR spectrum depicted in FIG. 39. The signal exhibiting the lowest chemical shift in the chemical shift range of 90 to 210 ppm is, typically, at about 95.9±1 ppm.

The present invention provides yet another crystalline form of Tigecycline, designated Form XIII, characterized by data selected from the group consisting of a powder XRD pattern with peaks at about 8.2, 16.4, 18.8 and 20.6±0.2 degrees two-theta; a powder XRD pattern substantially as depicted in FIG. 11; a solid-state 13C NMR spectrum with signals at about 192.7, 170.8, 130.6, 124.9, and 114.4±0.2 ppm; a solid-state 13C NMR spectrum having chemical shift differences between the signal exhibiting the lowest chemical shift and another in the chemical shift range of 90 to 210 ppm of about 97.1, 75.2, 35.0, 29.3, and 18.8±0.1 ppm; a solid-state 13C NMR spectrum depicted in FIG. 40; and a solid-state 13C NMR spectrum depicted in FIG. 41. The signal exhibiting the lowest chemical shift in the chemical shift range of 90 to 210 ppm is, typically, at about 95.6±1 ppm.

The present invention provides yet another crystalline form of Tigecycline, designated Form XVIII, characterized by data selected from the group consisting of a powder XRD pattern with peaks at about 9.2, 14.4, 15.2 and 16.7±0.2 degrees two-theta; a powder XRD pattern with peaks at about 4.4, 9.2, 14.4, 15.2 and 16.7±0.2 degrees two-theta; a powder XRD pattern substantially as depicted in FIG. 14; a solid-state 13C NMR spectrum with signals at about 175.0, 148.4, 142.8, 126.0, and 109.3±0.2 ppm; a solid-state 13C NMR spectrum having chemical shift differences between the signal exhibiting the lowest chemical shift and another in the chemical shift range of 90 to 210 ppm of about 79.6, 53.0, 47.4, 30.6, and 13.9±0.1 ppm; a solid-state 13C NMR spectrum depicted in FIG. 42; and a solid-state 13C NMR spectrum depicted in FIG. 43. The signal exhibiting the lowest chemical shift in the chemical shift range of 90 to 210 ppm is, typically, at about 95.4±1 ppm.

The present invention provides yet another crystalline form of Tigecycline, designated Form XIX, characterized by data selected from the group consisting of a powder XRD pattern with peaks at about 8.4, 9.1, 14.1 and 15.7±0.2 degrees two-theta; and a powder XRD pattern substantially as depicted in FIG. 15.

The present invention provides yet another crystalline form of Tigecycline, designated Form XX, characterized by data selected from the group consisting of a powder XRD pattern with peaks at about 7.0, 8.8, 10.0 and 17.5±0.2 degrees two-theta; and a powder XRD pattern substantially as depicted in FIG. 16.

The present invention provides yet another crystalline form of Tigecycline, designated Form XXII, characterized by data selected from the group consisting of a powder XRD pattern with peaks at about 9.5, 10.4, 13.2 and 14.0±0.2 degrees two-theta; a powder XRD pattern with peaks at about 9.5, 10.4, 13.2, 14.0, 15.1 and 16.7±0.2 degrees two-theta; and a powder XRD pattern substantially as depicted in FIG. 18.

The present invention provides yet another crystalline form of Tigecycline, designated Form XXIII, characterized by data selected from the group consisting of a powder XRD pattern with peaks at about 9.1, 10.0, 13.3 and 17.4±0.2 degrees two-theta; a powder XRD pattern with peaks at about 9.1, 10.0, 13.3, 17.4 and 19.2±0.2 degrees two-theta; and a powder XRD pattern as depicted in FIG. 19.

The present invention provides yet another crystalline form of Tigecycline, designated Form XXIV, characterized by data selected from the group consisting of a powder XRD pattern with peaks at about 4.8, 9.5, 14.0 and 15.6±0.2 degrees two-theta; a powder XRD pattern with peaks at about 4.8, 8.4, 9.5, 14.0 and 15.6±0.2 degrees two-theta; a powder XRD pattern substantially as depicted in FIG. 20; a solid-state 13C NMR spectrum with signals at about 194.8, 174.2, 142.4, 129.6, and 126.0±0.2 ppm; a solid-state 13C NMR spectrum having chemical shift differences between the signal exhibiting the lowest chemical shift and another in the chemical shift range of 90 to 210 ppm of about 99.7, 79.1, 47.3, 34.5, and 30.9±0.1 ppm; a solid-state 13C NMR spectrum depicted in FIG. 44; and a solid-state 13C NMR spectrum depicted in FIG. 45. The signal exhibiting the lowest chemical shift in the chemical shift range of 90 to 210 ppm is, typically, at about 95.1±1 ppm.

The present invention provides another crystalline form of Tigecycline, designated Form XXV, characterized by data selected from the group consisting of a powder XRD pattern with peaks at about 8.5, 12.7, 16.1 and 16.8±0.2 degrees two-theta; a powder XRD pattern with peaks at about 4.3, 8.5, 10.5, 12.7, 16.1 and 16.8±0.2 degrees two-theta; a powder XRD pattern substantially as described in FIG. 21; a solid-state 13C NMR spectrum with signals at about 196.0, 194.8, 192.6, 174.0, and 142.5±0.2 ppm; a solid-state 13C NMR spectrum having chemical shift differences between the signal exhibiting the lowest chemical shift and another in the chemical shift range of 90 to 210 ppm of about 101.0, 99.8, 97.6, 79.0, and 47.5±0.1 ppm; a solid-state 13C NMR spectrum depicted in FIG. 46; and a solid-state 13C NMR spectrum depicted in FIG. 47. The signal exhibiting the lowest chemical shift in the chemical shift range of 90 to 210 ppm is, typically, at about 95.0±1 ppm.

The present invention provides a crystalline form of Tigecycline, designated Form XXVI, characterized by data selected from the group consisting of a powder XRD pattern with peaks at about 6.0, 7.0, 9.1 and 10.1±0.2 degrees two-theta; and a powder XRD pattern substantially as depicted in FIG. 22.

The present invention provides a crystalline form of Tigecycline, designated Form XXVII, characterized by data selected from the group consisting of a powder XRD pattern with peaks at about 8.3, 8.9, 10.6, 13.6 and 15.8±0.2 degrees two-theta; and a powder XRD pattern substantially as depicted in FIG. 23.

In another aspect, the present invention provides methods for preparing Tigecycline Forms III, VI, VII, VIII, IX, X, XI, XII, XIII, XV, XVII, XVIII, XIX, XX, XXI, XXII, XXIII, XXIV, XXV, XXVI, XXVII and amorphous.

In another embodiment of the present invention, the present invention provides a pharmaceutical composition comprising any one or more of the crystalline Tigecycline described above, such as Forms VI, VIII, IX, X, XI, XII, XIII, XVIII, XIX, XX, XXII, XXIII, XXIV, XXV, XXVI, and XXVII Tigecycline, and one or more pharmaceutically acceptable excipient.

In another embodiment of the present invention, the present invention provides a pharmaceutical composition comprising any one or more of the crystalline Tigecycline described above, such as Forms III, VI, VII, VIII, IX, X, XI, XII, XIII, XV, XVII, XVIII, XIX, XX, XXI, XXII, XXIII, XXIV, XXV, XXVI, XXVII and amorphous Tigecycline made by the processes of the present invention, and one or more pharmaceutically acceptable excipient.

The present invention further encompasses a process for preparing a pharmaceutical formulation comprising combining one or more crystalline Tigecycline forms selected from the list consisting of: Forms VI, VIII, IX, X, XI, XII, XIII, XVIII, XIX, XX, XXII, XXIII, XXIV, XXV, XXVI and XXVII with at least one pharmaceutically acceptable excipient.

The present invention further encompasses the use of a crystalline Tigecycline selected from the list consisting of: Forms VI, VIII, IX, X, XI, XII, XIII, XVIII, XIX, XX, XXII, XXIII, XXIV, XXV, XXVI and XXVII of the present invention, for the manufacture of a pharmaceutical composition.

BRIEF DESCRIPTION OF THE FIGURES

FIG. 47 illustrates a solid-state 13C NMR spectrum in the range of 90 to 210 ppm for Tigecycline Form XXV.

DETAILED DESCRIPTION OF THE INVENTION

As used herein the term "G:R ratio" refers the accepted ratio to describe color in terms of green vs. red based on the RGB color model [Measuring colour, 3$^{rd}$ Ed./R.W.G. Hunt (1998)]. The colors green and red having a wavelength of about 550 nm and about 725 nm in the visible light spectrum, respectively. This ratio was used to describe the colour yellow throughout.

As used herein, "DDW" is meant to refer to double distilled water.

The purity of Tigecycline Forms VI, VIII, IX, X, XI, XII, XIII, XVIII, XIX, XX, XXII, XXIII, XXIV, XXV, XXVI and XXVII can be measured by any the skilled artisan in the art, for example by calculating % of contaminating form based on one or more characterizing peaks of the powder XRD pattern of Forms already known such as Forms I, II, III, VII, XV, XVII, XXI or based on NMR data. The determination may be made by determining the relative amount of the one or more characterizing peaks of the powder XRD pattern of Forms already known.

As used herein, the term "chemical shift difference" refers to the difference in chemical shifts between a reference signal and another signal in the same solid-state 13C NMR spectrum. In the present patent application the chemical shift differences were calculated by subtracting the chemical shift value of the signal exhibiting the lowest chemical shift (reference signal) in the solid-state 13C NMR spectrum in the range of 90 to 210 ppm from chemical shift values of another (observed) signals in the same solid-state NMR spectrum in the range of 90 to 210 ppm. These chemical shift differences are to provide a measurement for a substance, for example Tigecycline, of the present invention compensating for a phenomenon in NMR spectroscopy wherein, depending on the instrumentation, temperature, and calibration method used, a shift in the solid-state NMR "fingerprint" is observed. This shift in the solid-state NMR "fingerprint", having signals at certain positions, is such that although the individual chemical shifts of signals have altered, the difference between chemical shifts of each signal and another is retained.

Figure 1:
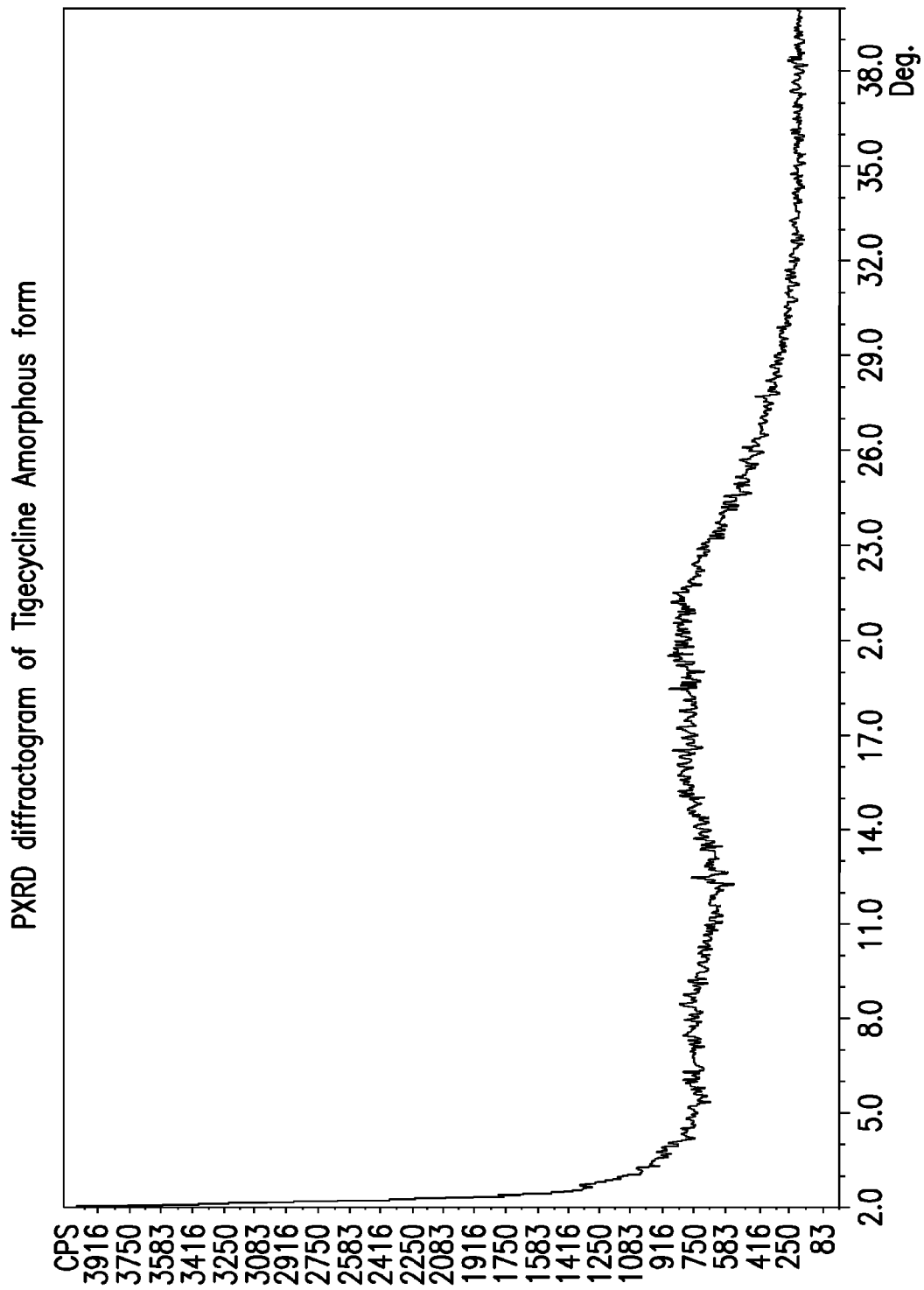
FIG. 1 illustrates a powder X-ray diffraction pattern for amorphous Tigecycline (as prepared by example 19).
Figure 24:
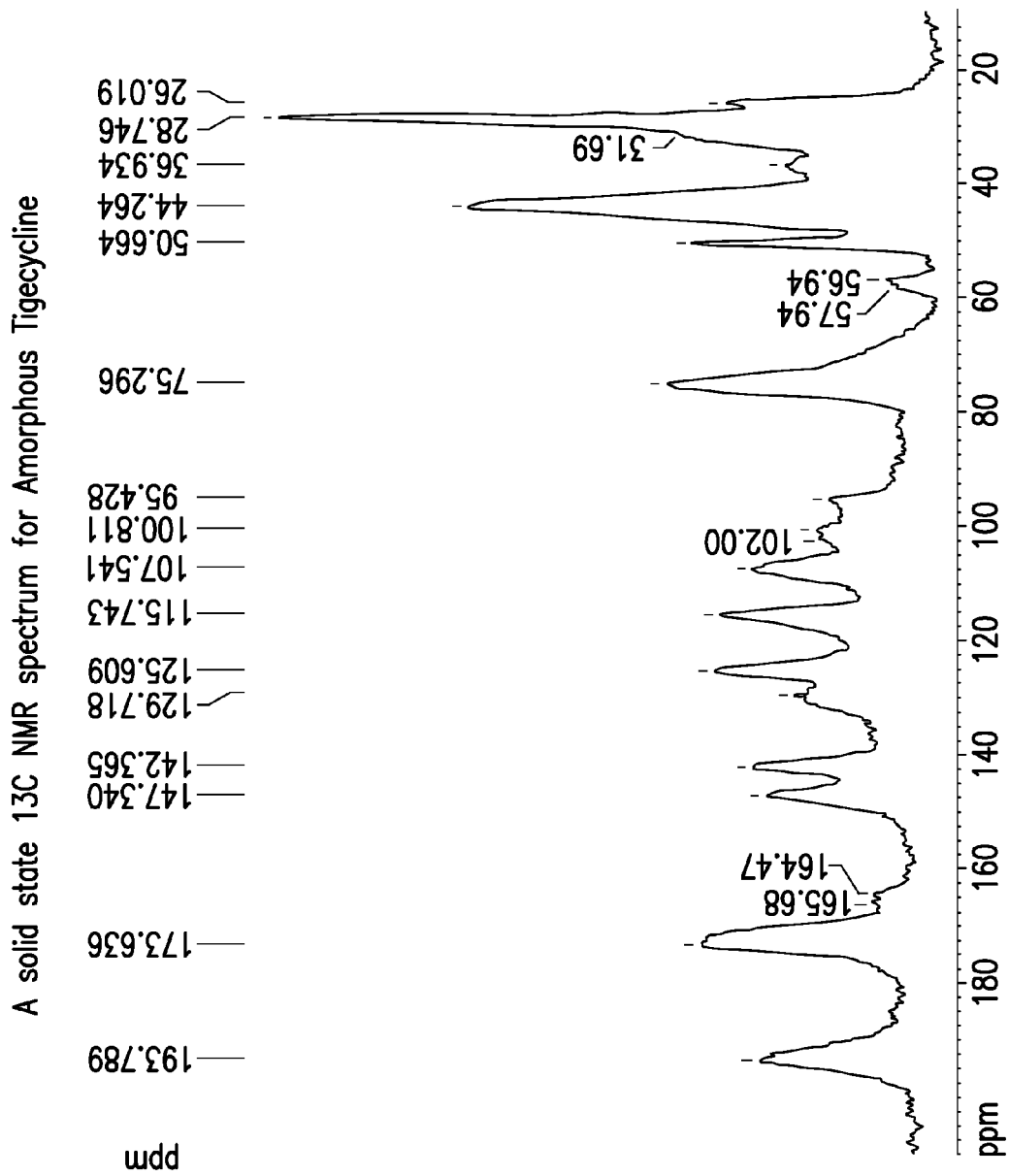
FIG. 24 illustrates a solid-state 13C NMR spectrum for Amorphous Tigecycline.
Figure 25:
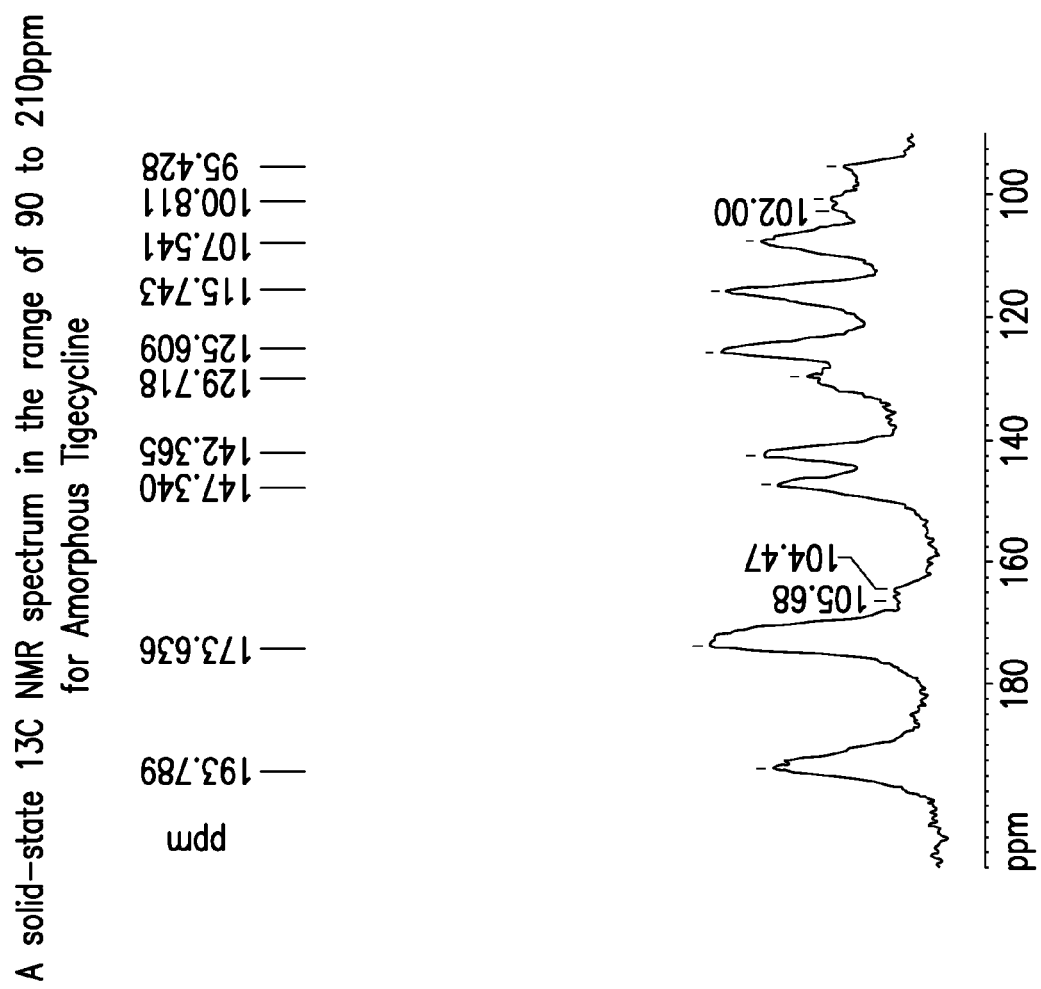
FIG. 25 illustrates a solid-state 13C NMR spectrum in the range of 90 to 210 ppm for Amorphous Tigecycline.
Figure 26:
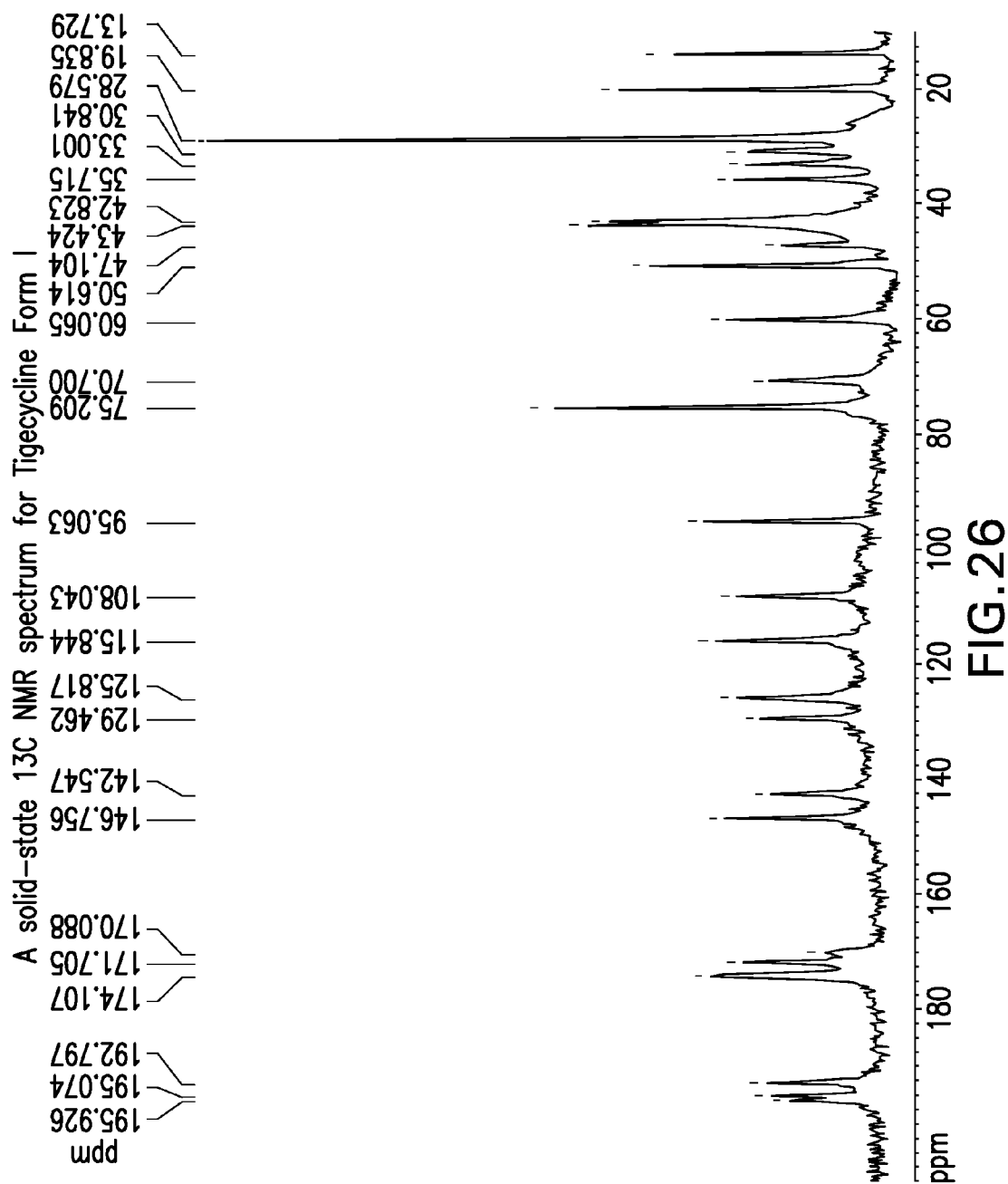
FIG. 26 illustrates a solid-state 13C NMR spectrum for Tigecycline Form I.
Figure 27:
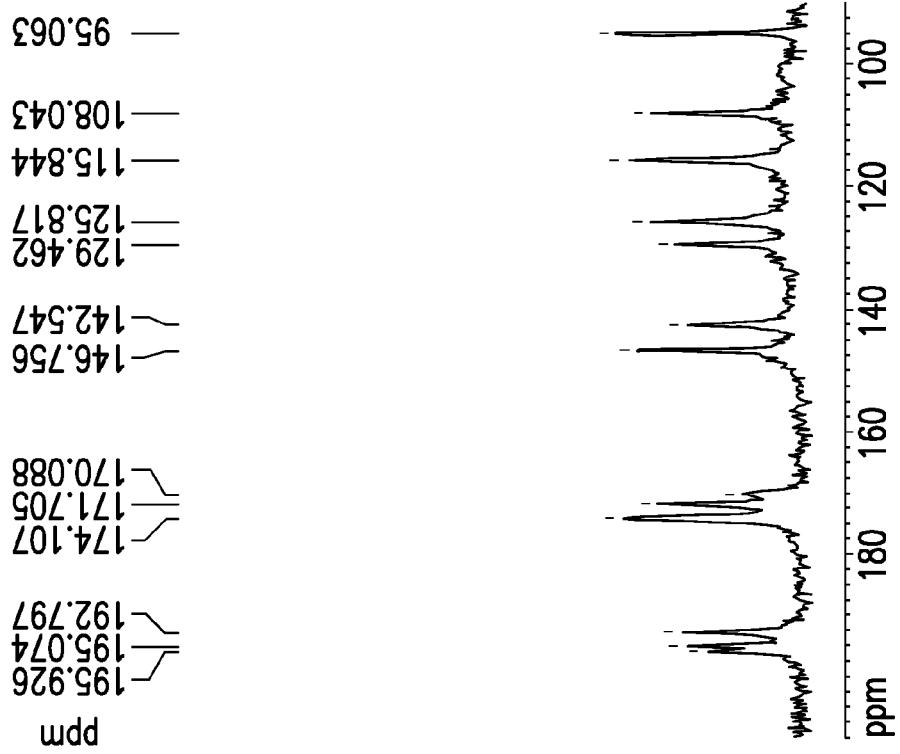
FIG. 27 illustrates a solid-state 13C NMR spectrum in the range of 90 to 210 ppm for Tigecycline Form I.

As used herein, the term "amorphous" refers to an form of Tigecycline as defined in WO 2007/127292, characterized by data selected from the group consisting of: a powder XRD pattern substantially as depicted in FIG. 1; a solid-state 13C NMR spectrum with signals at about 193.8, 173.6, 147.3142.4, and 125.6±0.2 ppm; a solid-state 13C NMR spectrum having chemical shift differences between the signal exhibiting the lowest chemical shift and another in the chemical shift range of 90 to 210 ppm of about 98.4, 78.2, 51.9, 47.0, and 30.27±0.1 ppm; a solid-state 13C NMR spectrum depicted in FIG. 24; and a solid-state 13C NMR spectrum depicted in FIG. 25. The signal exhibiting the lowest chemical shift in the chemical shift range of 90 to 210 ppm is, typically, at about 95.4±1 ppm As used herein, the term Form I refers to a crystalline form of Tigecycline as defined in WO 2007/127292, characterized by data selected from the group consisting of a powder XRD pattern with peaks at about 4.2, 9.1, 11.4, 14.0 and 15.7±0.2 degrees two-theta; a solid-state 13C NMR spectrum with signals at about 192.8, 174.1, 146.8, 129.5, and 125.8±0.2 ppm; a solid-state 13C NMR spectrum having chemical shift differences between the signal exhibiting the lowest chemical shift and another in the chemical shift range of 90 to 210 ppm of about 97.7, 79.0, 51.7, 34.4, and 30.7±0.1 ppm; a solid-state 13C NMR spectrum depicted in FIG. 26; and a solid-state 13C NMR spectrum depicted in FIG. 27. The signal exhibiting the lowest chemical shift in the chemical shift range of 90 to 210 ppm is, typically, at about 95.1±1 ppm. Form I typically has a weight loss, as measured by TGA, of between about 11.0-20.5% by weight and a water content, as measured by KF, of between about 0.5-5.0%.

Figure 2:
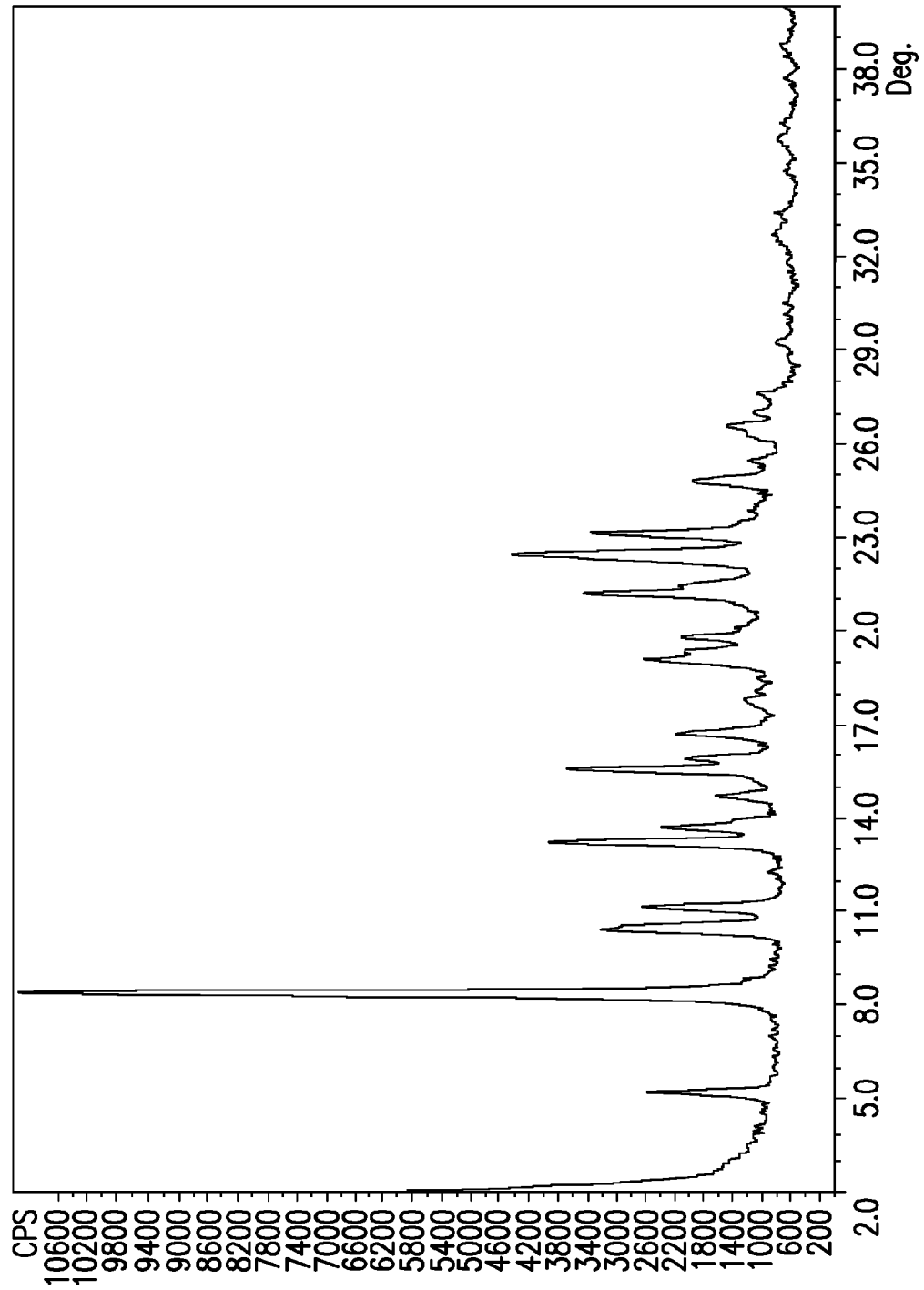
FIG. 2 illustrates a powder X-ray diffraction pattern for Tigecycline Form III (as prepared by example 1).
Figure 3:
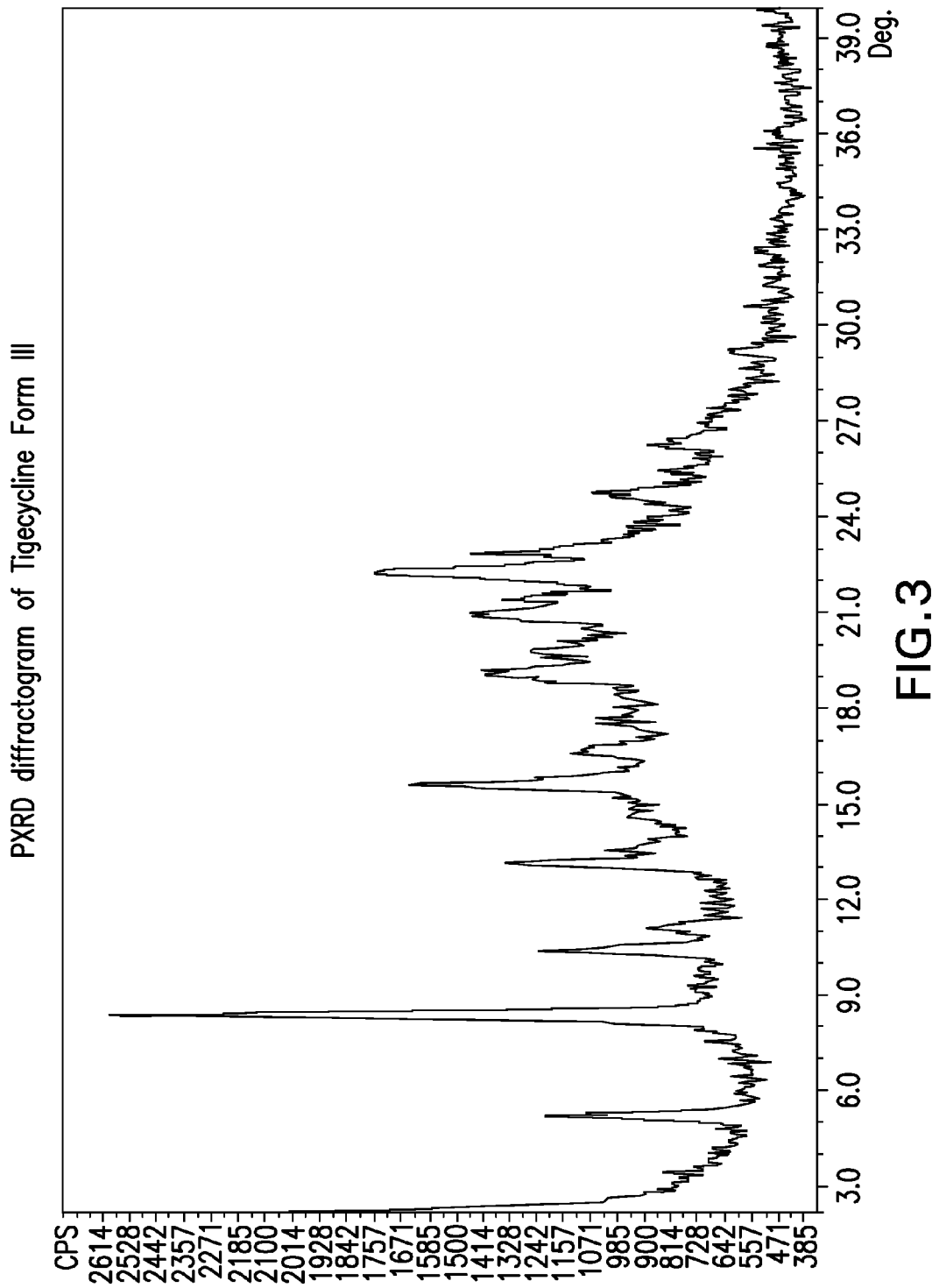
FIG. 3 illustrates a powder X-ray diffraction pattern for Tigecycline Form III (as prepared by example 2).

As used herein, Tigecycline Form III is characterized by a powder XRD pattern with peaks at about 5.2, 8.4, 10.4, 13.1 and 15.6±0.2 degrees two-theta. Preferably, the Form III may be further characterized by powder XRD pattern with peaks at about 19.2, 21.0 and 22.3±0.2 degrees two-theta or substantially as depicted by a powder XRD pattern as depicted in FIG. 2 or FIG. 3. Form III typically has a weight loss, as measured by TGA, of between about 1.5-6.5% by weight, while it typically has water content, as measured by KF, of between about 1.5-3.5% by weight.

Figure 5:
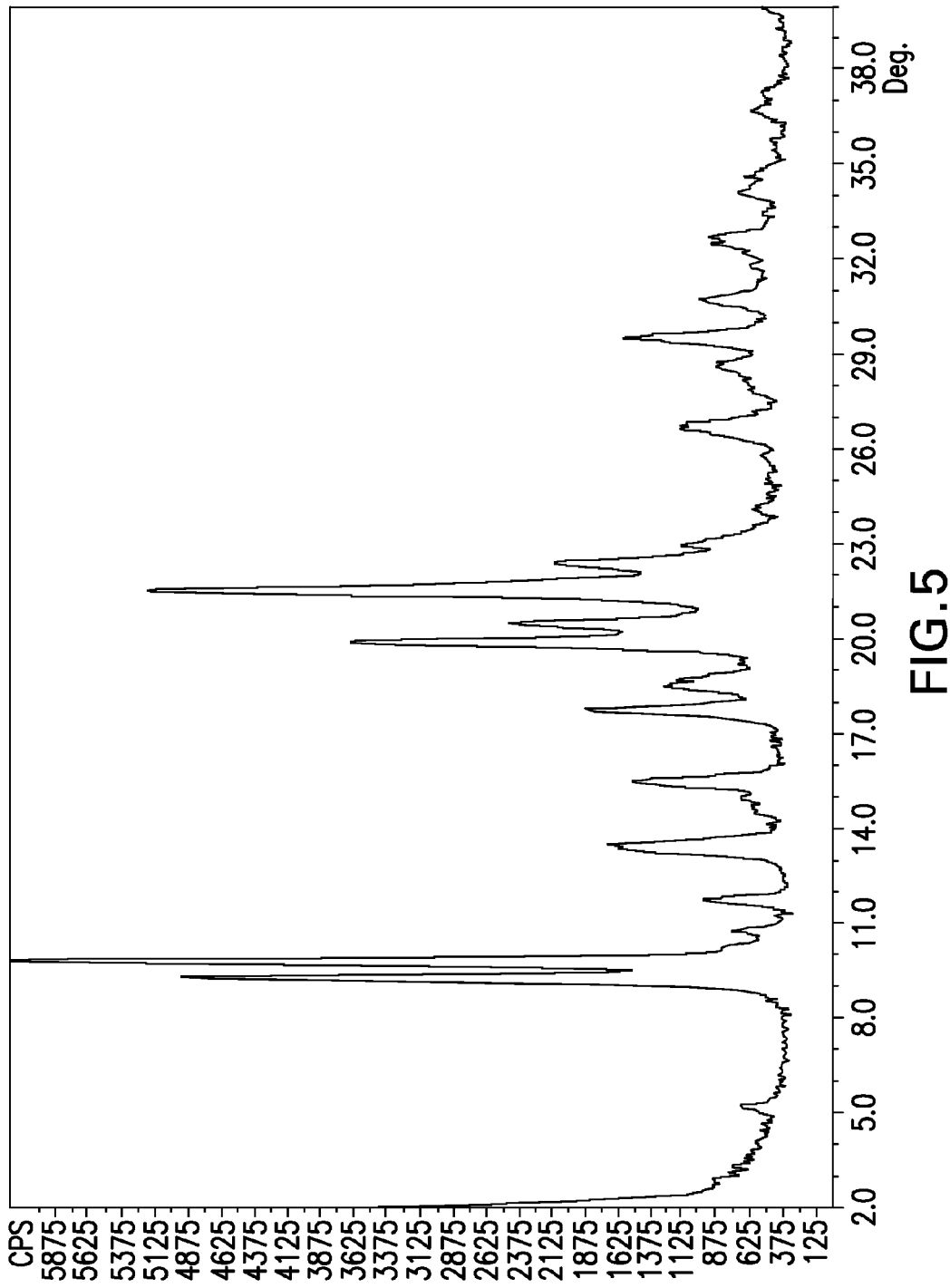
FIG. 5 illustrates a powder X-ray diffraction pattern for Tigecycline Form VII (as prepared by example 2-O).

As used herein, Tigecycline Form VII is characterized by a powder XRD pattern with peaks at about 9.3, 9.8, 13.5, 15.5 and 17.8±0.2 degrees two-theta. Preferably, the Form VII may be further characterized by a powder XRD pattern with one or more peaks selected from the list consisting of about 19.9, 20.5 and 21.5±0.2 degrees two-theta or substantially as depicted by a powder XRD pattern as depicted in FIG. 5. Form VII typically has a weight loss, as measured by TGA, of between about 4.0-6.5% by weight, while it typically has water content, as measured by KF, of between about 4.0-7.5% by weight.

Figure 12:
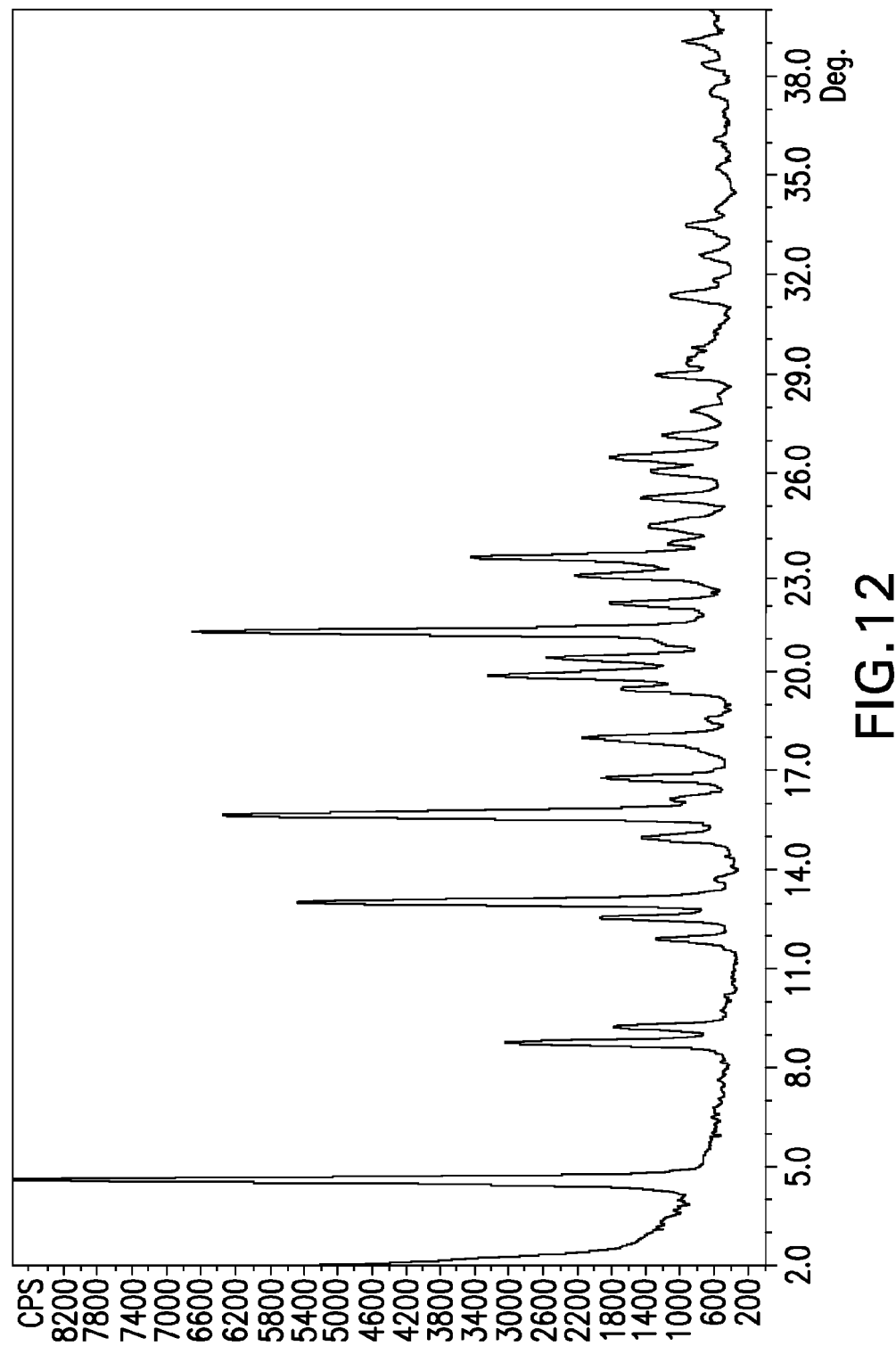
FIG. 12 illustrates a powder X-ray diffraction pattern for Tigecycline Form XV (as prepared by example 10).

As used herein, Tigecycline Form XV is characterized by a powder XRD pattern with peaks at about 4.6, 13.0, 15.7 and 19.9±0.2 degrees two-theta. Form XV may be further characterized by powder XRD pattern with one or more peaks selected from the list consisting of about 8.8, 12.6, 16.8, 18.0±0.2 degrees two-theta. Form XV may be further characterized by powder XRD pattern as depicted in FIG. 12.

Figure 13:
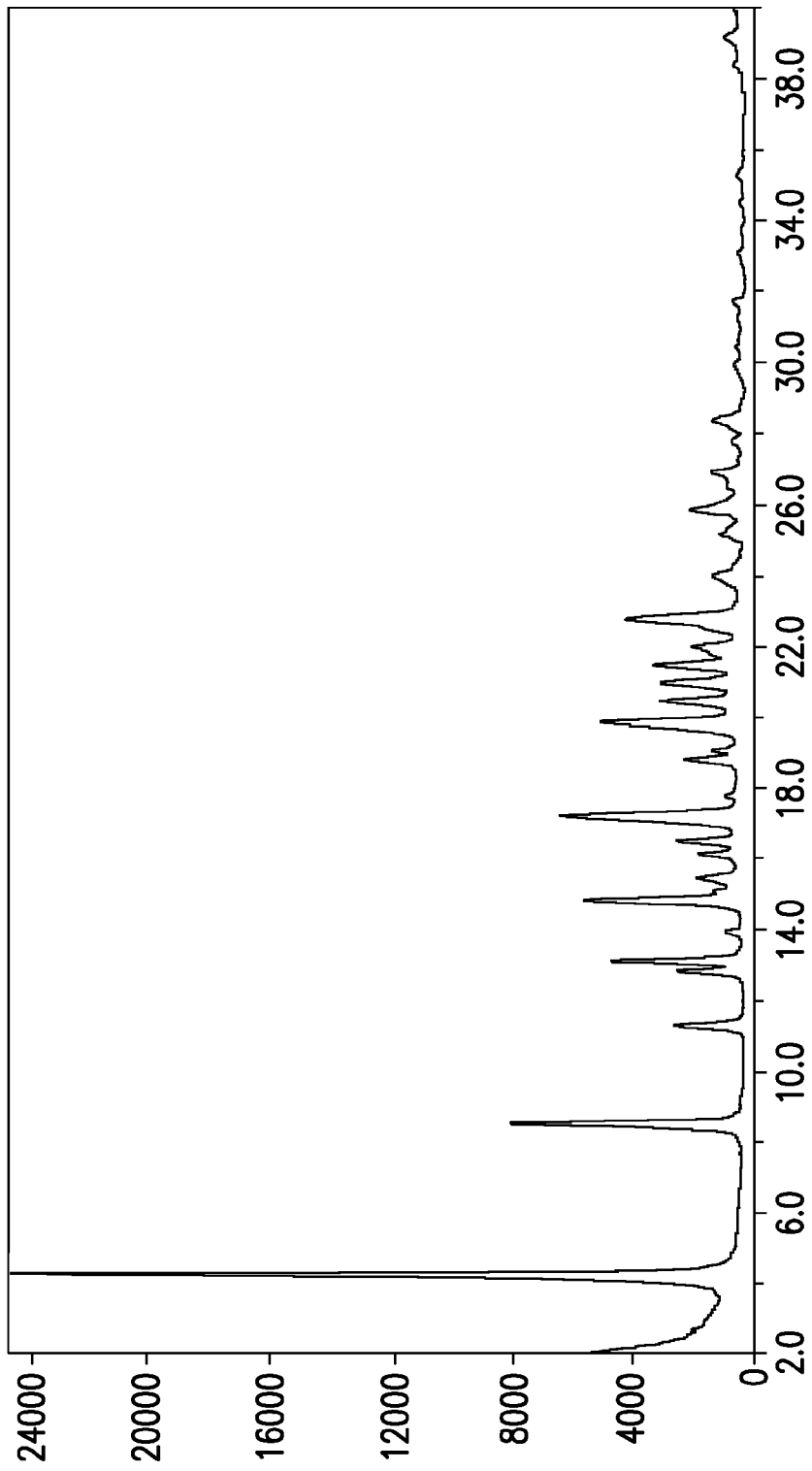
FIG. 13 illustrates a powder X-ray diffraction pattern for Tigecycline Form XVII (as prepared by example 11).

As used herein, Tigecycline Form XVII is characterized by a powder XRD pattern with peaks at about 4.3, 8.6, 14.8 and 17.2±0.2 degrees two-theta. Form XVII may be further characterized by a powder XRD pattern with one or more peaks selected from the list consisting of about 11.3, 13.1, 16.5 and 19.9±0.2 degrees two-theta or substantially as depicted by a powder XRD pattern as depicted in FIG. 13. Form XVII typically has a weight loss, as measured by TGA, of between about 9.0-11.5% by weight, while it typically has water content, as measured by KF, of between about 0.2-1.0% by weight.

Figure 17:
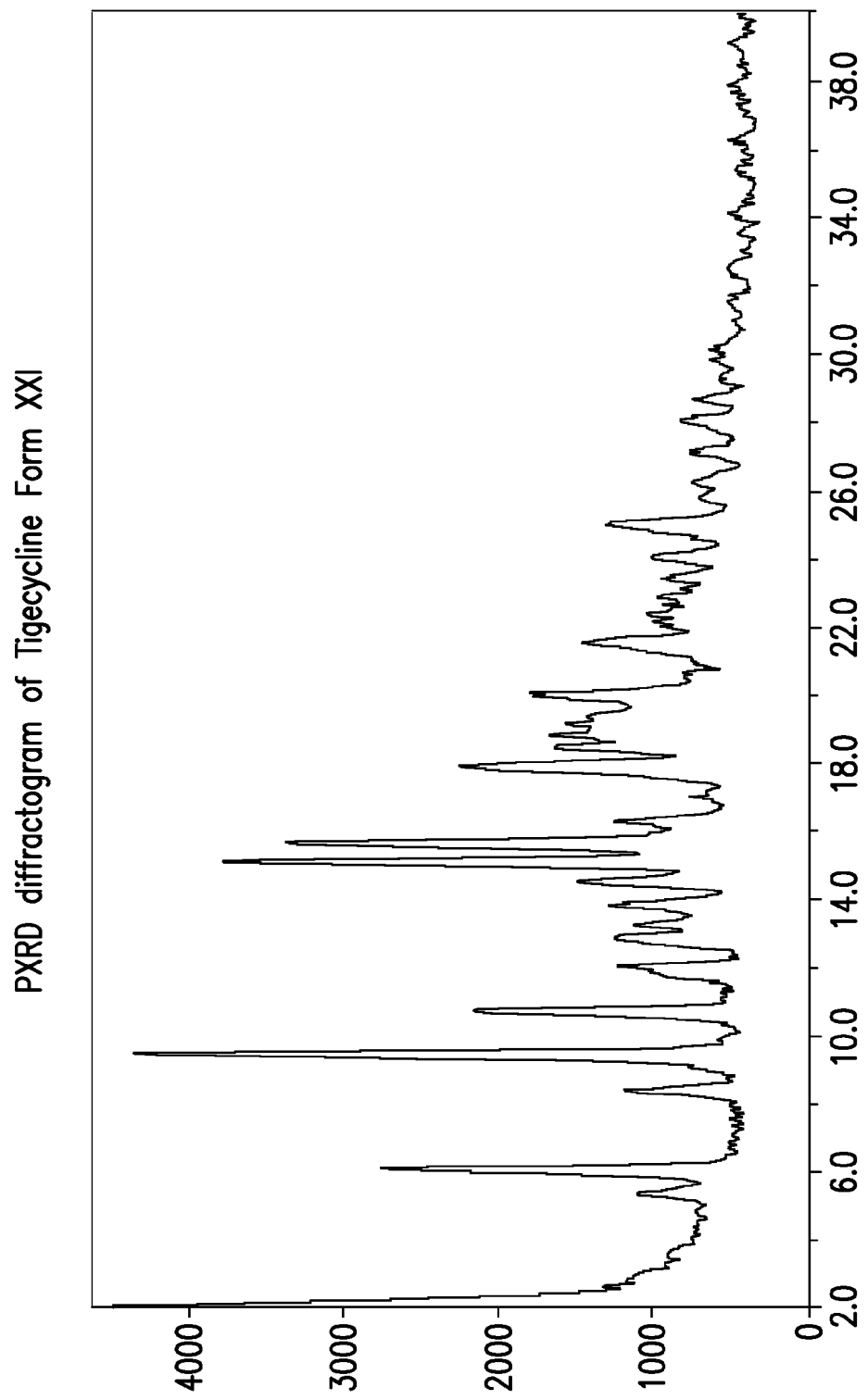
FIG. 17 illustrates a powder X-ray diffraction pattern for Tigecycline Form XXI (as prepared by example 15).

As used herein, Tigecycline Form XXI is characterized by a powder XRD pattern with peaks at about 6.1, 9.5, 15.0 and 15.7±0.2 degrees two-theta. Form XXI may be further characterized by a powder XRD pattern with peaks at about 10.7, 12.0, 14.5 and 17.9±0.2 degrees two-theta or substantially as depicted by a powder XRD pattern as depicted in FIG. 17. Form XXI typically has a weight loss, as measured by TGA, of between about 1.0-2.5% by weight, while it typically has water content, as measured by KF, of between about 1.0-2.5% by weight.

As used herein, the term "ambient temperature" or "room temperature" generally refers to a temperature of about 15° C. to about 30° C. The ambient temperature in which all of the examples were performed was about 20-25° C. Further, the term "spontaneous evaporation" refers to the evaporation of a solvent from a mixture, solution, or suspension without manipulating temperature and pressure of the environment of such mixture, solution or suspension. In general, such spontaneous evaporation takes place at about ambient temperature and about atmospheric pressure.

In one aspect of the present invention, processes for the preparation of amorphous Tigecycline are presented. In one process the preparation comprises stirring a suspension of Tigecycline in methyl acetate for at least 6 hours to obtain amorphous Tigecycline. The Tigecycline may then be recovered by filtering and drying. In another process, preparation comprises: providing a solution of methyl iso-butyl ketone and admixing n-heptane to obtain precipitated amorphous Tigecycline. Amorphous Tigecycline can then be recovered by filtering and drying.

The present invention also provides a process for preparing amorphous form of Tigecycline by exposing Form I of Tigecycline as described in WO '292, to about 80% to about 100% RH at about room temperature 15° C. to about 30° C. for about 1 day to about 9 days preferably about 5 to about 7 days to obtain amorphous Tigecycline.

The present invention further provides crystalline Tigecycline.

The present invention further provides a process for the preparation of Tigecycline Form III comprising: providing a solution of Tigecycline in dichloromethane and reducing the volume of the solution, preferably by drying over an inert desiccant to obtain a precipitate. Examples of desiccants include, but are not to be limited to, sodium sulfate and magnesium sulfate. Finally, the precipitate may undergo further solvent removal to dryness. The precipitate may be further dried overnight under vacuum, for example, at a temperature of about 40° C. In another aspect, the Form III may be prepared as described in example 1.

In another aspect, the Form III may be prepared by a process comprising providing a mixture of Tigecycline Form I as described in WO '292 and a solvent such as cyclohexane, di-isopropyl ether, methyl ethyl ketone ("MEK"), n-heptane, n-hexane and mixtures thereof; and maintaining the mixture, preferably at about room temperature, for about 6 to about 16 hours, preferably about 1 to about 12 hours to obtain Form III. Periodic PXRD may be taken in order to determine the ideal time period necessary as this time depends on the scale of process. Once Form III is obtained, it may be recovered by means known in the art such as filtering and drying under vacuum. When MEK is used, recovery preferably includes a drying step for about 10 to about 16 hours at 20° C. to about 60° C., preferably about 40° C. under vacuum.

Figure 4:
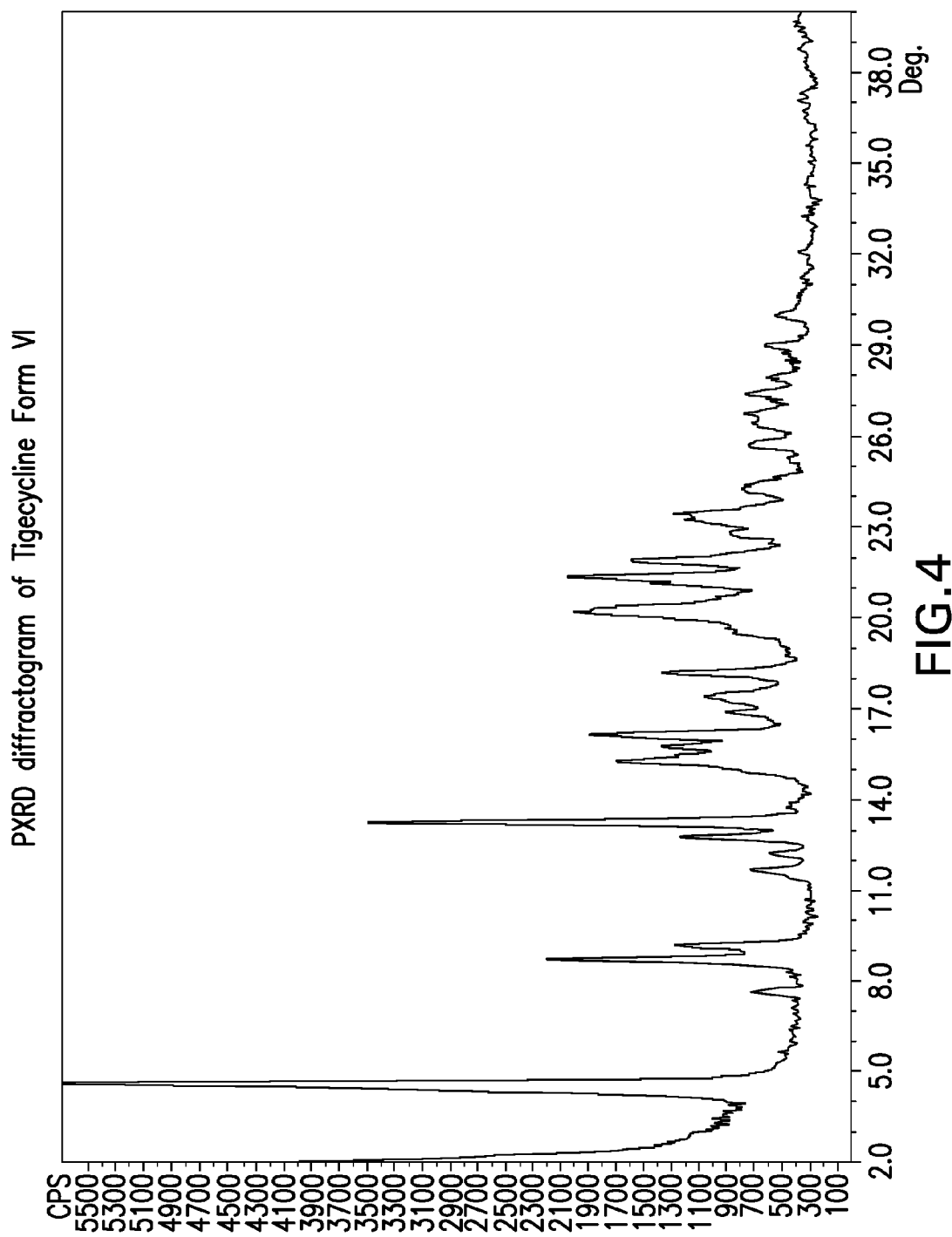
FIG. 4 illustrates a powder X-ray diffraction pattern for Tigecycline Form VI (as prepared by example 3).
Figure 28:
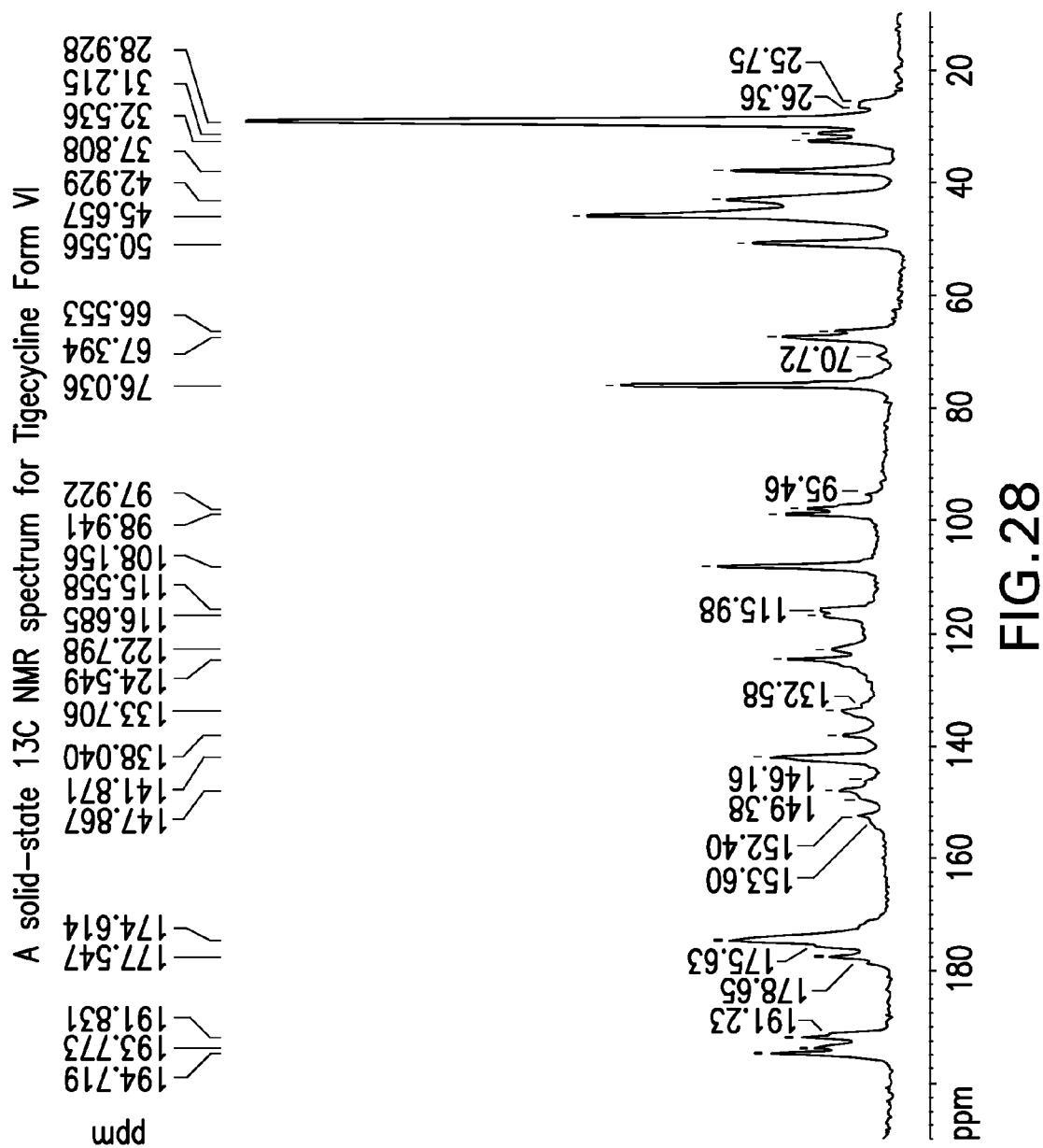
FIG. 28 illustrates a solid-state 13C NMR spectrum for Tigecycline Form VI.
Figure 29:
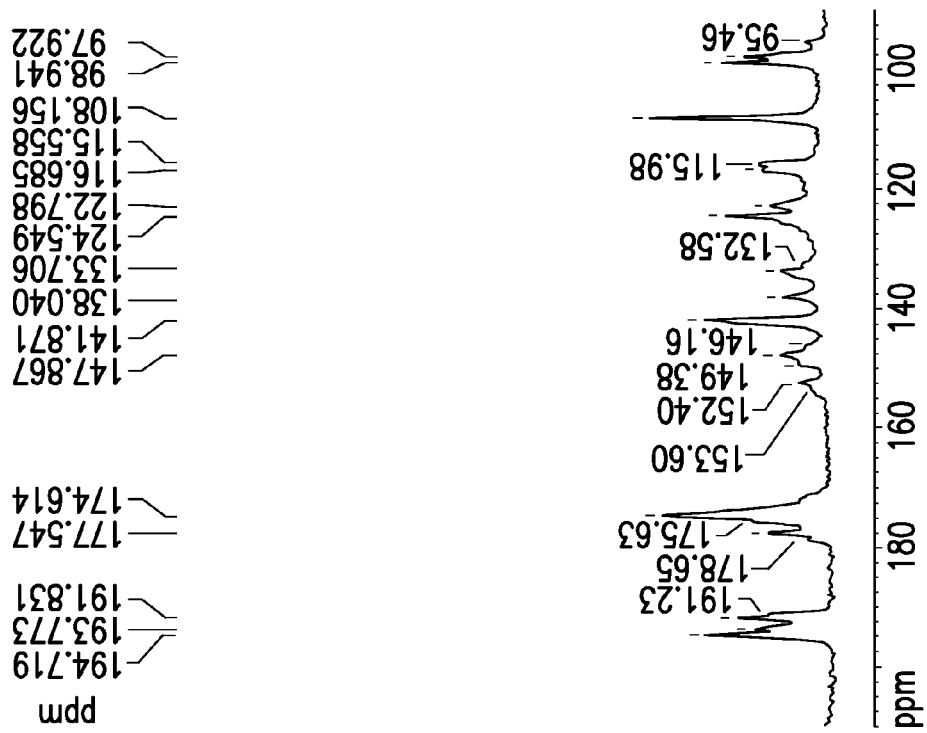
FIG. 29 illustrates a solid-state 13C NMR spectrum in the range of 90 to 210 ppm for Tigecycline Form VI.

The present invention provides yet another crystalline form of Tigecycline, designated Form VI, characterized by a powder XRD pattern with peaks at about 4.6, 8.8, 13.3 and 16.2±0.2 degrees two-theta and optionally a peak at about 7.7±0.2 degrees two-theta. Tigecycline Form VI may be further characterized by data selected from the group consisting of: a powder XRD pattern with one or more peaks selected from the list consisting of about 18.2, 20.2 and 21.4±0.2 degrees two-theta; a powder XRD pattern substantially as depicted in FIG. 4; a solid-state 13C NMR spectrum with signals at about 194.7, 174.6, 141.9, 108.2, and 98.9±0.2 ppm; a solid-state 13C NMR spectrum having chemical shift differences between the signal exhibiting the lowest chemical shift and another in the chemical shift range of 90 to 210 ppm of about 95.8, 75.7, 43.0 and 9.3±0.1 ppm; a solid-state 13C NMR spectrum substantially as depicted in FIG. 28; and a solid-state 13C NMR spectrum depicted in FIG. 29. The signal exhibiting the lowest chemical shift in the chemical shift range of 90 to 210 ppm is, typically, at about 98.9±0.2 ppm. Preferably, the Form VI may be further characterized by Form VI is typically yellow in color, having a G:R ratio of less than 1.8, preferably less than 1.4 and most preferably less than 1.3. Tigecycline Form VI is preferably in pure form having less than 10%, more preferably less than 5% and most preferably less than 1% of the crystalline form selected from the list consisting of: Forms I, II, III, IV and V as described in WO 2006/128150, which reference is incorporated herein by reference. Form VI typically has a weight loss, as measured by TGA, of between about 5.0-9.5% by weight, while it typically has water content, as measured by KF, of between about 1.5-3.5% by weight.

In another aspect, Tigecycline Form VI may be prepared by providing a solution of Tigecycline in DMF and admixing n-heptane to obtain a suspension. The suspension may then be stirred, preferably for about 30 minutes to about 4 hours, more preferably for about an hour. Periodic PXRD may be taken in order to determine the ideal time period necessary as this time depends on the scale of process. Once Form VI is obtained, it may be recovered by means known in the art such as filtering and drying under vacuum. Preferably, recovery includes a drying step for about 10 to about 16 hours at 20° C. to about 60° C., preferably about 40° C. optionally under vacuum.

In another aspect, the present invention further provides a process for the preparation of Tigecycline. Form VII may be prepared by a process comprising providing a mixture of Tigecycline Form I and methanol and maintaining the mixture, preferably by stirring, for at least about 20 minutes, for example for about 20 minutes to about 4 hours to obtain Form VII. Periodic PXRD may be taken in order to determine the ideal time period necessary as this time depends on the scale of process. Once Form VII is obtained, it may be recovered by means known in the art such as filtering and drying under vacuum. Recovery may include a drying step for about 10 to about 16 hours at 20° C. to about 60° C., preferably about 40° C. under vacuum.

In another aspect, the Form VII may be prepared as described in example 2O.

Figure 6:
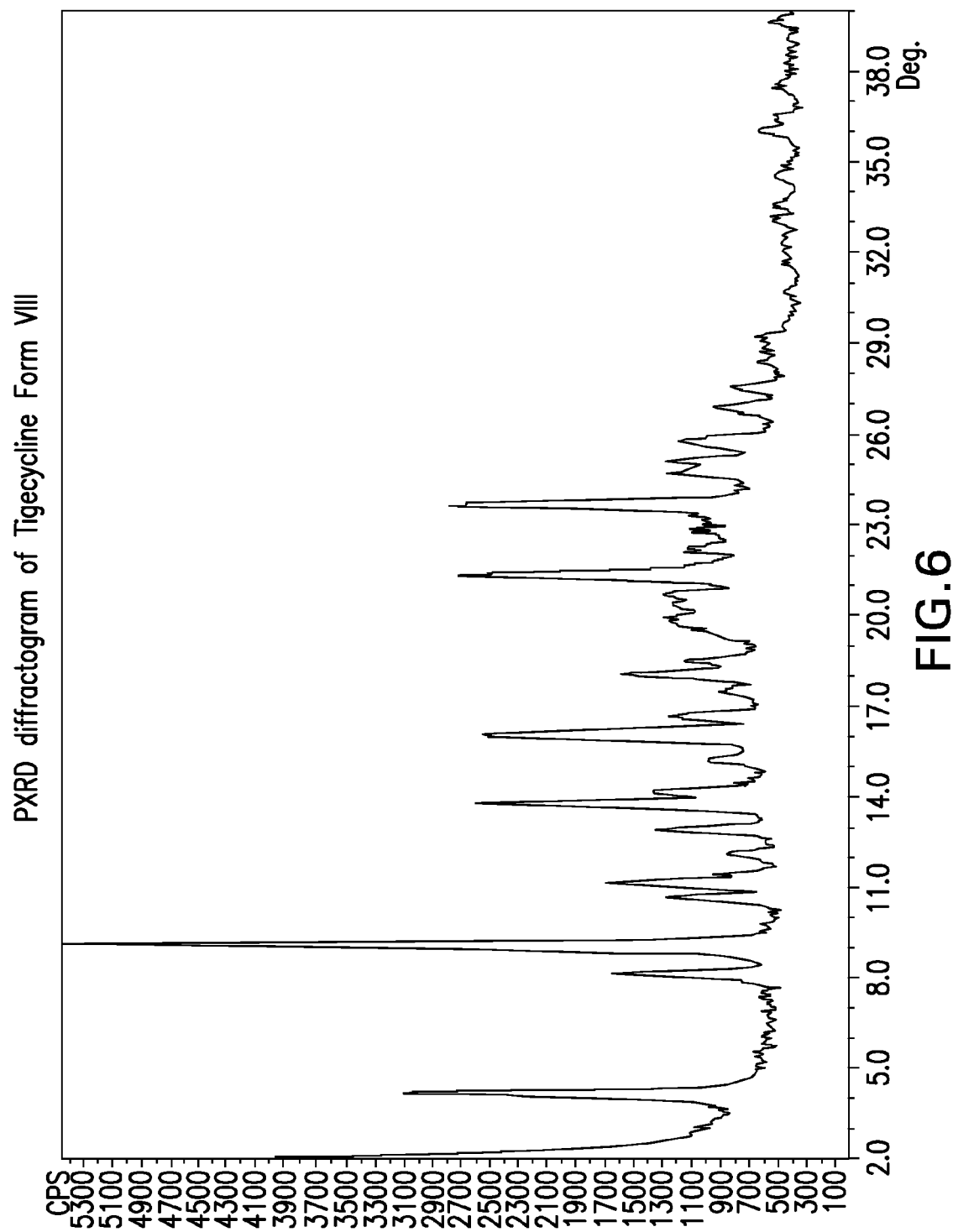
FIG. 6 illustrates a powder X-ray diffraction pattern for Tigecycline Form VIII (as prepared by example 4).
Figure 30:
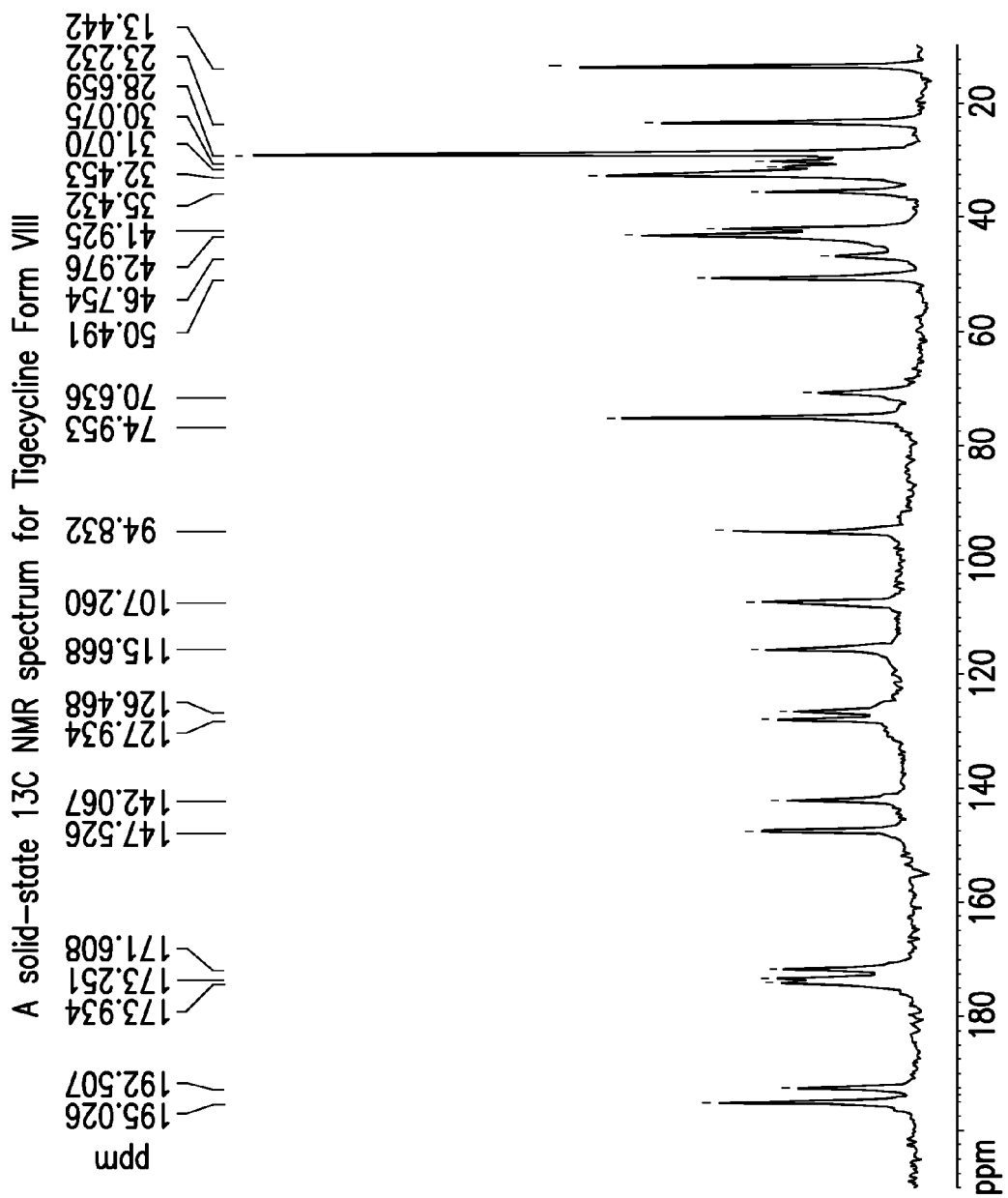
FIG. 30 illustrates a solid-state 13C NMR spectrum for Tigecycline Form VIII.
Figure 31:
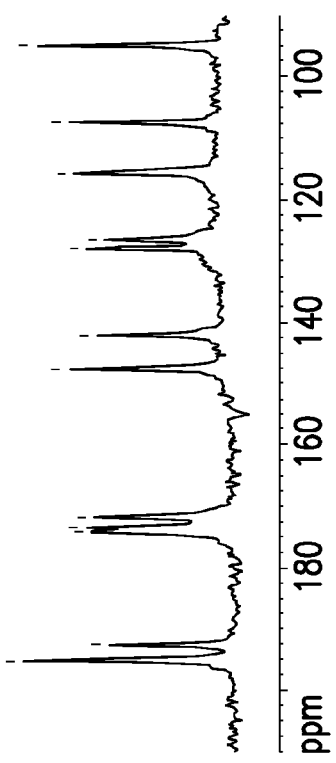
FIG. 31 illustrates a solid-state 13C NMR spectrum in the range of 90 to 210 ppm for Tigecycline Form VIII.

The present invention provides yet another crystalline form of Tigecycline, designated Form VIII, characterized by data selected from the list consisting of: a powder XRD pattern with peaks at about 4.1, 9.1, 13.8 and 16.0±0.2 degrees two-theta; a powder XRD pattern with peaks at about 4.1, 8.2, 9.1, 13.8 and 16.0±0.2 degrees two-theta.; a powder XRD pattern substantially as depicted in FIG. 6; a solid-state 13C NMR spectrum with signals at about 195.0, 147.5, 142.1, 127.9, and 126.5±0.2 ppm; a solid-state 13C NMR spectrum having chemical shift differences between the signal exhibiting the lowest chemical shift and another in the chemical shift range of 90 to 210 ppm of about 100.2, 52.7, 47.3, 33.1, and 31.7±0.1 ppm; a solid-state 13C NMR spectrum depicted in FIG. 30; and a solid-state 13C NMR spectrum depicted in FIG. 31. The signal exhibiting the lowest chemical shift in the chemical shift range of 90 to 210 ppm is, typically, at about 94.8±1 ppm. Preferably, the Form VIII may be further characterized by powder XRD pattern with one or more peaks selected from the list consisting of peaks at about 4.1, 8.2, 9.1, 11.1, 13.8, 16.0, 21.3 and 23.6±0.2 degrees two-theta . . . . Form VIII typically has a weight loss, as measured by TGA, of between about 6.0-15.0% by weight, while it typically has water content, as measured by KF, of between about 1.0-3.0% by weight. Tigecycline Form VIII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another aspect of the present invention, Form VIII may be prepared by reducing the volume of a solution of Tigecycline in dichloromethane and admixing a $C_{4-7}$ ester, preferably ethyl acetate, a $C_{5-10}$ alkane, preferably n-heptane, or a $C_{4-10}$ ether, preferably di-n-butyl-ether with the solution to obtain a precipitate. Periodic PXRD may be taken in order to determine the ideal time period necessary as this time depends on the scale of process. Once Form VII is obtained, it may be recovered by means known in the art such as filtering and drying under vacuum.

Figure 7:
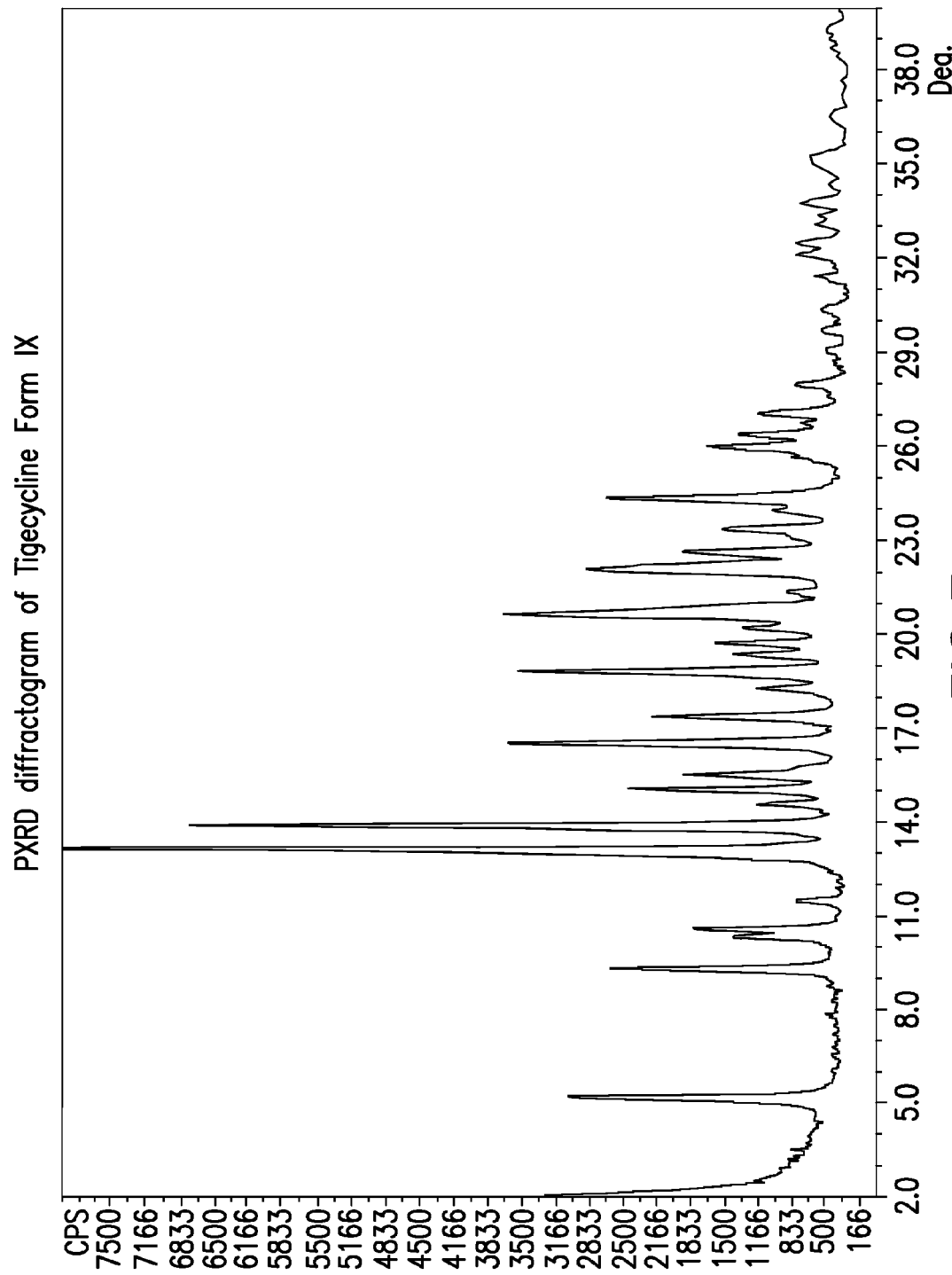
FIG. 7 illustrates a powder X-ray diffraction pattern for Tigecycline Form IX.
Figure 32:
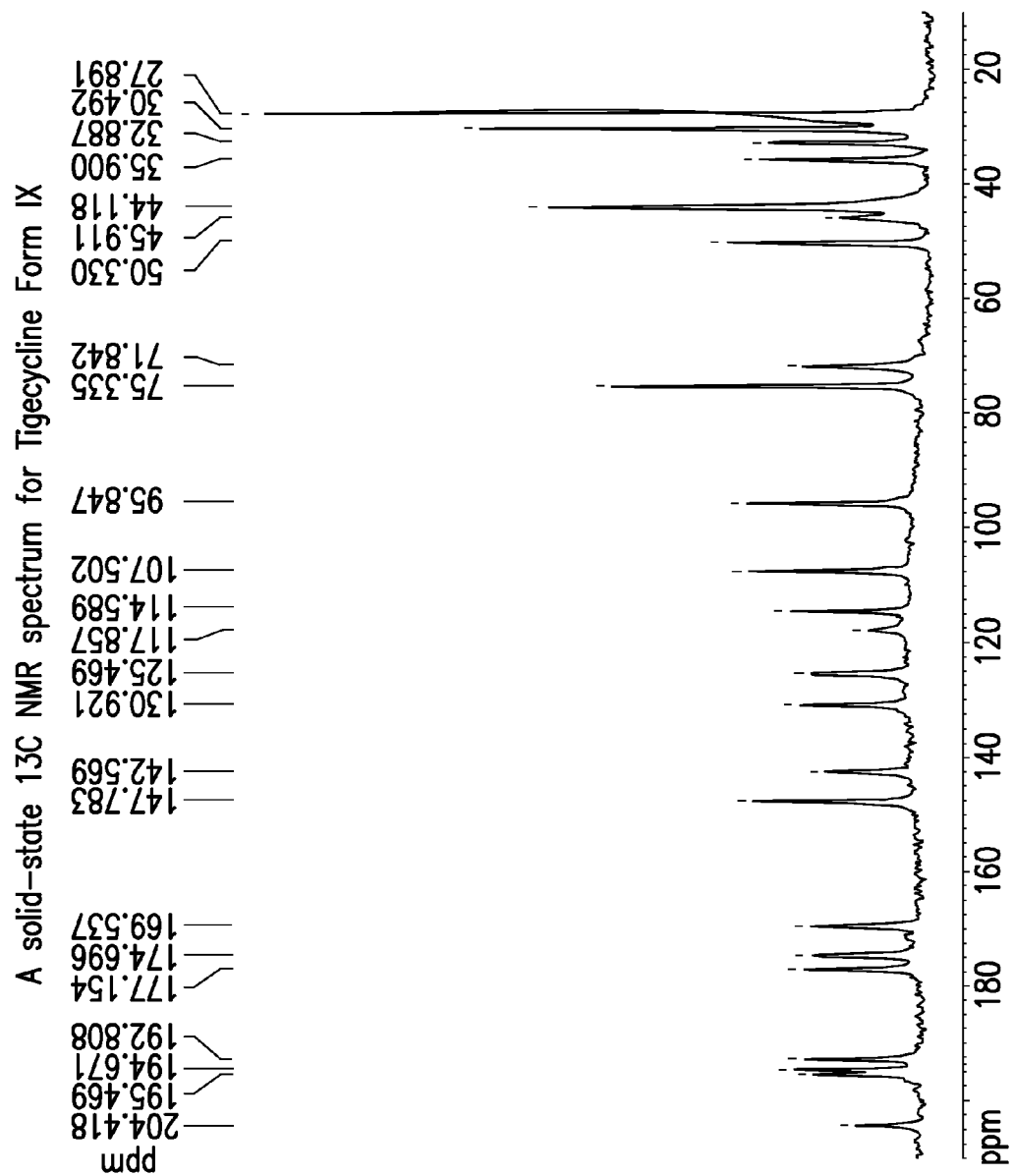
FIG. 32 illustrates a solid-state 13C NMR spectrum for Tigecycline Form IX.
Figure 33:
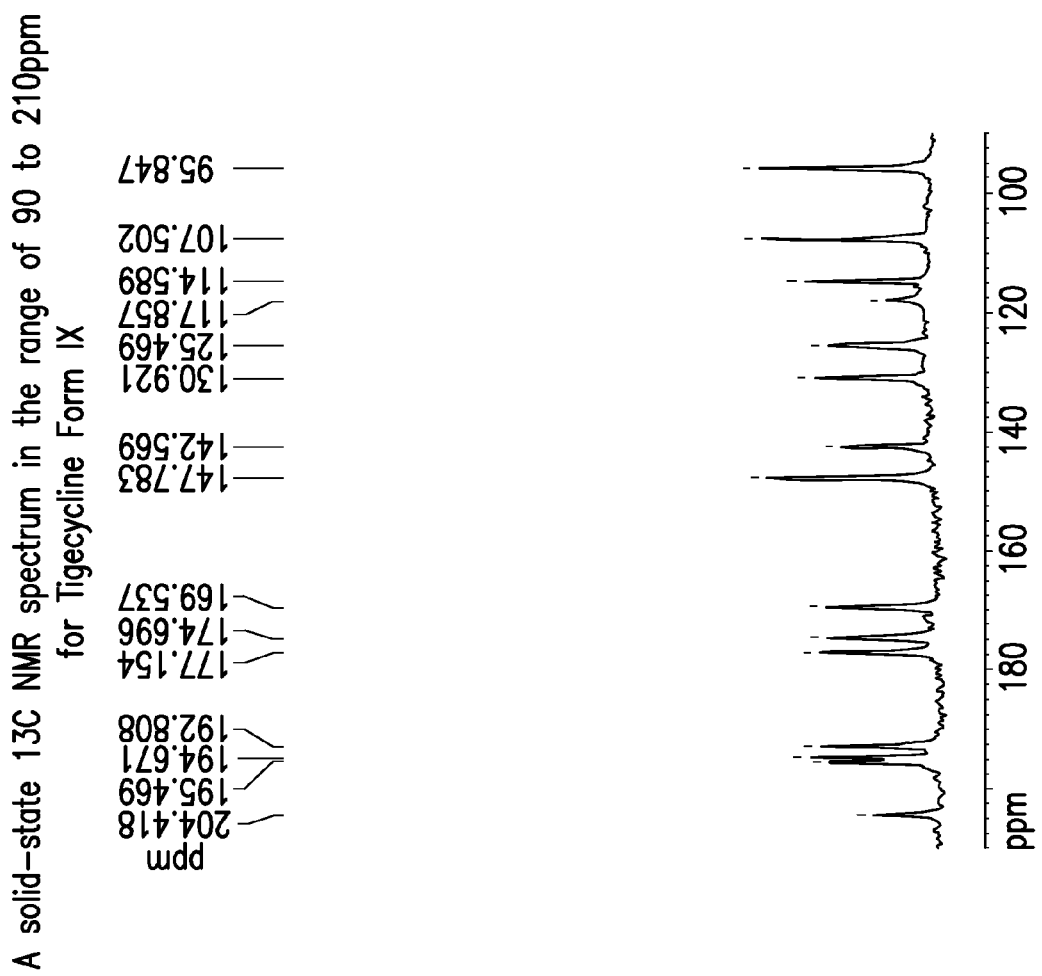
FIG. 33 illustrates a solid-state 13C NMR spectrum in the range of 90 to 210 ppm for Tigecycline Form IX.

The present invention provides yet another crystalline form of Tigecycline, designated Form IX, characterized by data selected from the group consisting of a powder XRD pattern with peaks at about 5.2, 9.3, 13.1, 13.8 and 16.5±0.2 degrees two-theta; a powder XRD pattern substantially as depicted in FIG. 7; a solid-state 13C NMR spectrum with signals at about 204.4, 192.8, 177.2, 174.7, and 169.5±0.2 ppm; a solid-state 13C NMR spectrum having chemical shift differences between the signal exhibiting the lowest chemical shift and another in the chemical shift range of 90 to 210 ppm of about 108.6, 97.0, 81.4, 78.9, and 73.7±0.1 ppm; a solid-state 13C NMR spectrum depicted in FIG. 32; and a solid-state 13C NMR spectrum depicted in FIG. 33. The signal exhibiting the lowest chemical shift in the chemical shift range of 90 to 210 ppm is, typically, at about 95.8±1 ppm. Preferably, the Form IX may be further characterized by a powder XRD pattern with one or more peaks selected from the list consisting at about 18.8, 20.6 and 22.1±0.2 degrees two-theta. Form IX is an acetone solvate, having a weight loss, as measured by TGA, of between about 6.5-9.0% by weight. It has water content, as measured by KF, of between about 1.0-1.5% by weight. Tigecycline Form IX is preferably in pure form having less than 10%, more preferably less than 5% and most preferably less than 1% of the crystalline form selected from the list consisting of: Forms I, II, III, IV and V as described in WO 2006/128150, wherein is incorporated in references.

In another aspect, the Form IX may be prepared by a process comprising providing a mixture of Tigecycline Form I as described in WO'292 and a solvent selected from acetone, isopropanol and mixtures thereof and maintaining it for at least 20 minutes, preferably about 20 minutes to about 72 hours, to obtain Form IX. Periodic PXRD may be taken in order to determine ideal time period necessary as this time depends on scale of process. Once Form IX is obtained, it may be recovered by means known in the art such as filtering and drying under vacuum. Recovery may include a drying step for about 10 to about 16 hours at 20° C. to about 60° C., preferably about 40° C. under vacuum.

In another aspect, the Form IX may be prepared as described in examples 2J-M.

Figure 8:
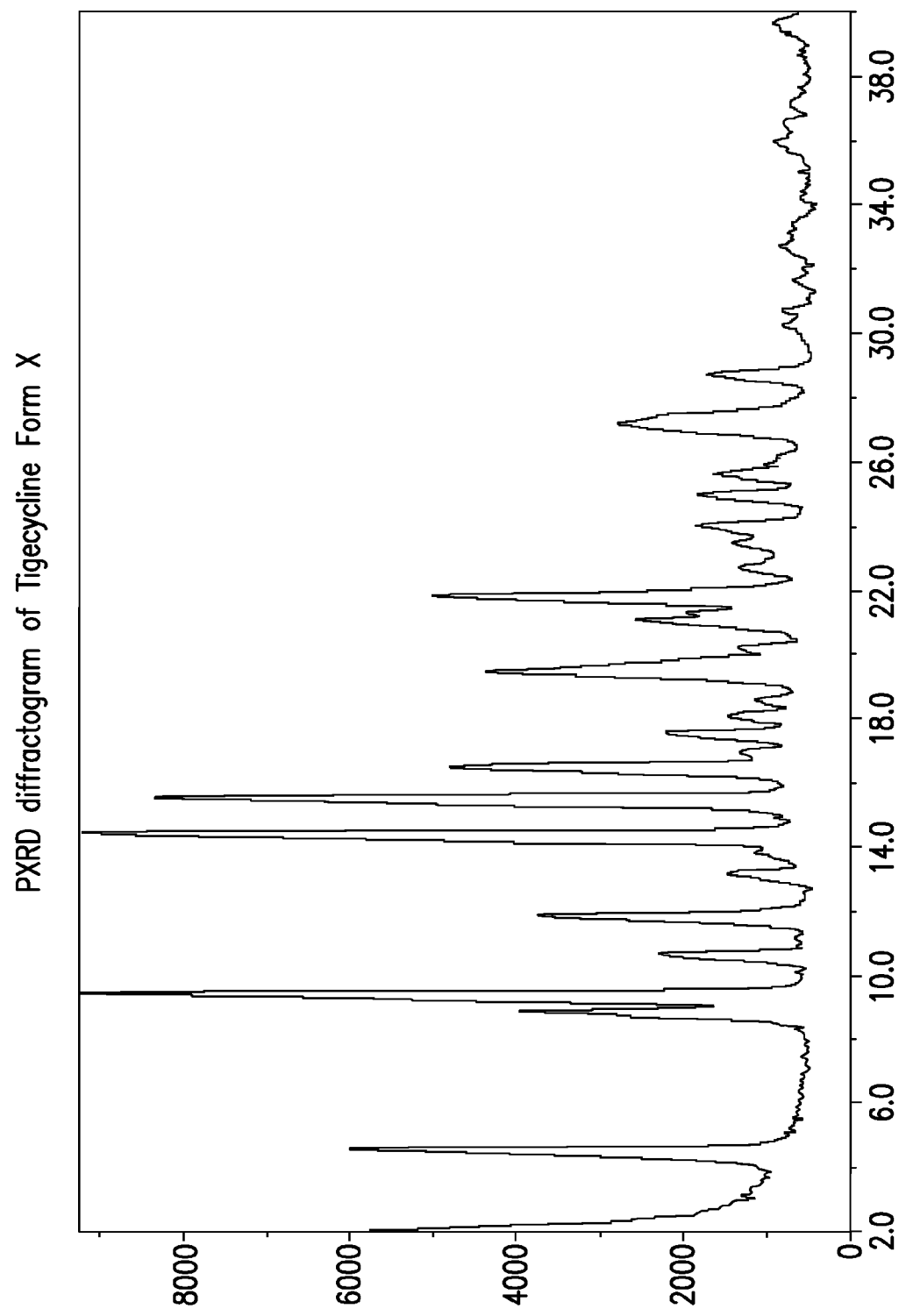
FIG. 8 illustrates a powder X-ray diffraction pattern for Tigecycline Form X (as prepared by example 2-I).
Figure 34:
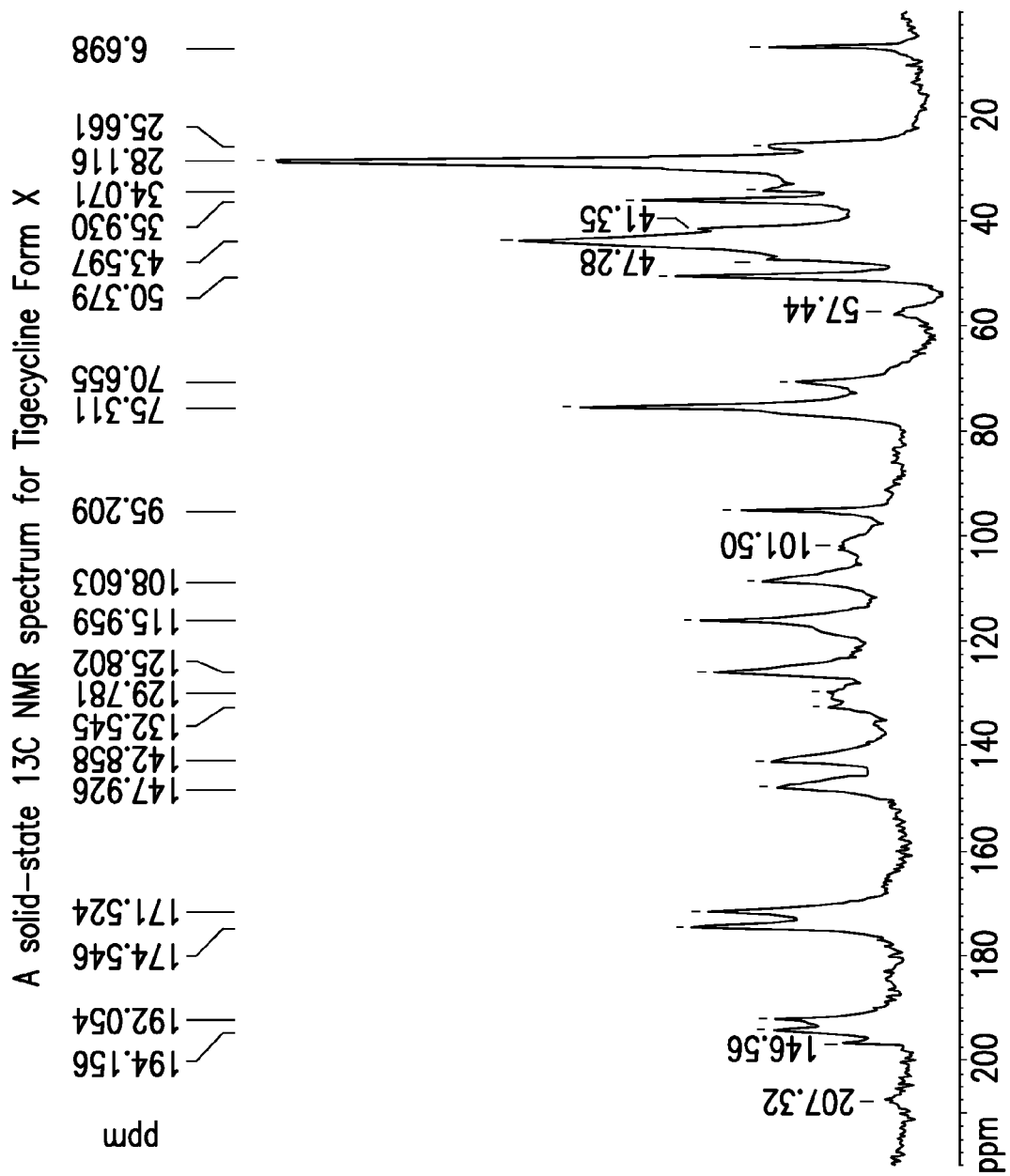
FIG. 34 illustrates a solid-state 13C NMR spectrum for Tigecycline Form X.
Figure 35:
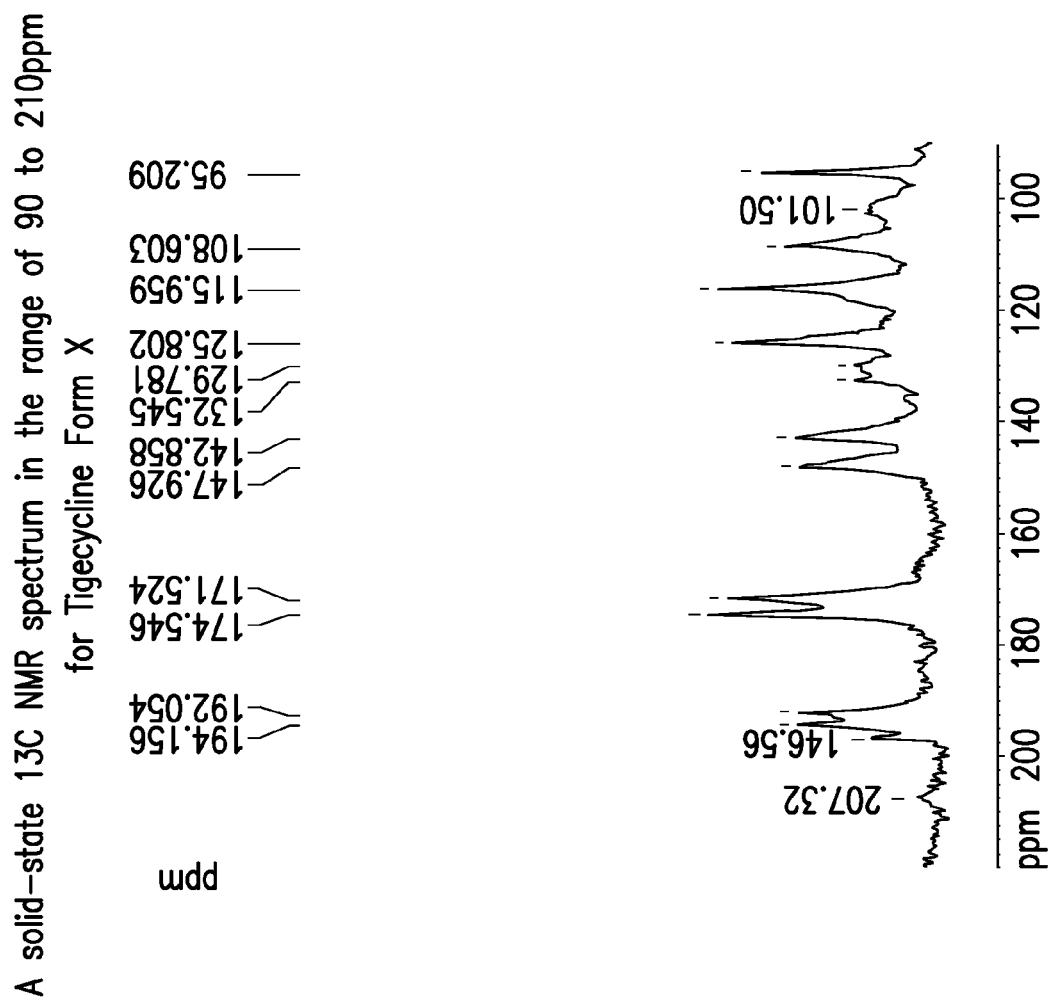
FIG. 35 illustrates a solid-state 13C NMR spectrum in the range of 90 to 210 ppm for Tigecycline Form X.

The present invention provides yet another crystalline form of Tigecycline, designated Form X, characterized by data selected from the group consisting of a powder XRD pattern with peaks at about 4.6, 9.4, 14.4, 15.5 and 16.5±0.2 degrees two-theta; a powder XRD pattern with peaks at about 4.6, 9.4, 10.7, 14.4, 15.5 and 16.5±0.2 degrees two-theta; a powder XRD pattern substantially as depicted in FIG. 8; a solid-state 13C NMR spectrum with signals at about 194.2, 192.1, 147.9, 142.9, 125.8, and 116.0±0.2 ppm; a solid-state 13C NMR spectrum having chemical shift differences between the signal exhibiting the lowest chemical shift and another in the chemical shift range of 90 to 210 ppm of about 99.0, 96.9, 52.7, 47.7, and 30.6±0.1 ppm; a solid-state 13C NMR spectrum depicted in FIG. 34; and a solid-state 13C NMR spectrum depicted in FIG. 35. The signal exhibiting the lowest chemical shift in the chemical shift range of 90 to 210 ppm is, typically, at about 95.2±1 ppm. Preferably, Form X may be further characterized by powder XRD pattern with one or more peaks selected from the list consisting of about 8.6, 11.6 and 21.6±0.2 degrees two-theta. Form X typically has a weight loss, as measured by TGA, of between about 12.5-13.5% by weight, while it typically has water content, as measured by KF, of between about 0.2-1.0% by weight. Tigecycline Form X is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another aspect, the Form X may be prepared by a process comprising providing a mixture of Tigecycline Form I as described in WO'292 and methyl ethyl ketone (MEK) as a solvent and maintaining for at least 10 minutes, preferably for 10 minutes to about 10 hours, more preferably for about 10 minutes to about 2 hours, to obtain Form X. Periodic PXRD may be taken in order to determine ideal time period necessary as this time depends on scale of process. Once Form X is obtained, it may be recovered by means known in the art such as filtering and drying under vacuum.

In another aspect, the Form X may be prepared as described in Example 2I.

Figure 9:
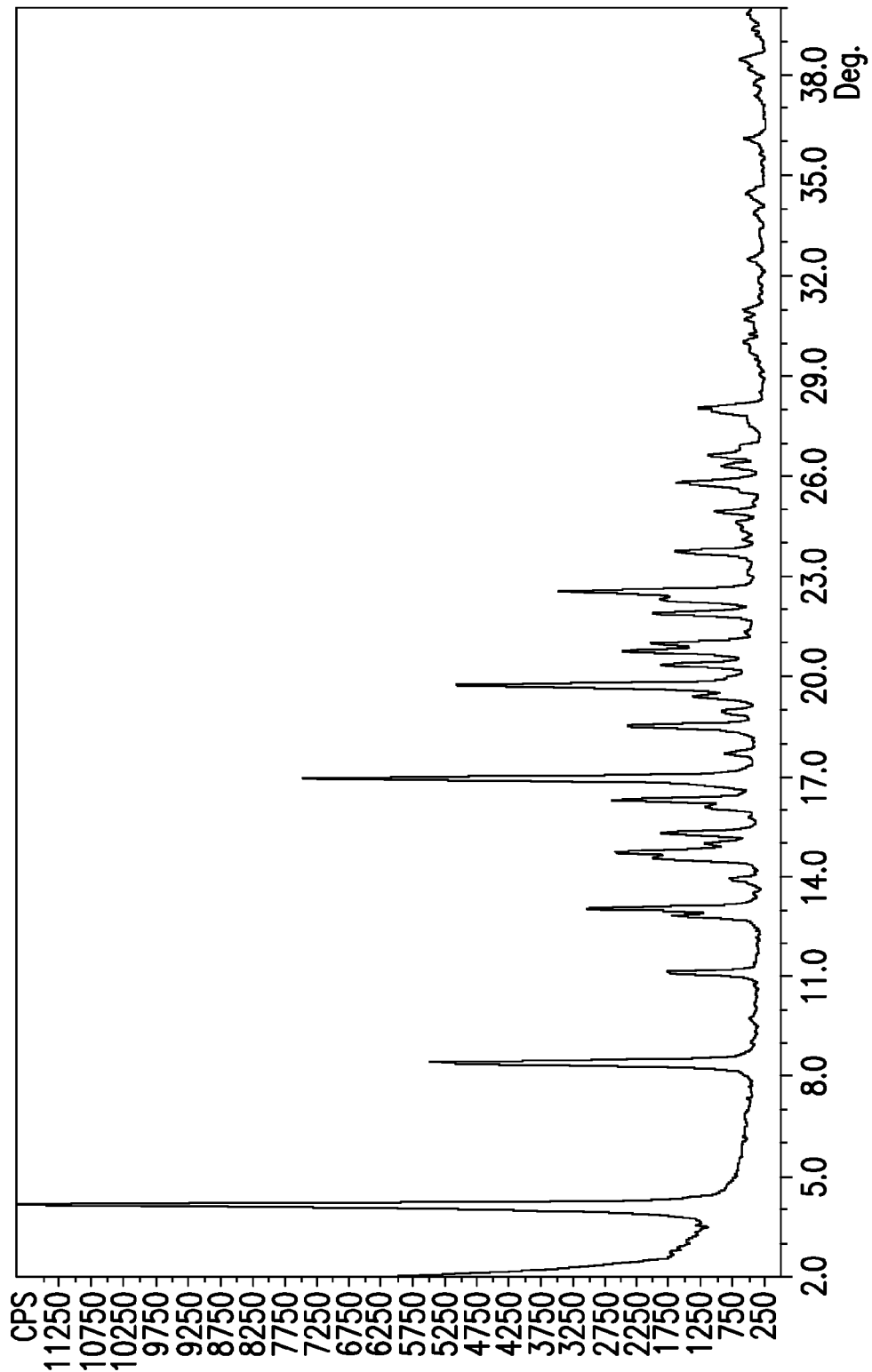
FIG. 9 illustrates a powder X-ray diffraction pattern for Tigecycline Form XI (as prepared by example 6).
Figure 36:
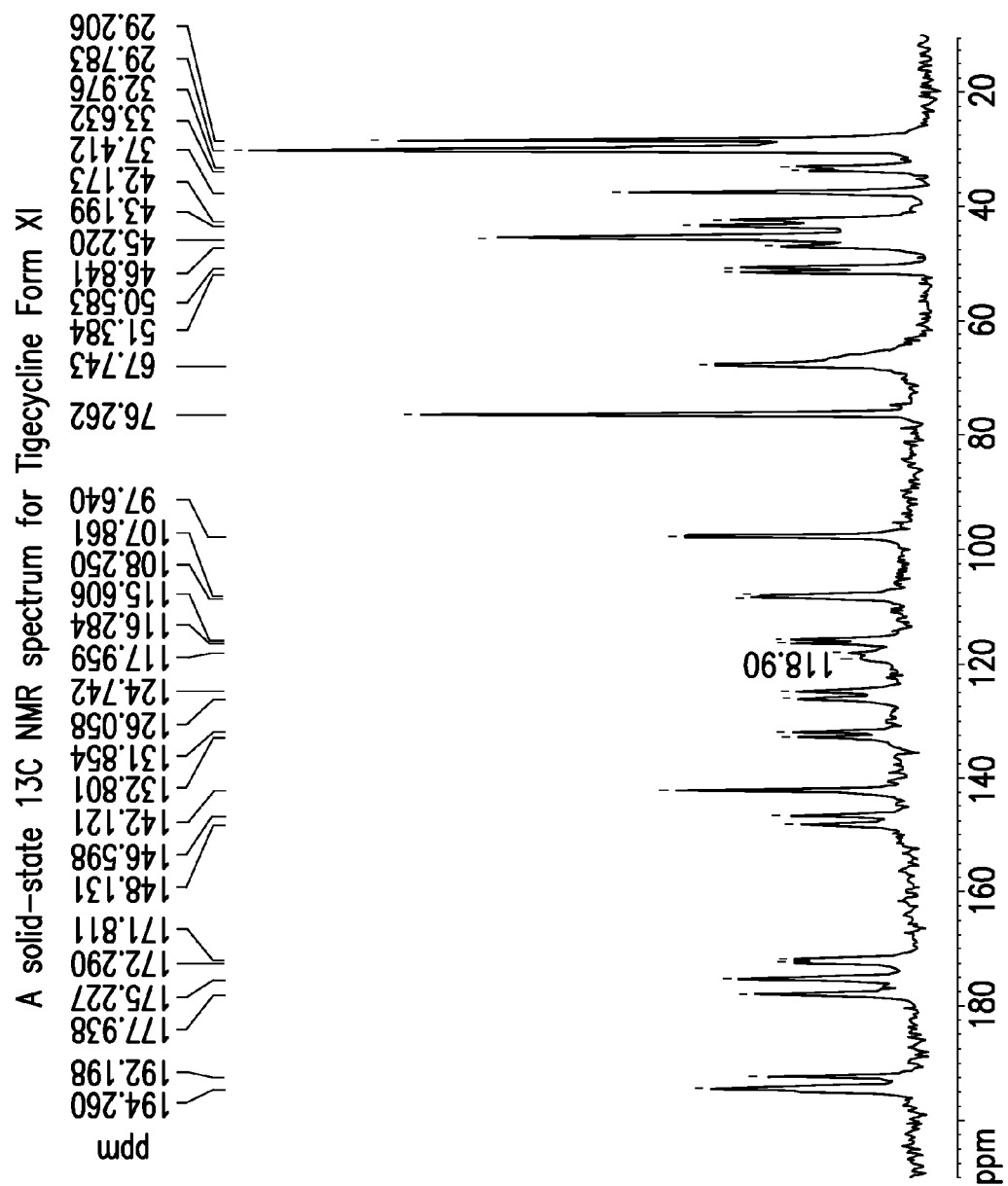
FIG. 36 illustrates a solid-state 13C NMR spectrum for Tigecycline Form XI.
Figure 37:
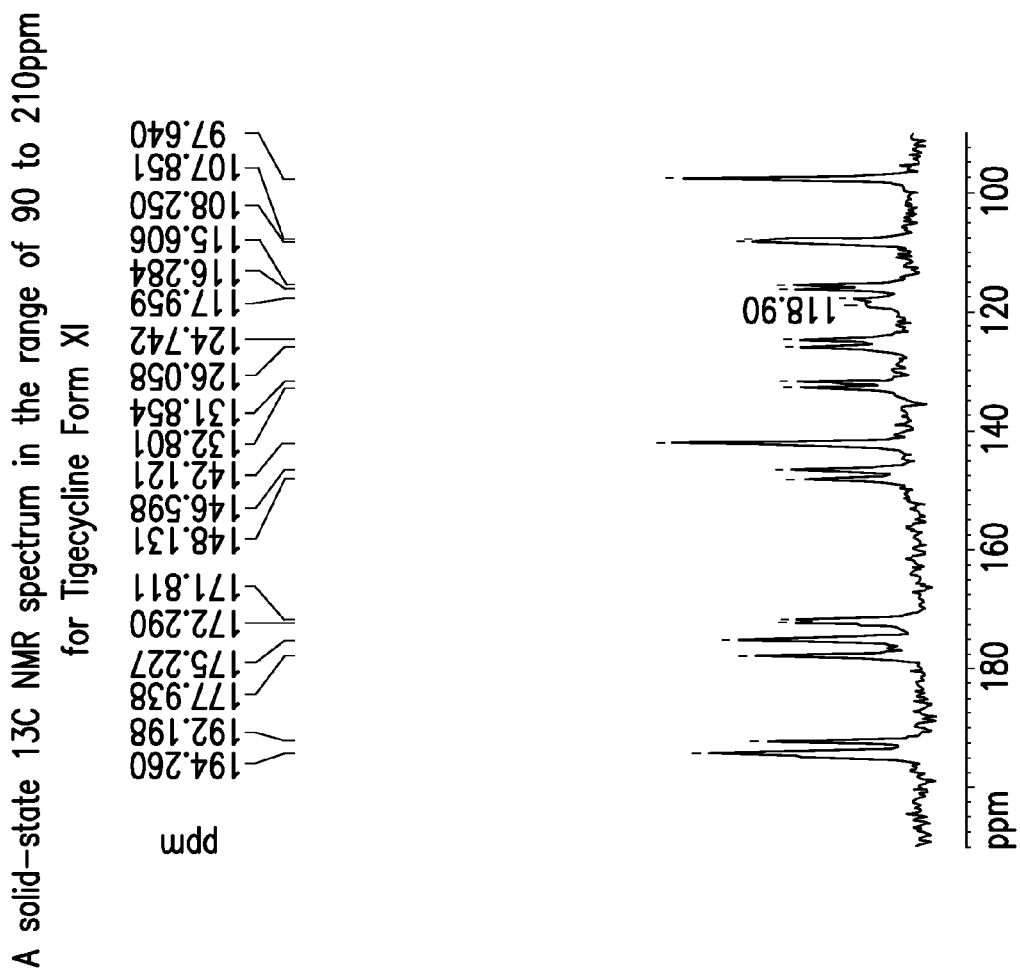
FIG. 37 illustrates a solid-state 13C NMR spectrum in the range of 90 to 210 ppm for Tigecycline Form XI.

The present invention provides yet another crystalline form of Tigecycline, designated Form XI, characterized by data selected from the group consisting of a powder XRD pattern with peaks at about 4.2, 8.4, 13.0 and 17.0±0.2 degrees two-theta; a powder XRD pattern with peaks at about 4.2, 8.4, 13.0, 17.0 and 18.5±0.2 degrees two-theta; a powder XRD pattern substantially as depicted in FIG. 9; a solid-state 13C NMR spectrum with signals at about 194.3, 177.9, 175.2, 142.1, and 131.9±0.2 ppm; a solid-state 13C NMR spectrum having chemical shift differences between the signal exhibiting the lowest chemical shift and another in the chemical shift range of 90 to 210 ppm of about 96.7, 80.3, 77.6, 44.5, and 34.3±0.1 ppm; a solid-state 13C NMR spectrum depicted in FIG. 36; and a solid-state 13C NMR spectrum depicted in FIG. 37. The signal exhibiting the lowest chemical shift in the chemical shift range of 90 to 210 ppm is, typically, at about 97.6±1 ppm. Preferably, Form XI may be further characterized by powder XRD pattern with one or more peaks selected from the list consisting of about 11.1, 16.3, 19.8±0.2 degrees two-theta. Form XI is typically yellow in color, having a G:R ratio of less than 1.8, preferably less than 1.4 and most preferably less than 1.3. Form XI typically has a weight loss, as measured by TGA, of between about 10.5-13.5% by weight, while it typically has water content, as measured by KF, of between about 0.2-4.5% by weight. Tigecycline Form XI is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another aspect, Tigecycline Form XI may be prepared by suspending Tigecycline in 2-methyltetrahydrofurane, preferably in about a 10 to 30 volume ratio, preferably in about a 20 volume ratio, relative to the amount of Tigecycline and maintaining, preferably at room temperature, for a period of about 6 to about 36 hours, more preferably, about 24 hours to obtain Tigecycline Form XI. The Tigecycline can then be dried if so desired.

Figure 10:
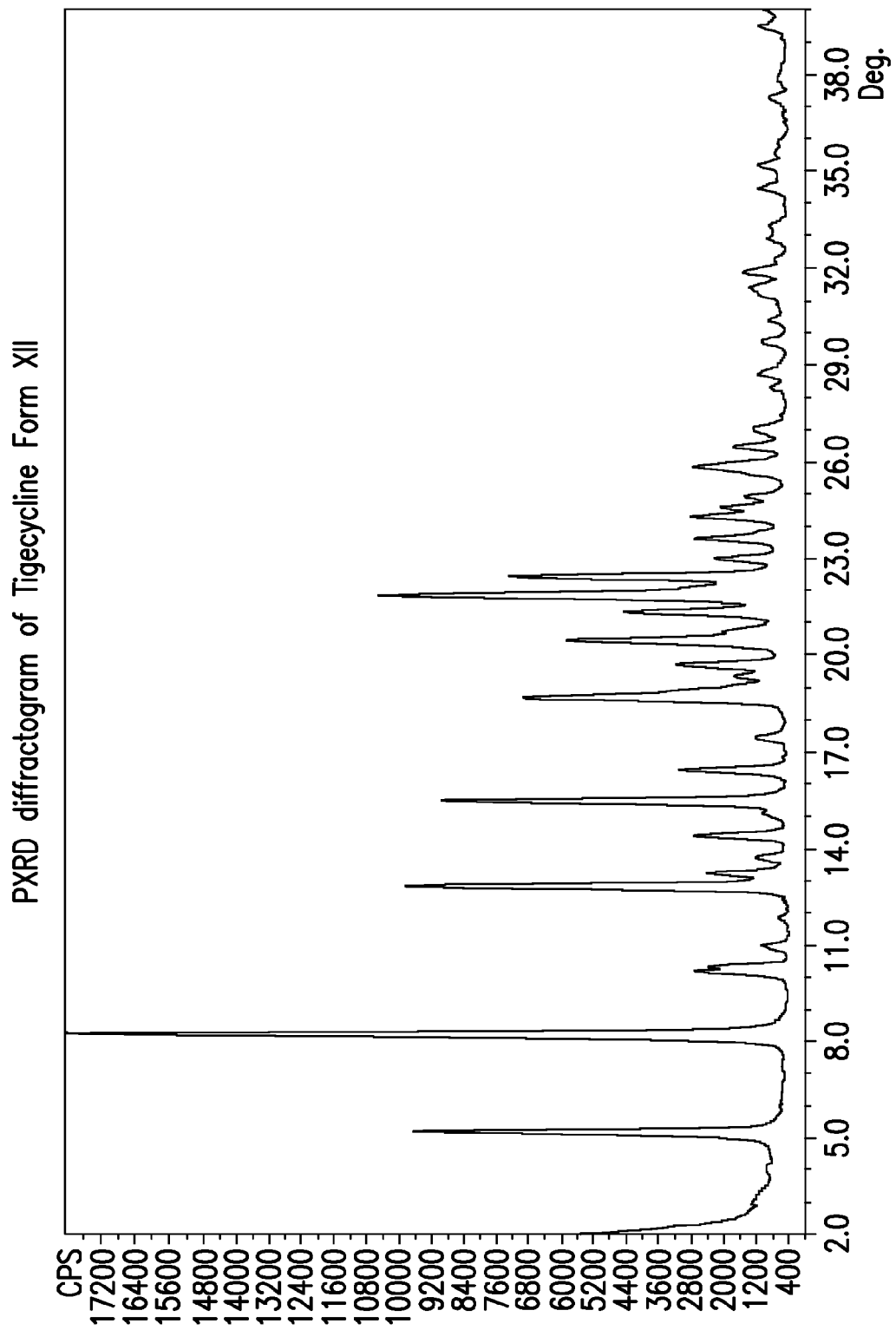
FIG. 10 illustrates a powder X-ray diffraction pattern for Tigecycline Form XII (as prepared by example 7).
Figure 38:
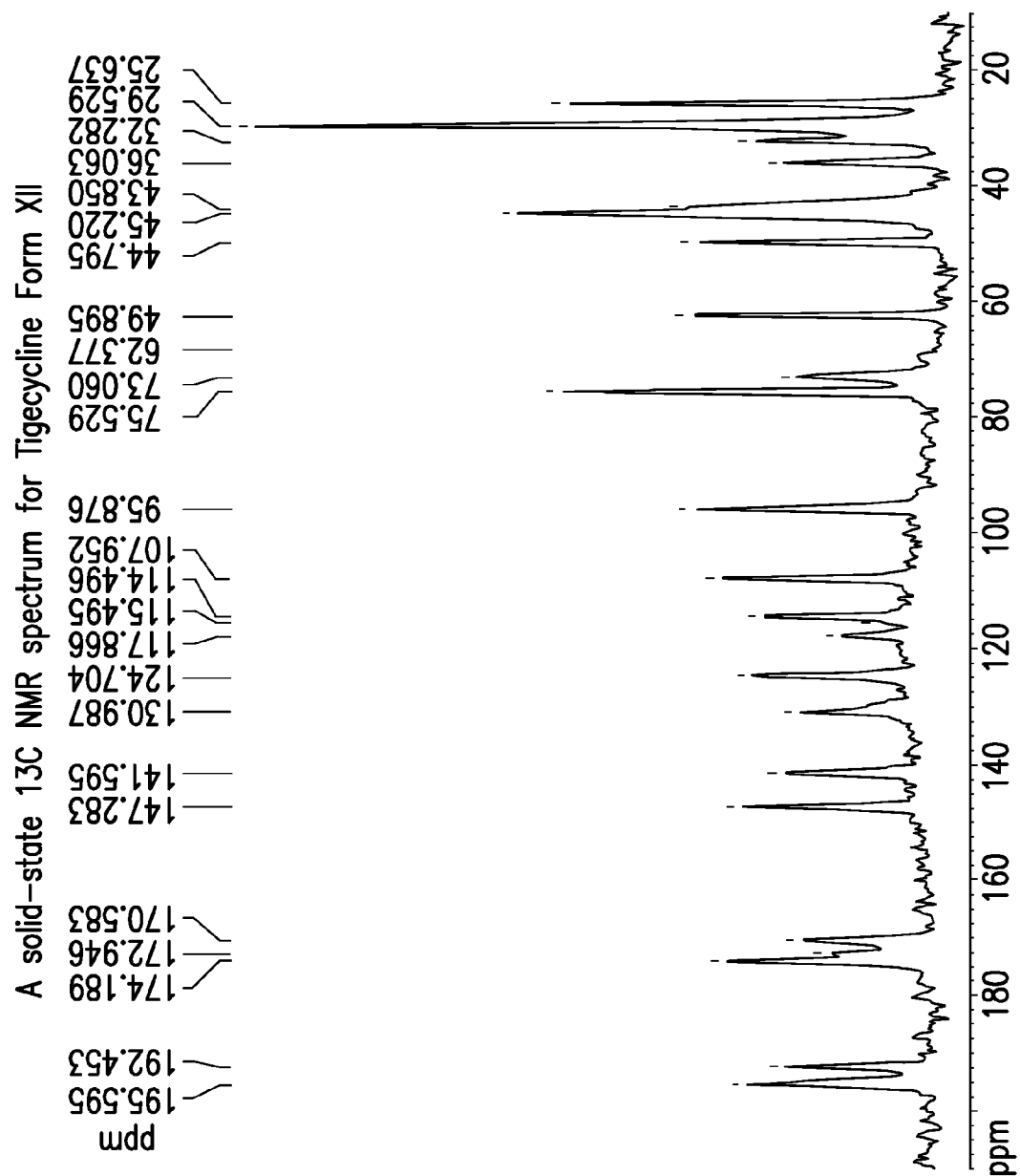
FIG. 38 illustrates a solid-state 13C NMR spectrum for Tigecycline Form XII.
Figure 39:
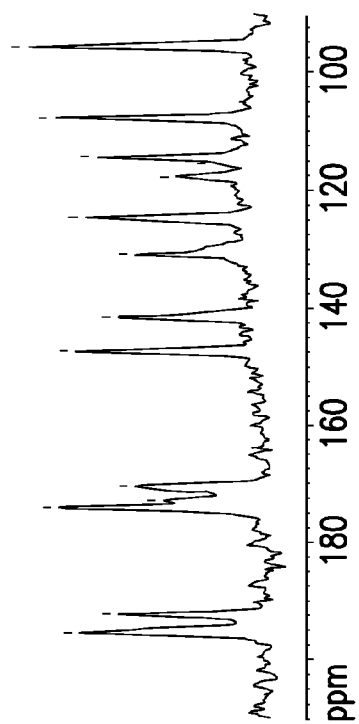
FIG. 39 illustrates a solid-state 13C NMR spectrum in the range of 90 to 210 ppm for Tigecycline Form XII.

The present invention provides yet another crystalline form of Tigecycline, designated Form XII, characterized by data selected from the group consisting of a powder XRD pattern with peaks at about 5.2, 8.2, 12.8 and 15.5±0.2 degrees two-theta; a powder XRD pattern with peaks at about 5.2, 8.2, 12.8, 15.5 and 20.4±0.2 degrees two-theta; a powder XRD pattern substantially as depicted in FIG. 10; a solid-state 13C NMR spectrum with signals at about 192.5, 174.2, 147.3, 131.0, and 114.5±0.2 ppm; a solid-state 13C NMR spectrum having chemical shift differences between the signal exhibiting the lowest chemical shift and another in the chemical shift range of 90 to 210 ppm of about 96.6, 78.3, 51.4, 35.1, and 18.6±0.1 ppm; a solid-state 13C NMR spectrum depicted in FIG. 38; and a solid-state 13C NMR spectrum depicted in FIG. 39. The signal exhibiting the lowest chemical shift in the chemical shift range of 90 to 210 ppm is, typically, at about 95.9±1 ppm. Form XII may be further characterized by powder XRD pattern with one or more peaks selected from the list consisting of about 18.7, and 21.8±0.2 degrees two-theta. Form XII typically has a weight loss, as measured by TGA, of between about 7.5-10.5% by weight, while it typically has water content, as measured by KF, of between about 1.0-2.5% by weight. Tigecycline Form XII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another aspect, Tigecycline Form XII may be prepared by providing a solution of Tigecycline and isopropanol and causing crystallization, preferably by cooling, to obtain Tigecycline Form XII which can then be recovered from the suspension. The alcohol may be in a volume ratio of about 10 to about 30 volumes, preferably about 20 volumes, relative to the weight of Tigecycline. Preferably, the solution is obtained by admixing hot isopropanol and Tigecycline. In this process the hot isopropanol is at temperature between room temperature and its reflux temperature, preferably at its reflux temperature. Preferably, cooling is at a temperature of about 30° C. to about −10° C., preferably about 0-5° C. Recovery of the crystal obtained is preferably by drying overnight in a vacuum at about 40° C.

Figure 11:
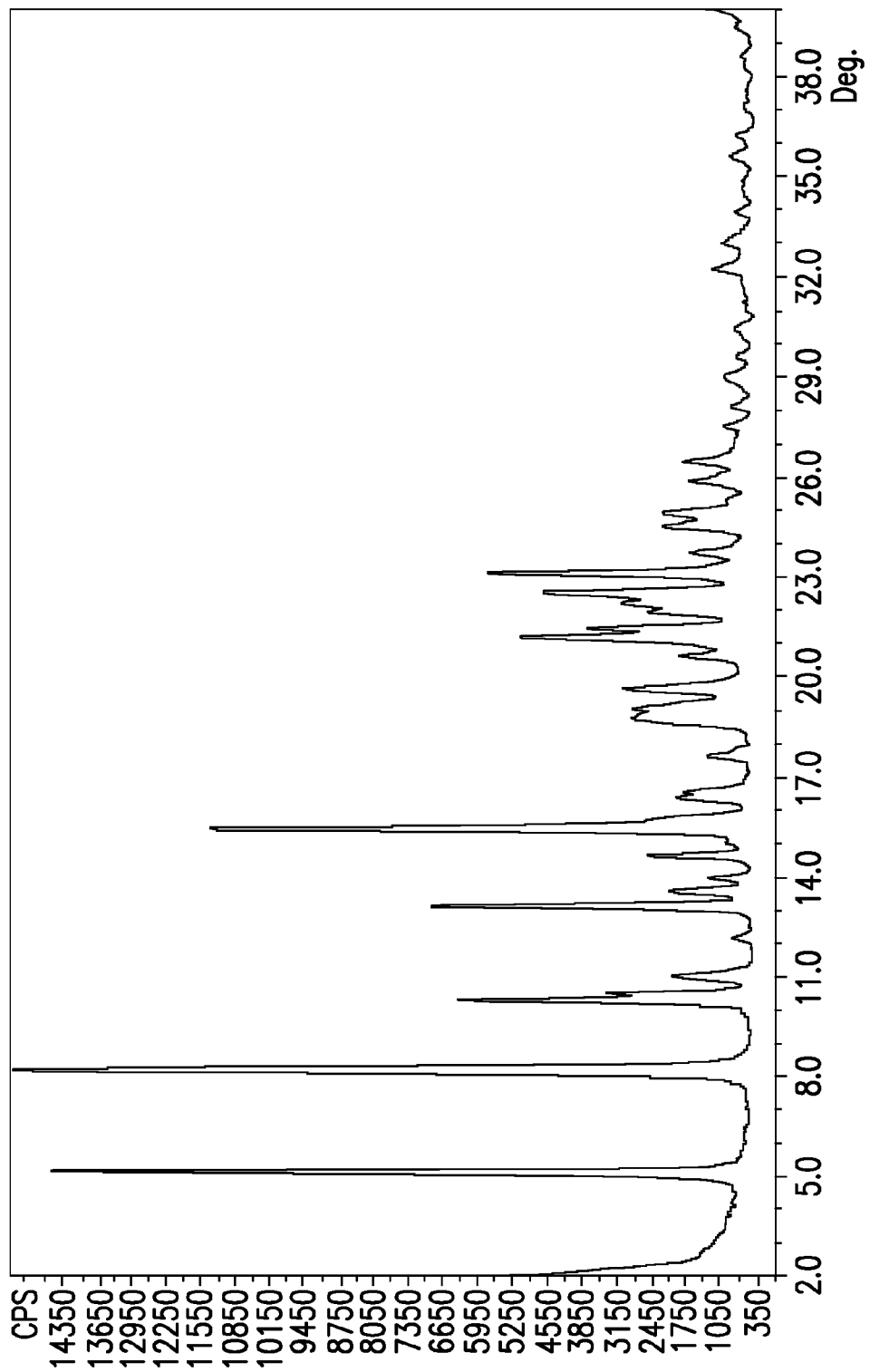
FIG. 11 illustrates a powder X-ray diffraction pattern for Tigecycline Form XIII (as prepared by example 8).
Figure 40:
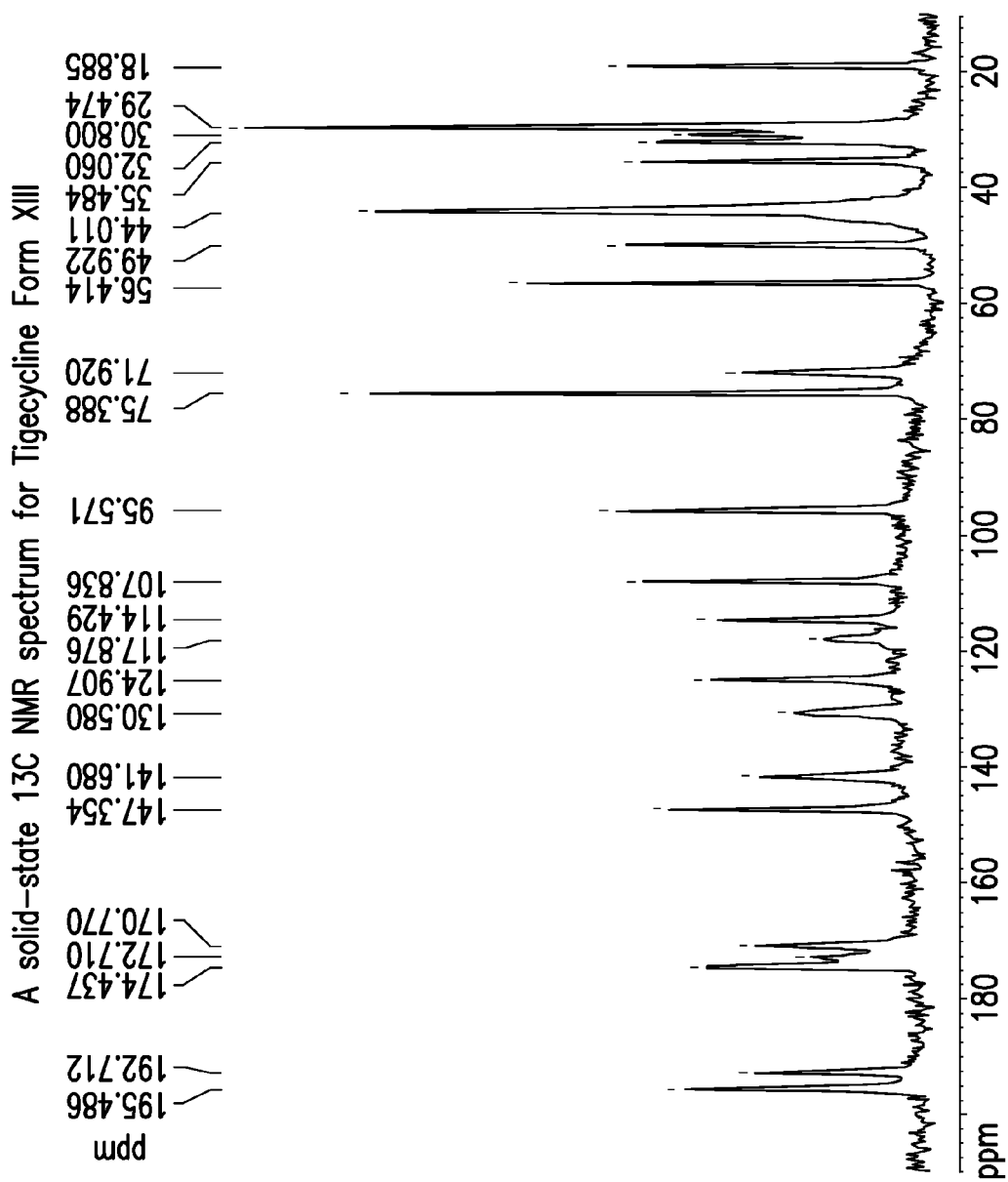
FIG. 40 illustrates a solid-state 13C NMR spectrum for Tigecycline Form XIII.
Figure 41:
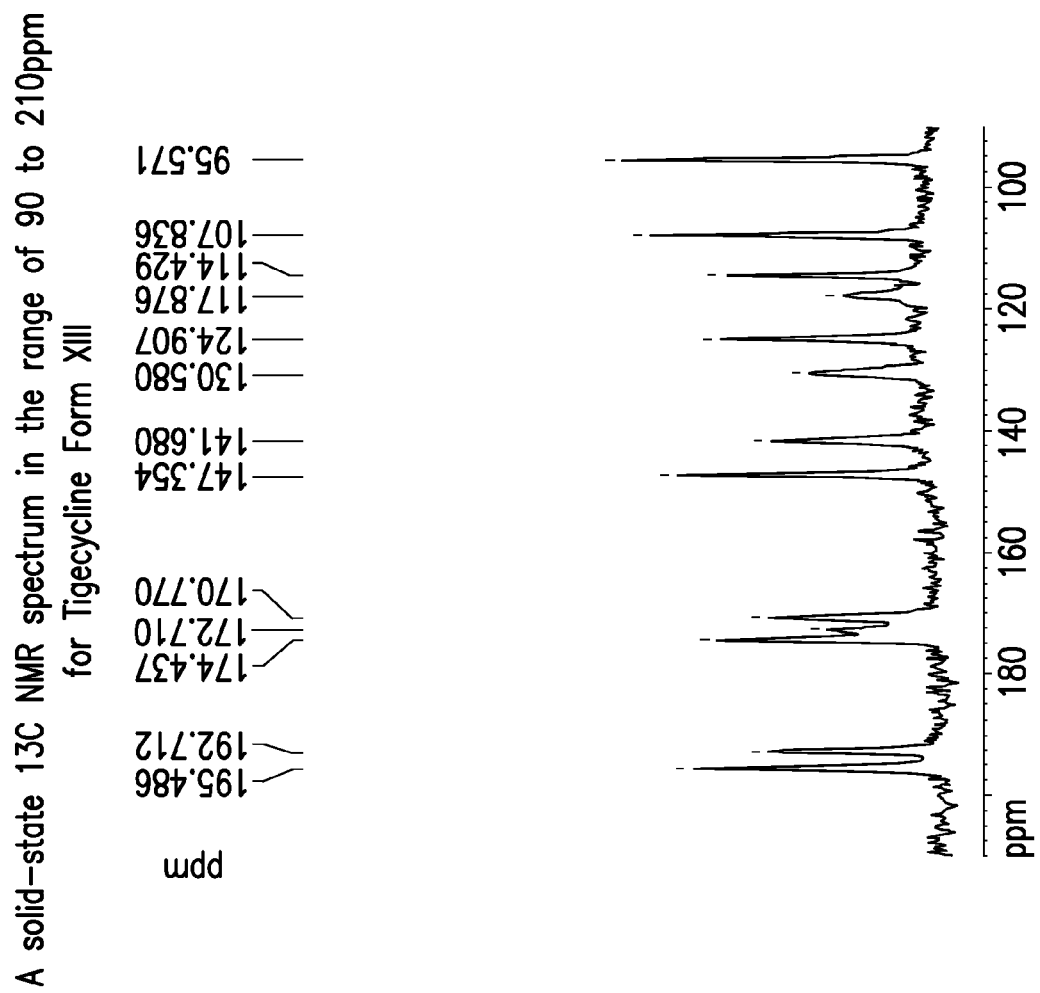
FIG. 41 illustrates a solid-state 13C NMR spectrum in the range of 90 to 210 ppm for Tigecycline Form XIII.

The present invention provides yet another crystalline form of Tigecycline, designated Form XIII, characterized by data selected from the group consisting of a powder XRD pattern with peaks at about 8.2, 16.4, 18.8 and 20.6±0.2 degrees two-theta; a powder XRD pattern substantially as depicted in FIG. 11; a solid-state 13C NMR spectrum with signals at about 192.7, 170.8, 130.6, 124.9, and 114.4±0.2 ppm; a solid-state 13C NMR spectrum having chemical shift differences between the signal exhibiting the lowest chemical shift and another in the chemical shift range of 90 to 210 ppm of about 97.1, 75.2, 35.0, 29.3, and 18.8±0.1 ppm; a solid-state 13C NMR spectrum depicted in FIG. 40; and a solid-state 13C NMR spectrum depicted in FIG. 41. The signal exhibiting the lowest chemical shift in the chemical shift range of 90 to 210 ppm is, typically, at about 95.6±1 ppm. Form XIII may be further characterized by powder XRD pattern with peaks at about 5.2, 10.3 and 15.4±0.2 degrees two-theta. Form XIII typically has a weight loss, as measured by TGA, of between about 6.0-8.0% by weight, while it typically has water content, as measured by KF, of between about 1.0-3.5% by weight. Tigecycline Form XIII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline Form XIII may be prepared by providing a solution of Tigecycline and ethanol or n-propanol and causing crystallization, preferably by cooling, to obtain Tigecycline Form XIII which can then be recovered from the suspension. The alcohol may be in a volume ratio of about 20 to about 50 volumes, preferably about 20 to about 40 volumes, more preferably about 40 volumes if ethanol is used or about 20 volumes when n-propanol is used, relative to the weight of Tigecycline. Preferably, the solution is obtained by admixing hot ethanol and Tigecycline. In this process the hot ethanol is at temperature between room temperature and its reflux temperature, preferably at its reflux temperature. Preferably, cooling is at a temperature of about 30° C. to about −10° C., preferably about 0-5° C. Recovery of the crystal obtained is preferably by drying overnight in a vacuum at about 40° C.

In another aspect, the present invention further provides a process for the preparation of Tigecycline form XV comprising maintaining at about room temperature solid Tigecycline Form III for example as prepared according to U.S. Pat. No. 5,675,030 under acetonitrile atmosphere for a period of about 5 to 10 days, preferably about 7 days. The Tigecycline form XV may also be prepared by providing a mixture of Tigecycline prepared according to U.S. Pat. No. 5,675,030 and about 10 to about 30 volumes, preferably about 20 volumes, of ice cold acetonitrile; and maintaining the mixture at a temperature of about −5° C. to about 5° C. for a period of about 30 minutes to about 4 hours, preferably about 1 hour. Form XV may be prepared by a process similar to the ones described in examples 9 or 10.

In another embodiment, the present invention further provides a process for the preparation of Tigecycline form XVII comprising dissolving Tigecycline in water; adjusting the pH of the obtained solution to about 7 to about 8, preferably from about 7.2 to about 7.4 and adding THF; extracting with dichloromethane (DCM); drying the organic extract to obtain a suspension of Tigecycline; and filtering and washing the suspension with heptane. Form XVII may be prepared by a process similar to the ones described in example 11.

Figure 14:
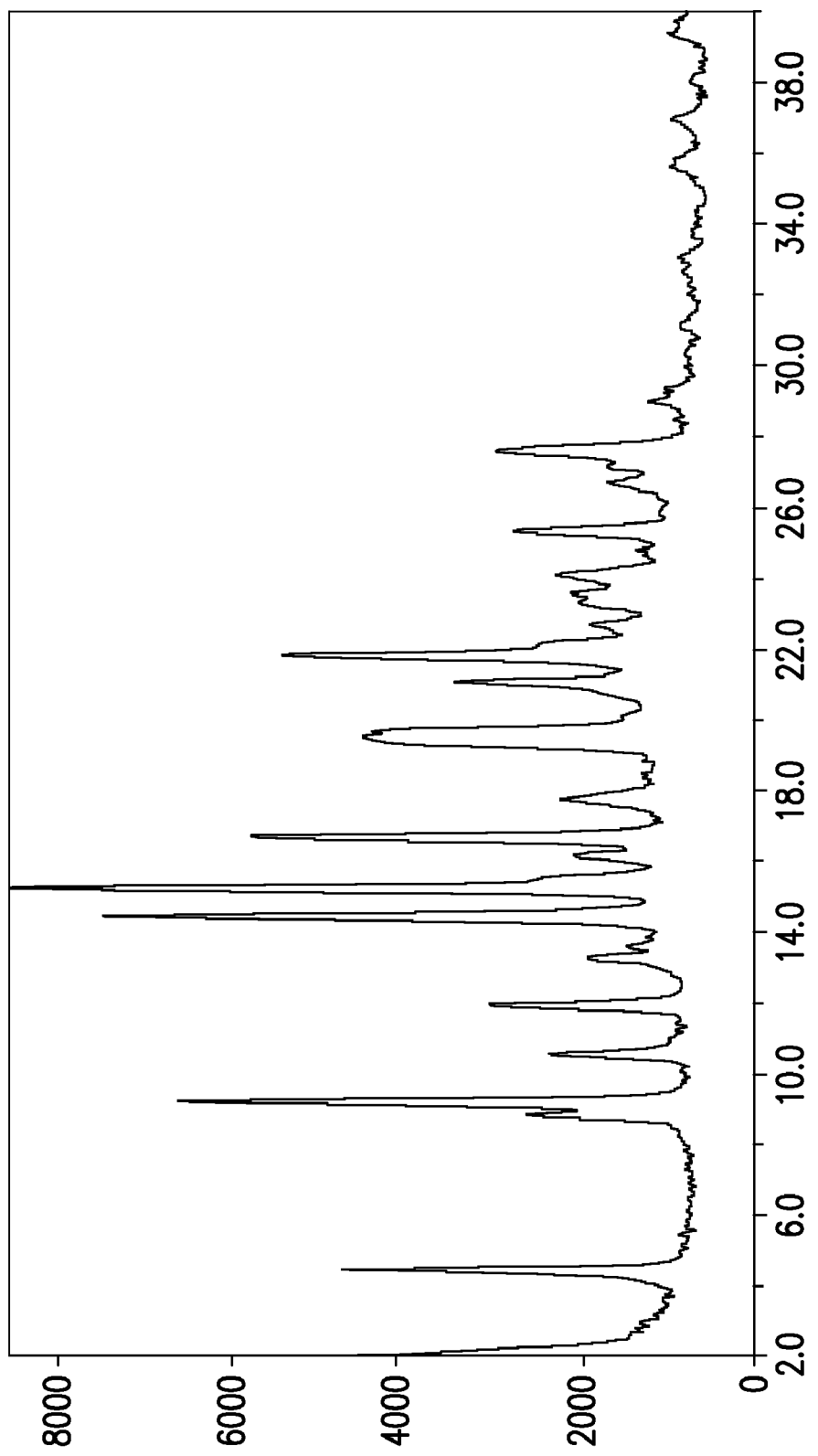
FIG. 14 illustrates a powder X-ray diffraction pattern for Tigecycline Form XVIII (as prepared by example 12).
Figure 42:
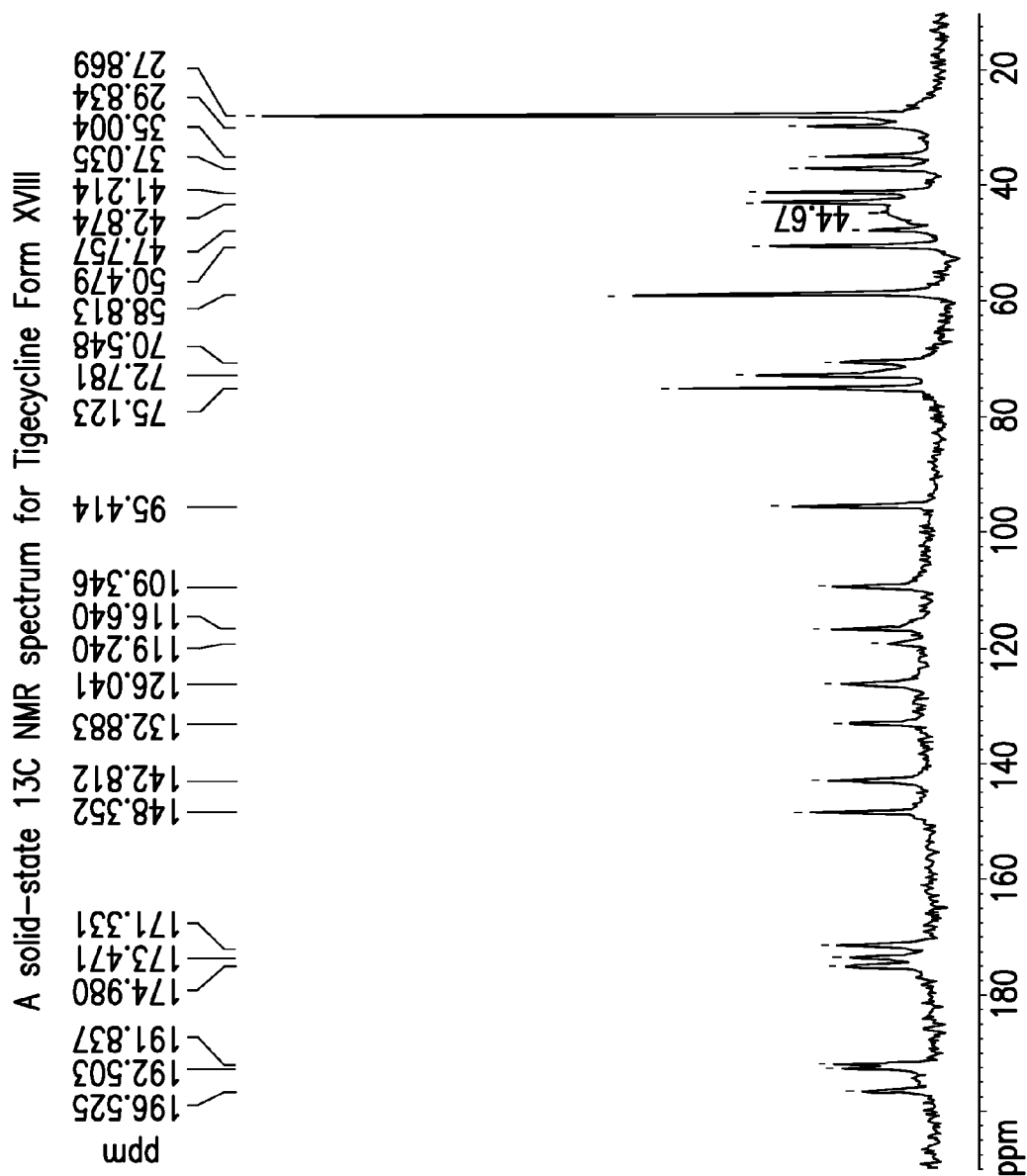
FIG. 42 illustrates a solid-state 13C NMR spectrum for Tigecycline Form XVIII.
Figure 43:
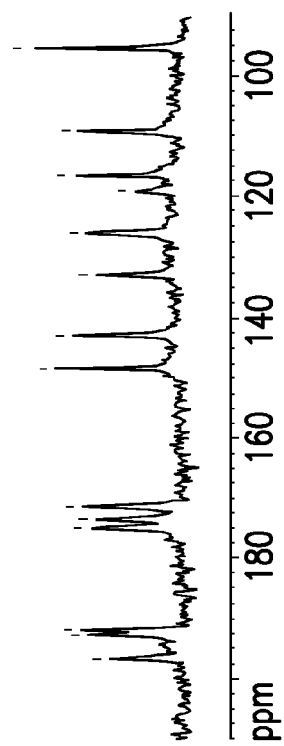
FIG. 43 illustrates a solid-state 13C NMR spectrum in the range of 90 to 210 ppm for Tigecycline Form XVIII

The present invention provides yet another crystalline form of Tigecycline, designated Form XVIII, characterized by data selected from the group consisting of a powder XRD pattern with peaks at about 9.2, 14.4, 15.2 and 16.7±0.2 degrees two-theta; a powder XRD pattern with peaks at about 4.4, 9.2, 14.4, 15.2 and 16.7±0.2 degrees two-theta; a powder XRD pattern substantially as depicted in FIG. 14; a solid-state 13C NMR spectrum with signals at about 175.0, 148.4, 142.8, 126.0, and 109.3±0.2 ppm; a solid-state 13C NMR spectrum having chemical shift differences between the signal exhibiting the lowest chemical shift and another in the chemical shift range of 90 to 210 ppm of about 79.6, 53.0, 47.4, 30.6, and 13.9±0.1 ppm; a solid-state 13C NMR spectrum depicted in FIG. 42; and a solid-state 13C NMR spectrum depicted in FIG. 43. The signal exhibiting the lowest chemical shift in the chemical shift range of 90 to 210 ppm is, typically, at about 95.4±1 ppm. Form XVIII may be further characterized by powder XRD pattern with one or more peaks selected from the list consisting of about 10.5, 11.9, 17.8 and 19.5±0.2 degrees two-theta. Form XVIII typically has a weight loss, as measured by TGA, of between about 10.0-12.5% by weight, while it typically has water content, as measured by KF, of between about 1.0-5.0% by weight. Tigecycline Form XVIII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XVIII may be prepared by dissolving Tigecycline in water, preferably DDW; adjusting the pH of the obtained solution to about 7 to about 8, preferably from about 7.2 to about 7.4 and adding a $C_{4-7}$ cyclic ether, preferably THF; extracting with dichloromethane (DCM); drying the organic extract to obtain a suspension of Tigecycline; filtering and washing the suspension with DCM to obtain an initial filtrate; concentrating the initial filtrate; and cooling the concentrated initial filtrate to obtain Tigecycline form XVIII. Preferably cooling comprises stirring the concentrated initial filtrate for about 15 minutes to about 2 hours, more preferably for about 30 minutes, to a temperature of about −5° C. to about 10° C., more preferably to about 0-5° C. Form XVIII may be prepared by a process similar to the one described in example 12.

Figure 15:
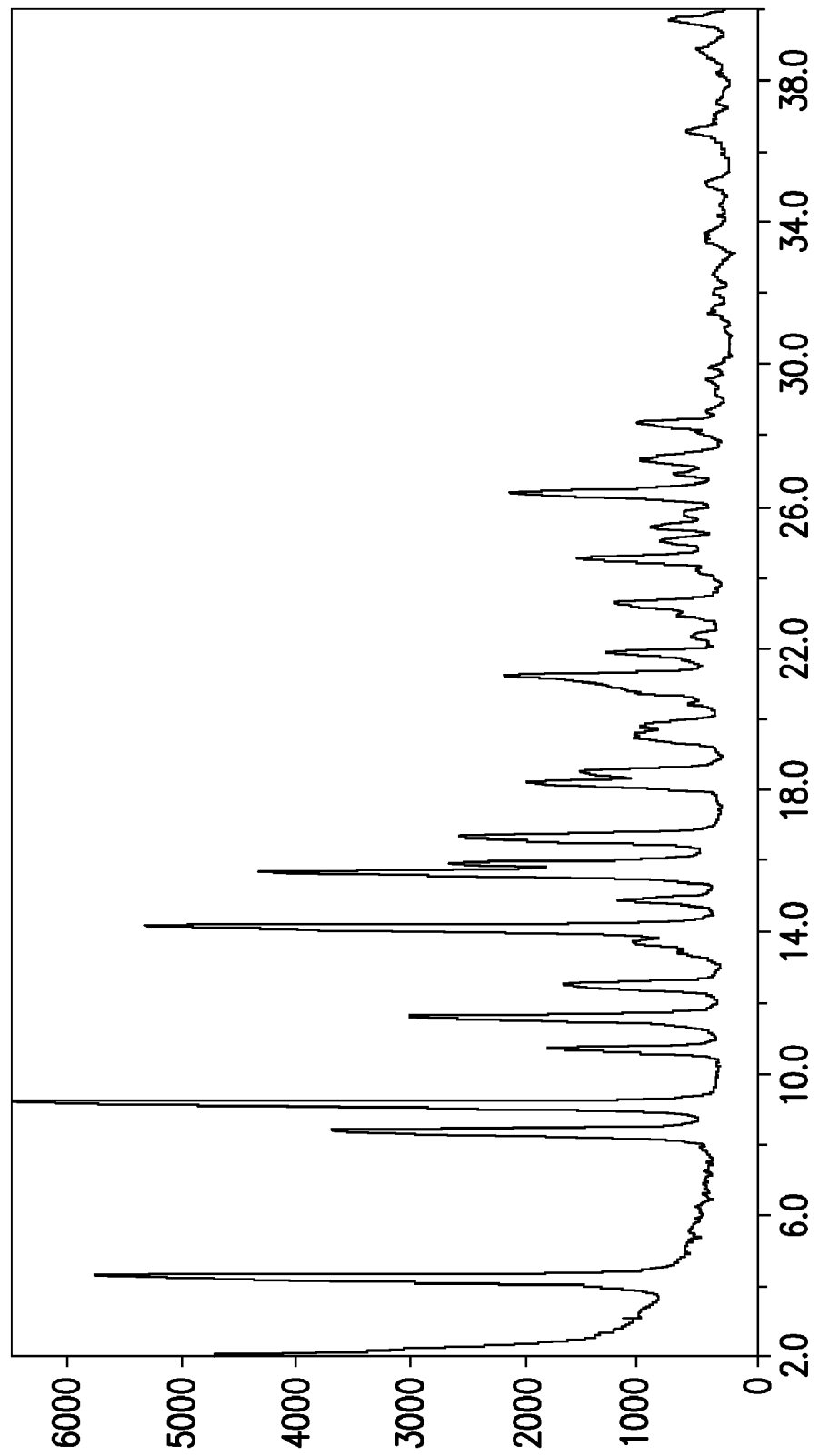
FIG. 15 illustrates a powder X-ray diffraction pattern for Tigecycline Form XIX (as prepared by example 13).

The present invention provides yet another crystalline form of Tigecycline, designated Form XIX, characterized by data selected from the group consisting of a powder XRD pattern with peaks at about 8.4, 9.1, 14.1 and 15.7±0.2 degrees two-theta; and a powder XRD pattern substantially as depicted in FIG. 15. Form XIX may be further characterized by powder XRD pattern with one or more peaks selected from the list consisting of about 4.3, 10.7, 11.6, 12.5, 16.6 and 18.2±0.2 degrees two-theta. Tigecycline Form XIX is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XIX may be prepared by a process comprising providing a solution of Tigecycline in dichloromethane (DCM) and reducing the volume of the solution, preferably by drying over a desiccant; adding a $C_{5-8}$ aromatic hydrocarbon, preferably toluene, preferably in an amount to obtain a total volume about 1 to about 6, preferably 1.5 times the volume of the original solution; partially evaporating the solvent from the solution to obtain a suspension and filtering the suspension. Form XIX may be prepared by a process similar to the one described in example 13.

Figure 16:
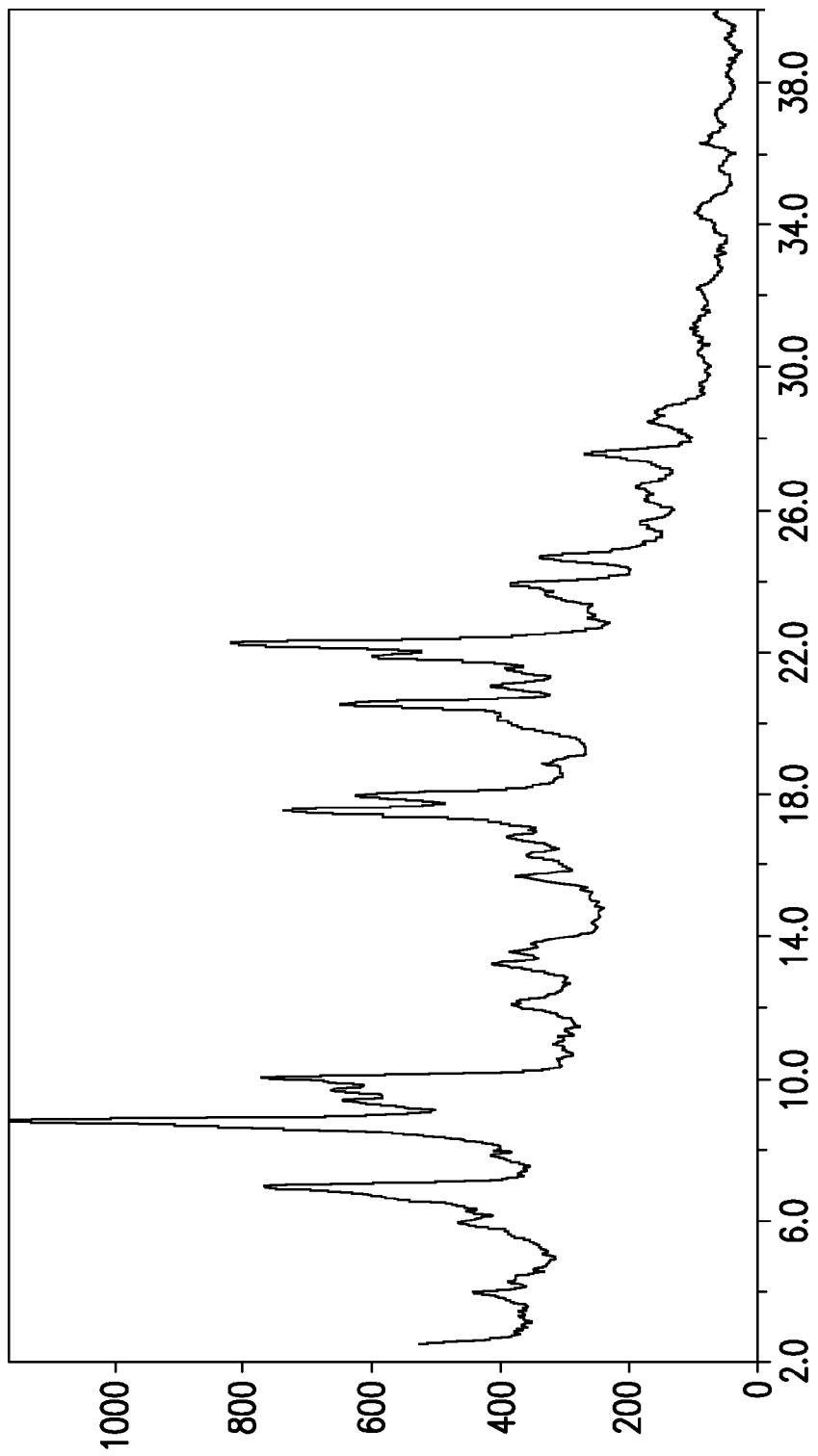
FIG. 16 illustrates a powder X-ray diffraction pattern for Tigecycline Form XX (as prepared by example 14).

The present invention provides yet another crystalline form of Tigecycline, designated Form XX, characterized by data selected from the group consisting of a powder XRD pattern with peaks at about 7.0, 8.8, 10.0 and 17.5±0.2 degrees two-theta; and a powder XRD pattern substantially as depicted in FIG. 16. Form XX may be further characterized by powder XRD pattern with peaks at about 17.9 and 20.5±0.2 degrees two-theta. Tigecycline Form XX is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XX may be prepared by a process comprising providing a solution of Tigecycline in dichloromethane (DCM) and reducing the volume of the solution, preferably by drying over a desiccant; adding a $C_{4-10}$ ether, preferably di-n-butyl ether, preferably in an amount to obtain a total volume about 1 to about 6, more preferably about 1.5 times the of the original solution; partially evaporating the solvent from the solution to obtain a suspension; filtering the suspension and washing the filtrate with di-n-butyl ether to obtain form VIII; maintain the Tigecycline form VIII at about room temperature for a period of about 6 to about 16 hours, preferably for about 12 hours; and filter the material from the previous step. Form XX may be prepared by a process similar to the one described in example 14.

In another embodiment, the present invention further provides a process for the preparation of Tigecycline form XXI comprising providing a solution of Tigecycline in DCM and reducing the volume of the solution to a concentration of about 10-20 mL/g of product, preferably by drying over a desiccant; adding ethyl acetate or acetonitrile, preferably in an amount to obtain a total volume about 1 to about 6, more preferably about 1.15 times the volume of the original solution; partially evaporating the solvent from the solution to obtain a suspension, preferably to about half its original volume; stirring the suspension at a temperature of about −5° C. to about 10° C., preferably about 0-5° C. for about 15 minutes to about 4 hours, preferably 15 minutes to about 2 hours, preferably for about 30 minutes; recovering the product, for example by filtration; maintaining the product at a temperature of about 0 to about 15° C. for about 14 to about 60 hours; and drying the recovered product, preferably at about 60° C. under reduced pressure for about 6 to about 24 hours, preferably about 12 hours to obtain form XXI. Form XXI may be prepared by a process similar to the one described in examples 15 and 16.

Figure 18:
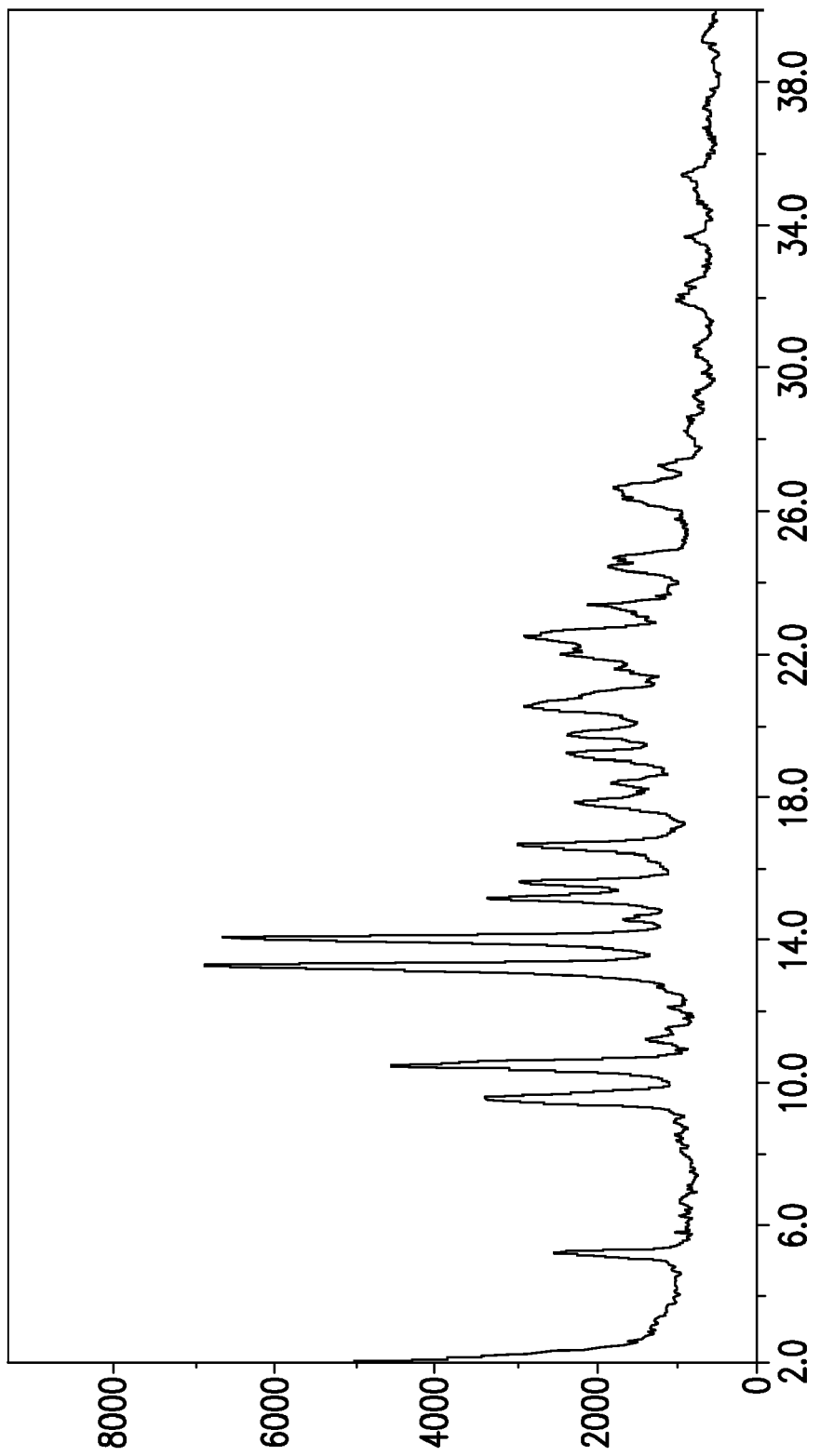
FIG. 18 illustrates a powder X-ray diffraction pattern for Tigecycline Form XXII (as prepared by example 16).

The present invention provides yet another crystalline form of Tigecycline, designated Form XXII, characterized by data selected from the group consisting of a powder XRD pattern with peaks at about 9.5, 10.4, 13.2 and 14.0±0.2 degrees two-theta; a powder XRD pattern with peaks at about 9.5, 10.4, 13.2, 14.0, 15.1 and 16.7±0.2 degrees two-theta; and a powder XRD pattern substantially as depicted in FIG. 18. Form XXII may be further characterized by powder XRD pattern with one or more peaks selected from the list consisting of about 5.2, 15.6, and 17.9±0.2 degrees two-theta. Tigecycline Form XXII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XXII may be prepared by a process comprising providing Tigecyline form IX; and maintain form IX of Tigecycline for a period of about 5 to about 10 days, preferably for about 7 days, under 100% RH (relative humidity) at about room temperature. Form XXII may be prepared by a process similar to the one described in example 17.

Figure 19:
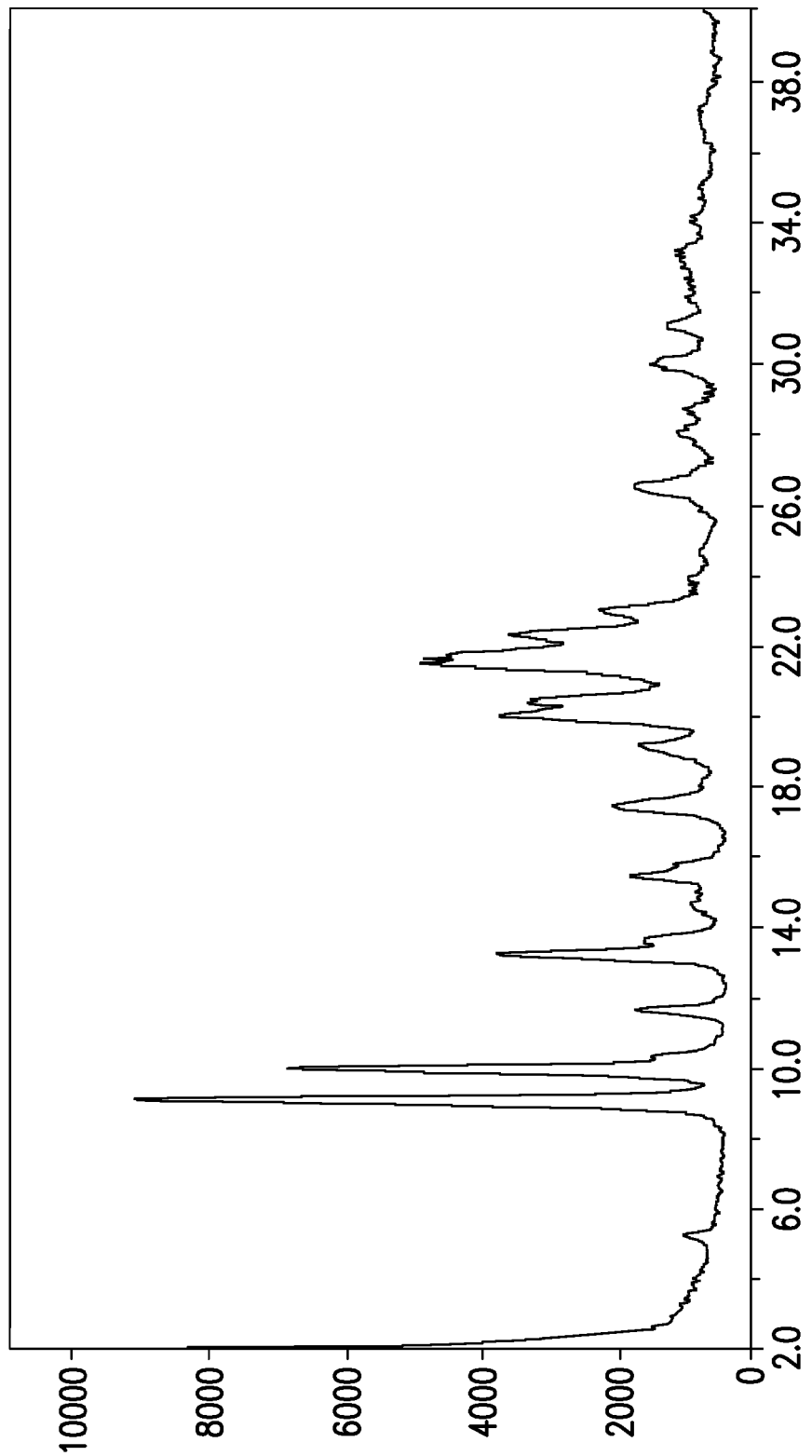
FIG. 19 illustrates a powder X-ray diffraction pattern for Tigecycline Form XXIII (as prepared by example 17).

The present invention provides yet another crystalline form of Tigecycline, designated Form XXIII, characterized by data selected from the group consisting of a powder XRD pattern with peaks at about 9.1, 10.0, 13.3 and 17.4±0.2 degrees two-theta; a powder XRD pattern with peaks at about 9.1, 10.0, 13.3, 17.4 and 19.2±0.2 degrees two-theta; and a powder XRD pattern as depicted in FIG. 19. Form XXIII may be further characterized by powder XRD pattern with one or more peaks selected from the list consisting of about 11.6, 15.5 and 20.0±0.2 degrees two-theta. Tigecycline Form XXII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XXIII may be prepared by a process comprising providing Tigecyline form VII; and maintain form VII of Tigecycline for a period of about 5 to about 10 days, preferably for about 7 days, under 0% RH (relative humidity) at about room temperature. Form XXIII may be prepared by a process similar to the one described in example 18.

Figure 20:
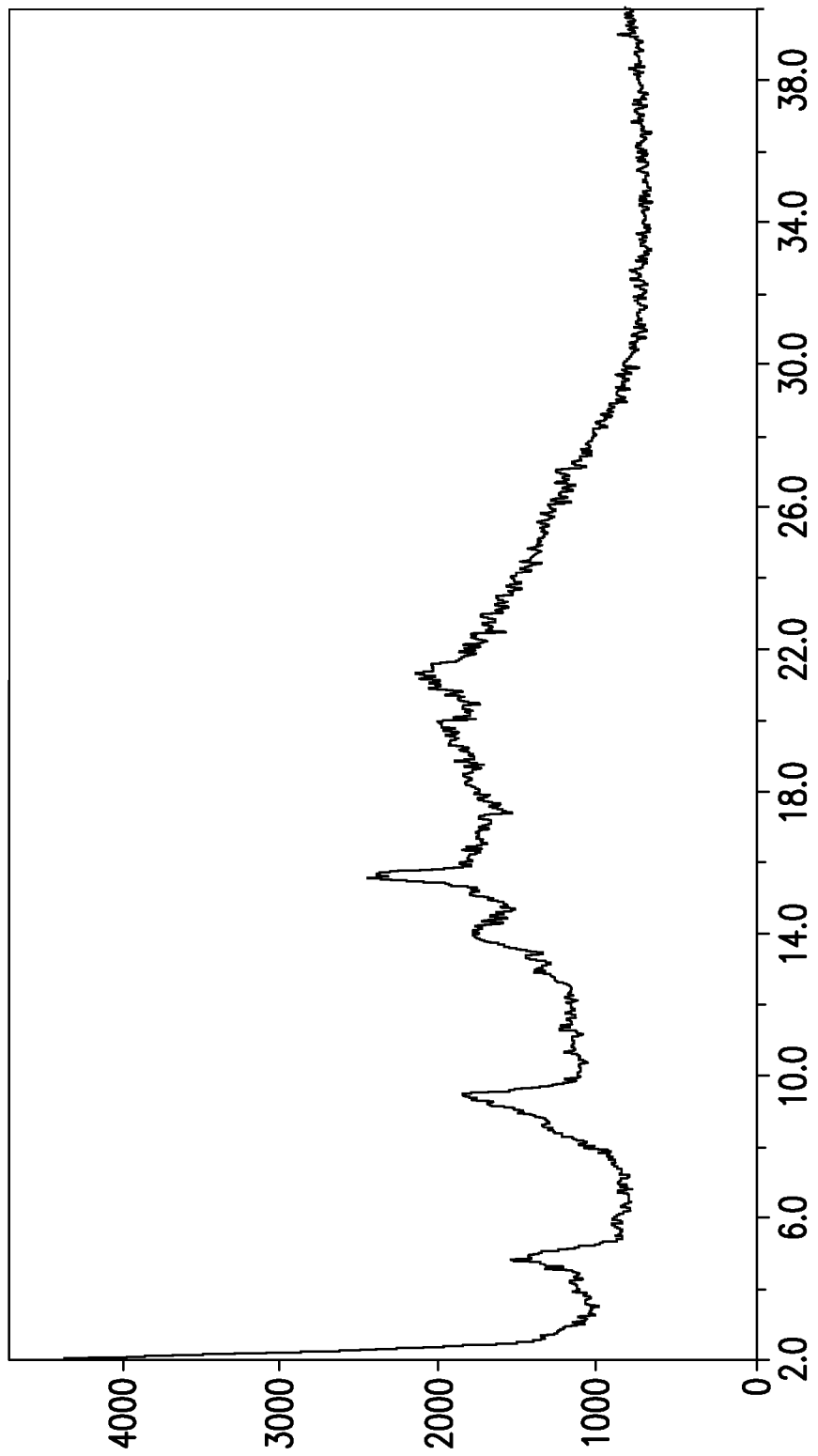
FIG. 20 illustrates a powder X-ray diffraction pattern for Tigecycline Form XXIV (as prepared by example 18).
Figure 44:
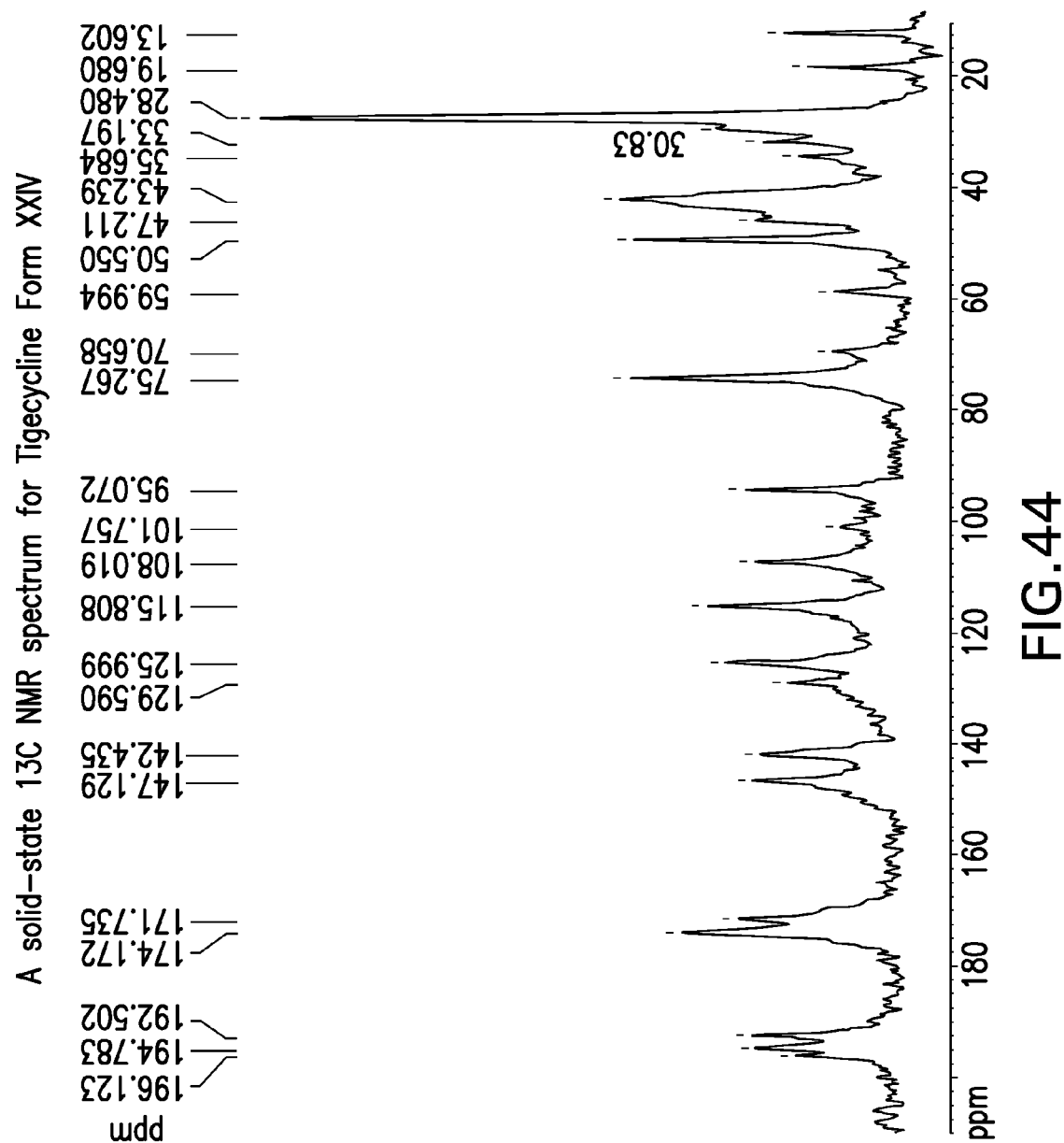
FIG. 44 illustrates a solid-state 13C NMR spectrum for Tigecycline Form XXIV.
Figure 45:
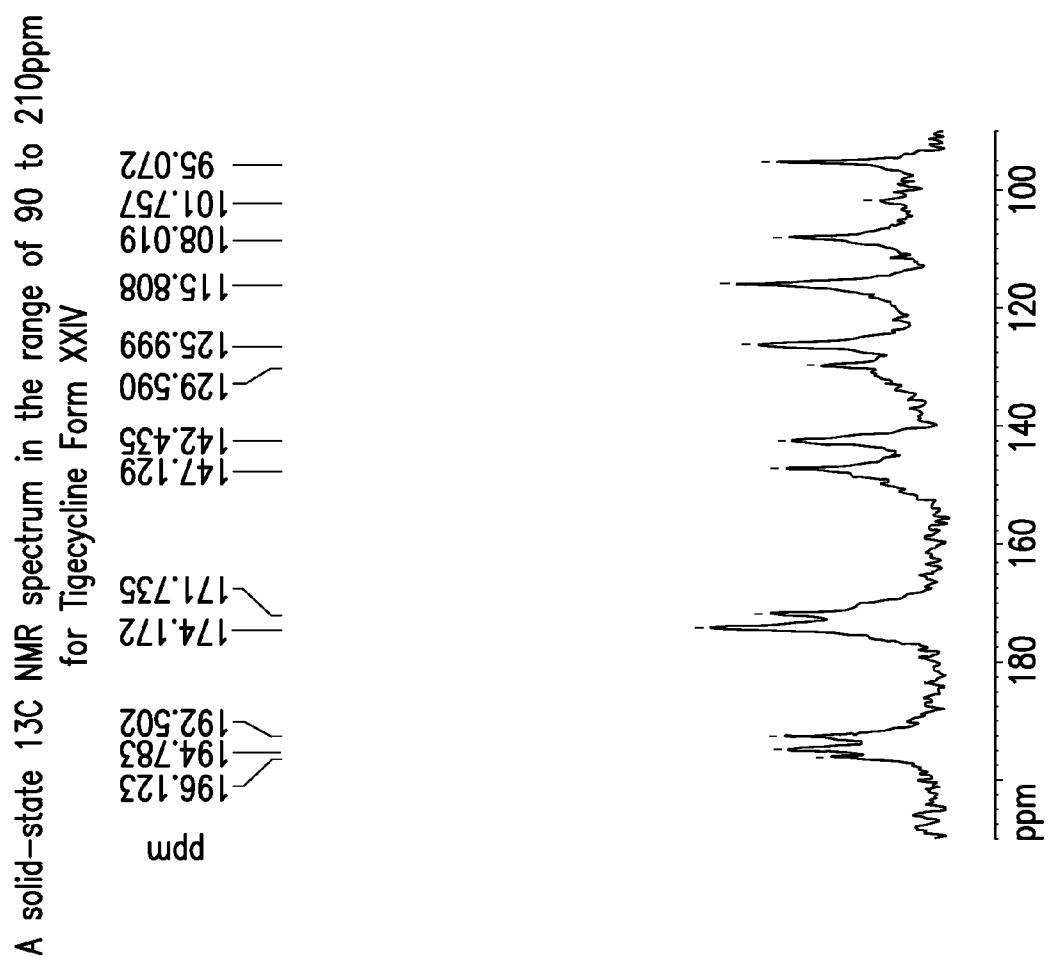
FIG. 45 illustrates a solid-state 13C NMR spectrum in the range of 90 to 210 ppm for Tigecycline Form XXIV

The present invention provides yet another crystalline form of Tigecycline, designated Form XXIV, characterized by data selected from the group consisting of a powder XRD pattern with peaks at about 4.8, 9.5, 14.0 and 15.6±0.2 degrees two-theta; a powder XRD pattern with peaks at about 4.8, 8.4, 9.5, 14.0 and 15.6±0.2 degrees two-theta; a powder XRD pattern substantially as depicted in FIG. 20; a solid-state 13C NMR spectrum with signals at about 194.8, 174.2, 142.4, 129.6, and 126.0±0.2 ppm; a solid-state 13C NMR spectrum having chemical shift differences between the signal exhibiting the lowest chemical shift and another in the chemical shift range of 90 to 210 ppm of about 99.7, 79.1, 47.3, 34.5, and 30.9±0.1 ppm; a solid-state 13C NMR spectrum depicted in FIG. 44; and a solid-state 13C NMR spectrum depicted in FIG. 45. The signal exhibiting the lowest chemical shift in the chemical shift range of 90 to 210 ppm is, typically, at about 95.1±1 ppm. Form XXIV may be further characterized by powder XRD pattern with one or more peaks selected from the list consisting of about 19.9, and 21.3±0.2 degrees two-theta. Form XXIV typically has a weight loss, as measured by TGA, of between about 1.5-8.0% by weight, while it typically has water content, as measured by KF, of between about 1.5-4.5% by weight. Tigecycline Form XXIV is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XXIV may be prepared by a process comprising providing a Tigecycline Form I; and drying, preferably at about 60° C. under reduced pressure for about 6 to about 24 hours, preferably about 12 hours.

In another embodiment, Tigecycline form XXIV may be prepared by a process comprising providing a solution of Tigecycline in dichloromethane (DCM); drying and filtering the solution; adding ethylacetate or methyacetate; concentrating the resulting mixture to about 5 to about 40 mL/mg, preferably 10-20 mL/g product; admixing ethylacetate or methylacetate to the concentrate to obtain a suspension; concentrating the suspension and cooling the suspension for about 15 minutes to about 2 hours, preferably 30 minutes, at a temperature of about −5° C. to about 10° C., preferably to about 0-5° C.; and drying the recovered product, preferably at about 60° C. under reduced pressure for about 6 to about 24 hours, preferably about 12 hours. Form XXIV may be prepared by a process similar to the one described in example 19.

Figure 21:
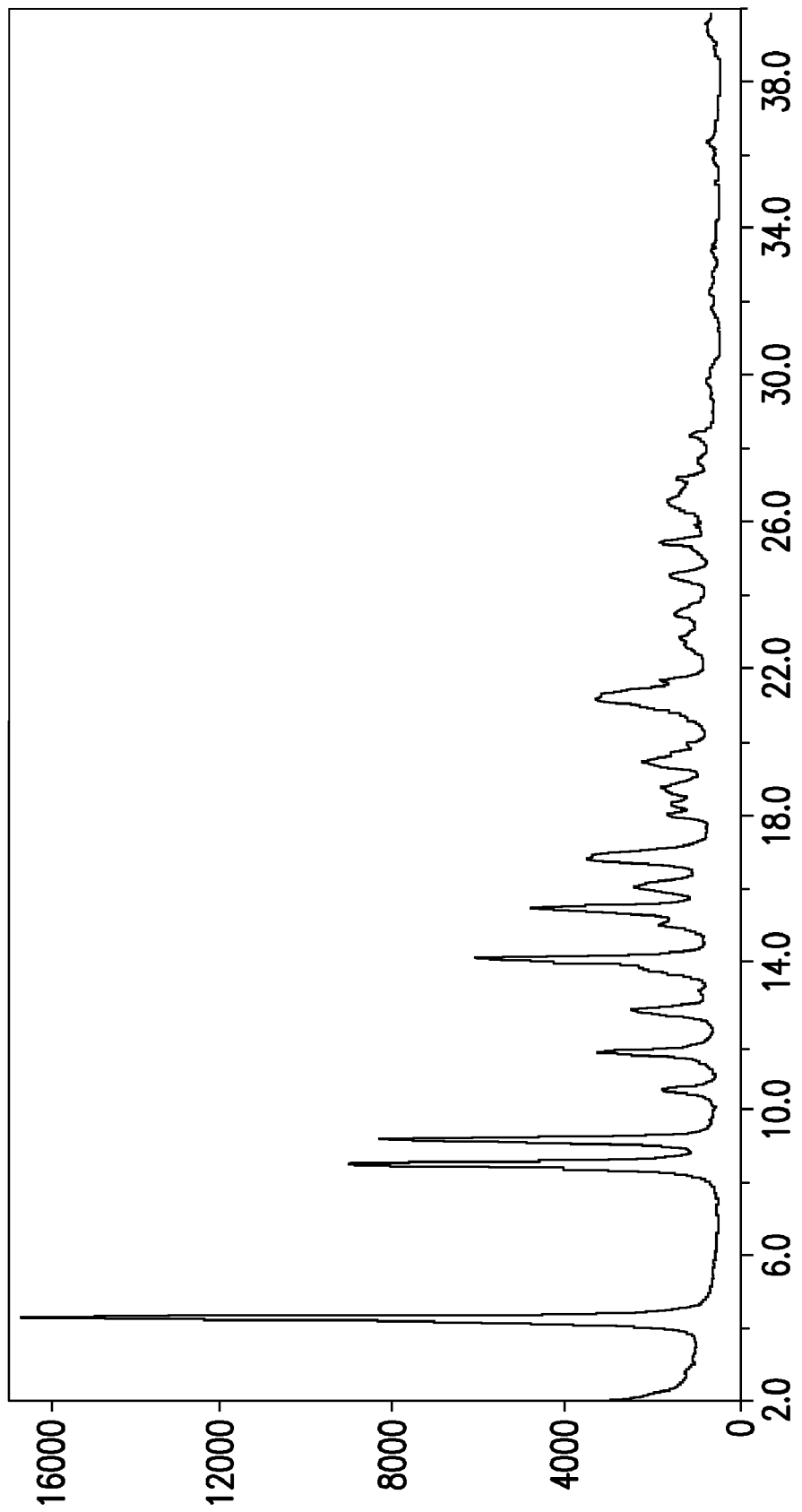
FIG. 21 illustrates a powder X-ray diffraction pattern for Tigecycline Form XXV (as prepared by example 21).
Figure 46:
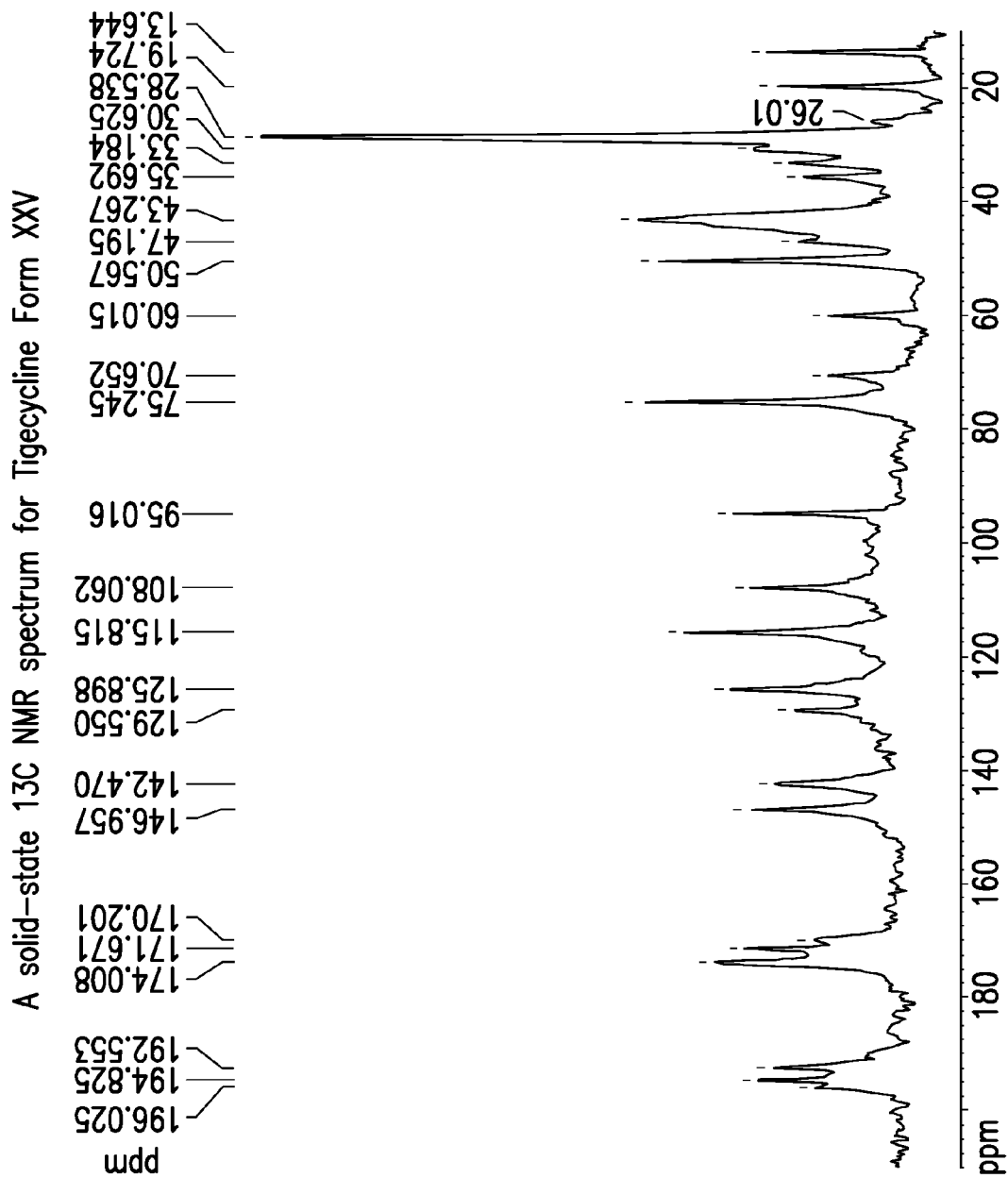
FIG. 46 illustrates a solid-state 13C NMR spectrum for Tigecycline Form XXV.

The present invention provides another crystalline form of Tigecycline, designated Form XXV, characterized by data selected from the group consisting of a powder XRD pattern with peaks at about 8.5, 12.7, 16.1 and 16.8±0.2 degrees two-theta; a powder XRD pattern with peaks at about 4.3, 8.5, 10.5, 12.7, 16.1 and 16.8±0.2 degrees two-theta; a powder XRD pattern substantially as described in FIG. 21; a solid-state 13C NMR spectrum with signals at about 196.0, 194.8, 192.6, 174.0, and 142.5±0.2 ppm; a solid-state 13C NMR spectrum having chemical shift differences between the signal exhibiting the lowest chemical shift and another in the chemical shift range of 90 to 210 ppm of about 101.0, 99.8, 97.6, 79.0, and 47.5±0.1 ppm; a solid-state 13C NMR spectrum depicted in FIG. 46; and a solid-state 13C NMR spectrum depicted in FIG. 47. The signal exhibiting the lowest chemical shift in the chemical shift range of 90 to 210 ppm is, typically, at about 95.0±1 ppm. Form XXV may be further characterized by powder XRD pattern with one or more peaks selected from the list consisting of about 14.1, 15.0, 18.7, 19.4 and 21.2±0.2 degrees two-theta. Form XXV typically has a weight loss, as measured by TGA, of between about 9.0-10.0% by weight, while it typically has water content, as measured by KF, of between about 1.0-2.0% by weight. Form XXV may be an ethyl acetate solvate. Tigecycline Form XXV is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

The present invention provides a process for preparing crystalline form XXV of Tigecycline by exposing crystalline Form I of Tigecycline in about 0% to about 20% relative humidity at a temperature of about 15° C. to about 30° C. for about 1 day to about 7 days. Preferably, the process comprises exposing crystalline Form I to about 0% relative humidity at a temperature of about ambient temperature for 7 days.

Figure 22:
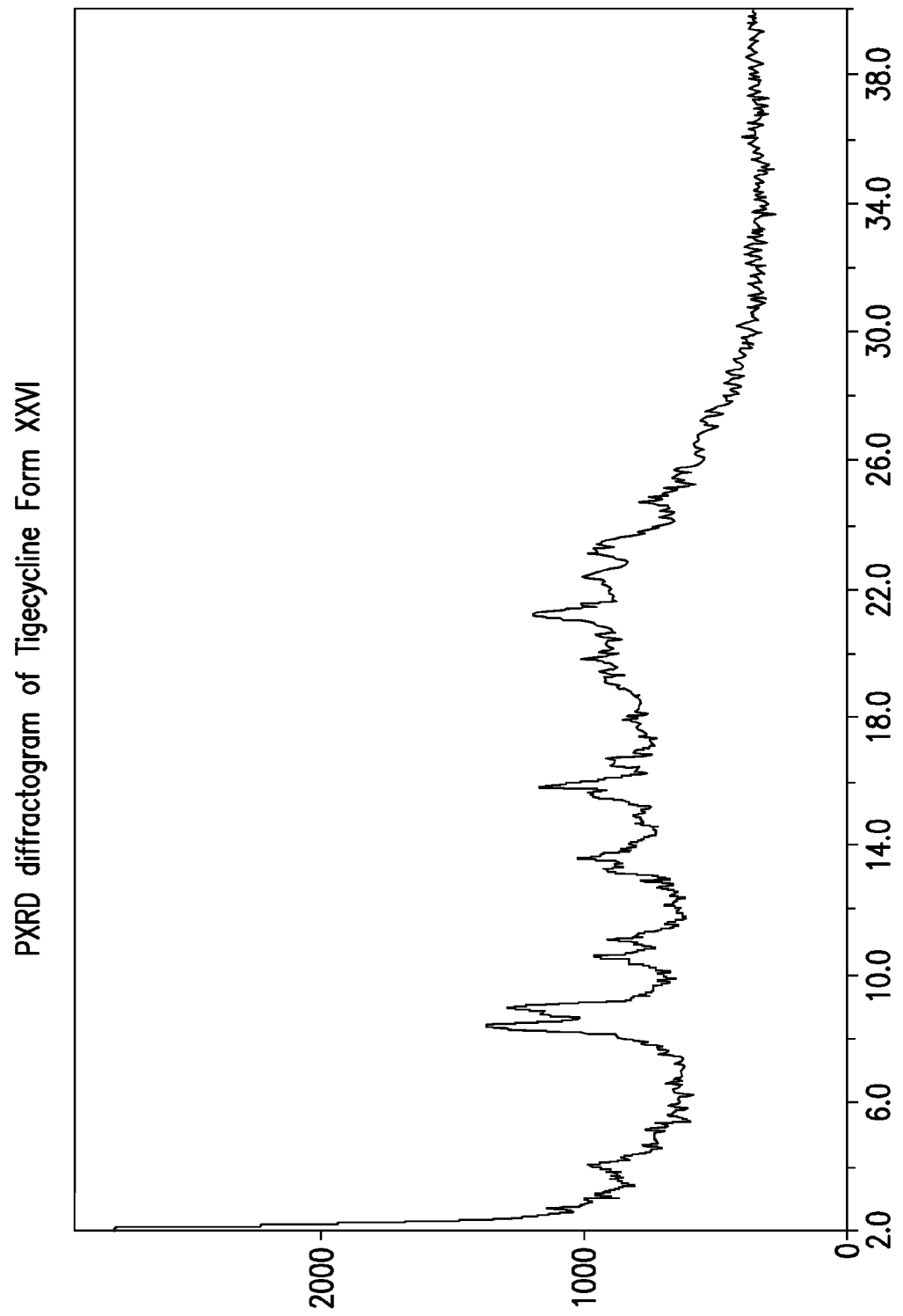
FIG. 22 illustrates a powder X-ray diffraction pattern for Tigecycline Form XXVI (as prepared by example 22).

In another embodiment, the present invention provides a crystalline form of Tigecycline, designated Form XXVI, characterized by data selected from the group consisting of a powder XRD pattern with peaks at about 6.0, 7.0, 9.1 and 10.1±0.2 degrees two-theta; and a powder XRD pattern substantially as depicted in FIG. 22. Form XXVI may be further characterized by powder XRD pattern with one or more peaks selected from the group consisting of about 4.6 and 12.1±0.2 degrees two-theta. Tigecycline Form XXVI is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XXVI may be prepared by a process comprising providing a solution of Tigecycline in dichloromethane (DCM); evaporating the solution till saturation; adding the saturated solution of Tigecycline in DCM to cold heptane, preferably dropwise; and stirring the resulting suspension for about 1 to about 5 days, preferably about 2 days, at a temperature of about −5° C. to about 110° C., preferably of about 0° C. to about 5° C. Form XXVI may be prepared by a process similar to the one described in example 23.

Figure 23:
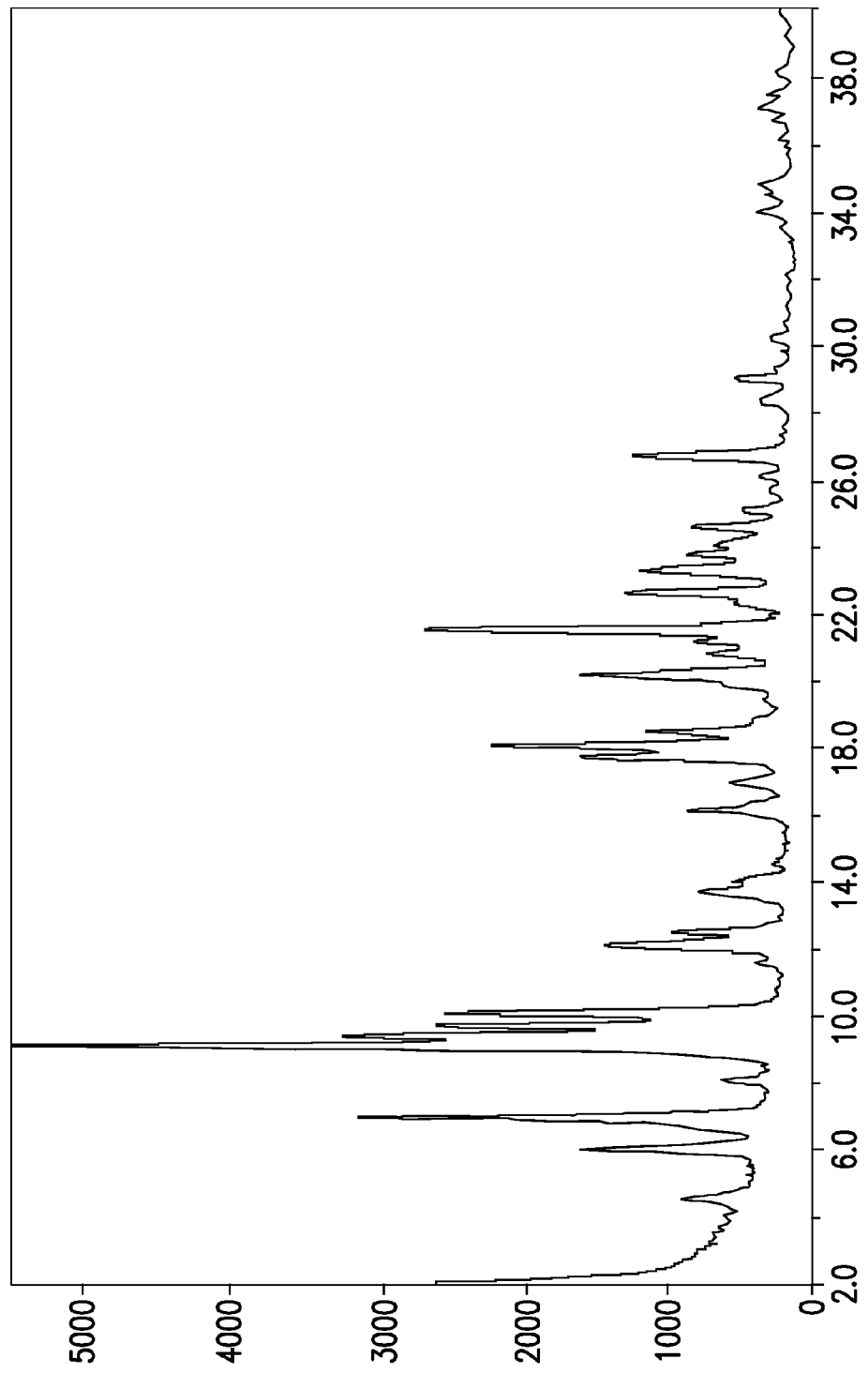
FIG. 23 illustrates a powder X-ray diffraction pattern for Tigecycline Form XXVII (as prepared by example 23).

In another embodiment, the present invention provides a crystalline form of Tigecycline, designated Form XXVII, characterized by data selected from the group consisting of a powder XRD pattern with peaks at about 8.3, 8.9, 10.6, 13.6 and 15.8±0.2 degrees two-theta; and a powder XRD pattern substantially as depicted in FIG. 23. Form XXVII may be further characterized by powder XRD pattern with one or more peaks selected from the group consisting of about 4.0 and 11.0±0.2 degrees two-theta. Form XXVII is typically yellow in color, having a G:R ratio of less than 1.8, preferably less than 1.4 and most preferably less than 1.3. Tigecycline Form XXVII is preferably in pure form having less than 10%, more preferably less than 5% and most preferably less than 1% of the crystalline form selected from the list consisting of: Forms I, II, III, IV and V as described in WO 2006/128150, which reference is incorporated herein by reference.

In another embodiment, Tigecycline form XXVII may be prepared by a process comprising providing a solution of Tigecycline in dichloromethane (DCM); adding ethylacetate; concentrating the resulting mixture to a concentration of about 5 to about 40 mL/g of product, preferably 10-20 ml/g of the product; adding ethylacetate to the concentrate to obtain a suspension; concentrating the suspension and cooling the suspension for about 15 minutes to about 2 hours, preferably 30 minutes, at a temperature of about −5° C. to about 10° C., preferably to about 0-5° C. to obtain wet form I; suspending the Form I in about 10 to about 15 ml/g of acetonitrile at 20-25° C. overnight, affording form XXVII. Form XXVII may be prepared by a process similar to the one described in example 24.

In another embodiment of the present invention, the present invention provides a pharmaceutical formulation comprising any one or more of the crystalline Tigecycline forms described above, such as Forms VI, VIII, IX, X, XI, XII, XIII, XVIII, XIX, XX, XXII, XXIII, XXIV, XXV, XXVI and XXVII. This pharmaceutical composition may additionally comprise at least one pharmaceutically acceptable excipient.

In another embodiment, the present invention provides a pharmaceutical composition comprising any one or more of the crystalline Tigecycline described above, such as Forms III, VI, VII, VIII, IX, X, XI, XII, XIII, XV, XVII, XVIII, XIX, XX, XXI, XXII, XXIII, XXIV, XXV, XXVI, and XXVII and amorphous made by the processes of the present invention, and one or more pharmaceutically acceptable excipients.

The present invention further encompasses a process for preparing a pharmaceutical formulation comprising combining one or more crystalline Tigecycline selected from the list consisting of Forms VI, VIII, IX, X, XI, XII, XIII, XVIII, XIX, XX, XXII, XXIII, XXIV, XXV, XXVI and XXVII with at least one pharmaceutically acceptable excipient.

The present invention further encompasses the use of a crystalline Tigecycline selected from the list consisting of Forms VI, VIII, IX, X, XI, XII, XIII, XVIII, XIX, XX, XXII, XXIII, XXIV, XXV, XXVI and XXVII of the present invention, for the manufacture of a pharmaceutical composition.

Pharmaceutical formulations of the present invention contain crystalline Tigecycline, such as a form disclosed herein. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Tigecycline is suspended such as to retain its crystalline form and any other solid excipients may be either dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

The present invention also provides methods comprising administering a pharmaceutical formulation of Tigecycline. Tigecycline is preferably formulated for administration to a mammal, preferably a human, by injection. Tigecycline can be formulated, for example, as a viscous liquid suspension, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., *Pharmaceutical Dosage Forms and Drug Delivery Systems,* 7th ed.

Having described the invention, the invention is further illustrated by the following non-limiting examples. Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Polymorphism in Pharmaceutical Solids, Drugs and the Pharmaceutical Sciences, Volume 95 can be used for guidance. All references mentioned herein are incorporated in their entirety.

EXAMPLES

Experimental

X-Ray powder diffraction data were obtained by using methods known in the art, using a SCINTAG powder X-Ray diffractometer model X'TRA equipped with a solid-state detector. A Copper radiation of 1.5418 Å was used. A round aluminum sample holder with zero background was used. The scanning parameters included: range: 20 to 40° 2θ; scan mode: continuous scan; step size: 0.05°. The rate for Form XX [FIG. 16] was 3°/min using spin mode while the remaining crystalline forms were 5°/min using spin mode. All peak positions are within ±0.2 degrees two theta.

Example 1

Preparation of Tigecycline Form III

A Tigecycline solution in dichloromethane was dried over sodium sulfate until obtaining a precipitate and filtered. The filtrate was evaporated to dryness and the residual solid was dried under vacuum at 40° C., overnight (10-12 h). Tigecycline thus prepared was identified as the solid state form of this invention, i.e. Form III.

Example 2

Preparation of Tigecycline Forms III, VII, IX, and X

A suspension of Tigecycline was prepared by mixing a solid Tigecycline sample and a solvent as listed in Table 1 and in amounts that correspond to the ratios listed in Table 1. The mixture was then stirred under the conditions specified in the same table. Filtration of the suspension and air-drying of the cake afforded so-called wet material. In certain experiments (indicated in the said table) the wet material was further dried overnight at 40° C. under vacuum and the solid thus obtained was referred to as the dry one.

TABLE 1

Results of the experiments according to Example 2

| | Solvent | V(mL)/gr | Temp. | Time | Product | Form |
|---|---|---|---|---|---|---|
| A | n-heptane | 20 | RT | o/n | Wet | III |
| B | n-hexane | 20 | RT | o/n | Dry | III |
| C | | | | | Wet | III |
| D | cyclohexane | 20 | RT | o/n | Dry | III |
| E | | | | | Wet | III |
| F | diisopropyl ether | 20 | RT | o/n | Dry | III |
| G | | | | | | Wet | III |
| H | MEK | 20 | RT | o/n | Dry | III |
| I | | | | | Wet | X |
| J | acetone | 20 | 0-5° C. | 20 min | Wet | IX |
| K | | | | | Dry | IX |
| L | acetone | 10 | RT then 0-5° C. | 2 h | Dry | IX |
| M | acetone | | 0-5° C. | 2 h | Wet | IX |
| P | acetone | 10 | RT then 50° C. | Total | Wet | IX |
| Q | acetone | | then RT | 1.5-2.0 h | Dry | IX |
| N | IPA | 40 | RT | 1.5 h | Dry | III |
| O | MeOH | 40 | RT | 1 h | Dry | VII | o/n = overnight

Example 3

Preparation of Tigecycline Form VI

A solid Tigecycline sample was dissolved in THF whereupon n-heptane was added into the resulted solution so that precipitation took place. The suspension formed was stirred for an hour at ambient temperature and then filtered. The solid thus obtained was dried overnight at 40° C. under vacuum to afford Form VI of Tigecycline from THF.

Example 4

Preparation of Tigecycline Form VIII

Tigecycline solution in dichloromethane was dried over sodium sulfate to obtain a reduced volume. The residual concentrate was treated with n-heptane so that precipitation occurred. The resulted suspension was filtered and the solid air-dried on the Buchner funnel. Tigecycline thus obtained was identified a new Form VIII.

Example 5

Preparation of Tigecycline Form VIII

A solution of Tigecycline in dichloromethane provided and dried over sodium sulfate. The solvent was than partially evaporated to about 1/15 of the original volume and EtOAc was added to the residual mixture so that the final total volume of the suspension thus formed is about 1/5 of that of the original dichloromethane solution. About 1/3 of the resulted suspension was then evaporated and the residual slurry was stirred at 0-5° C. for about an hour, whereupon it was filtered. The solid thus obtained was air-dried, analyzed and identified as Form VIII of Tigecycline.

Example 6

Preparation of Tigecycline Form XI

Tigecycline sample was combined with 20 volumes of 2-methyltetrahydrofurane and the mixture was stirred at ambient temperature overnight. The resulted suspension was filtered and the filter cake air-dried to afford Tigecycline of Form XI. The sizes of the Tigecycline Form XI crystals were less than 300 µm.

Example 7

Preparation of Tigecycline Form XII

Tigecycline sample was dissolved in 20 volumes of hot iso-propanol. The solution thus obtained was allowed to cool at ambient temperature and then further cooled at 0-5° C. for about half an hour. The resulted suspension was filtered and the solid air-dried on the filter to afford Tigecycline of Form XII. The material was further dried overnight at 40° C. under vacuum without affecting the polymorphs, i.e. the vacuum dried Tigecycline was still identified as Form XII. The sizes of the Tigecycline Form XII crystals were less than 300 µm.

Example 8

Preparation of Tigecycline Form XIII

Tigecycline sample was dissolved in 20 volumes of n-propanol or 40 volumes of hot ethanol. The solution thus obtained was allowed to cool at ambient temperature and then further cooled at 0-5° C. for about half an hour. The resulted suspension was filtered and the solid air-dried on the filter to afford Tigecycline Form XIII. The material was further dried overnight under vacuum at 40° C. without affecting the polymorphs, i.e. the vacuum dried Tigecycline was still identified as Form XIII. The sizes of the Tigecycline Form XIII crystals were less than 300 µm.

Example 9

Preparation of Tigecycline Form XV

Tigecycline, prepared by U.S. Pat. No. 5,675,030, was placed in a beaker that was then kept under acetonitrile atmosphere in a tightly closed container. The solid was analyzed after 7 days and identified as Tigecycline of Form XV.

Example 10

Preparation of Tigecycline Form XV

Tigecycline, prepared by U.S. Pat. No. 5,675,030, was mixed with 20 volumes of cold acetonitrile and the resulted mixture was stirred upon cooling on ice-water batch. After an hour the suspension was filtered and the air-dried solid was analyzed. Eventually, XRD pattern of the solid indicated the new form XV of Tigecycline.

Example 11

Preparation of Tigecycline Form XVII 2 grams of Tigecycline was dissolved in 440 mL of DDW and pH of the mixture was adjusted at 7.38 and 60 mL of THF were then added. The resulted solution was extracted 6 times with 60 mL portions of dichloromethane while pH is carefully controlled at 7.2-7.4. The combined organic extract was then dried over sodium sulfate and concentrated to about 10 mL to afford a suspension of Tigecycline. The solid was filtered and washed with heptane. Analysis of the material indicated Form XVII Tigecycline. After drying under vacuum, the material indicated Form XVII Tigecycline as displayed in FIG. 16.

Example 12

Preparation of Tigecycline Form XVIII 2 grams of Tigecycline was dissolved in 440 mL of DDW and pH of the mixture was adjusted at 7.33 and 60 mL of THF were then added. The resulted solution was extracted 6 times with 60 mL portions of dichloromethane while the pH is carefully controlled at 7.2-7.4. The combined organic extract was then dried over sodium sulfate, filtered and the solid was washed with 50 mL of dichloromethane into the initial filtrate. The combined filtrate was concentrated to 30-40 mL and the concentrated was stirred for about half an hour at 0-5° C. A precipitation occurred upon the cooling and the solid was collected and vacuum dried. Analysis of the material before and after the drying indicated Form XVIII of Tigecycline in both cases. FIG. 17 shows PXRD diffractogram before drying.

Example 13

Preparation of Tigecycline Form XIX

A solution of Tigecycline in dichloromethane was provided between 5 and 10 g/L, and dried over sodium sulfate. Toluene was added to the solution so that the total volume increased to about 1.15 of the original volume. The resulted solution was then partially evaporated so that the volume of the residual mixture was similar to that of the toluene added. The resulted suspension was filtered and the solid thus obtained was dried under vacuum. Analysis of the material before and after the drying indicated Form XIX of Tigecycline in both cases. FIG. 15 shows the PXRD diffractogram after drying.

Example 14

Preparation of Tigecycline Forms VIII and XX

A solution of Tigecycline in dichloromethane was provided and dried over sodium sulfate. Di-n-butyl ether was added to the solution so that the total volume increased to about 1.15 of the original volume. The resulting solution was then partially evaporated so that the volume of the residual mixture was similar to that of the di-n-butyl ether added. The resulted suspension was filtered and the cake washed with di-n-butyl ether. Tigecycline thus obtained was identified as Form VIII in both wet and vacuum dried samples.

Combined filtrates from the above filtration ware stirred overnight at ambient temperature and filtered. The second crop of Tigecycline thus obtained was identified as Form XX. PXRD diffractogram is shown in FIG. 16.

Example 15

Preparation of Tigecycline Form XXI

A solution of Tigecycline in dichloromethane was provided and dried over sodium sulfate. Acetonitrile was added to the solution so that the total volume increased to about 1.15 of the original volume. The resulted solution was then partially evaporated so that the volume of the residual mixture was similar to that of the acetonitrile added. The same as above amount of acetonitrile was added to the residual suspension and the mixture thus obtained was concentrated to about a half of its initial volume. This operation was repeated one more time and the resulted suspension was stirred at 0-5° C. for about 1 hour. Filtration of the cold suspension afforded a wet solid that was identified as Form XXI of Tigecycline, as shown in FIG. 17.

Example 16

Preparation of Tigecycline Form XXI

A solution contained about 10 gr Tigecycline in about 700 ml dichloromethane was provided, dried over sodium sulfate and filtered, whereupon 100 ml of ethyl acetate were added to the filtrate. The resulted mixture was concentrated to about 50 ml and 220 ml of fresh ethyl acetate were added to the concentrate. The suspension thus obtained was concentrated to about 50 ml, cooled at 0-5° C. for about half an hour and filtered. The solid was washed with 15 ml of ethyl acetate and defined as wet Tigecycline form-I. The wet material was kept at 0-5° C. during 14-60 hours and finally dried under vacuum at 60° C., overnight thus affording Form XXI of Tigecycline.

Example 17

Preparation of Tigecycline Form XXII 200 mg of Tigecycline Form IX was placed into a container and stored for 7 days under 100% RH at room temperature.

After storage, the sample was analyzed by XRD and found to be Form XXII, as shown in FIG. 18.

Example 18

Preparation of Tigecycline Form XXIII 200 mg of Tigecycline Form VII was placed into a container and stored for 7 days under 0% RH at room temperature. After storage, the sample was analyzed by XRD and found to be Form XXIII, as shown in FIG. 19.

Example 19

Preparation of Tigecycline Form XXIV

Tigecycline solution in dichloromethane was prepared by reacting 10 gr of 9-haloacetamidominocycline with an excess of t-butyl amine, diluting the reaction mixture with water, purifying the aqueous solution and extracting the product with the said organic solvent (7×100 mL). The organic solution thus obtained was dried over sodium sulfate and filtered, whereupon 100 mL of EtOAc were added to the filtrate. The resulted mixture was concentrated to about 50 mL and 220 mL of fresh EtOAc were added to the concentrate. The suspension thus obtained was concentrated to about 50 mL, cooled at 0-5° C. for about half an hour and filtered. The solid was washed with 15 mL of EtOAc and dried under vacuum at 60° C., overnight thus affording Form XXIV of Tigecycline, as shown in FIG. 20.

Example 20

Preparation of Amorphous Tigecycline Via Slurry

Tigecycline, was prepared according to U.S. Pat. No. 5,675,030, in methyl acetate, overnight, at ambient temperature. The mixture was then filtered and the cake air-dried on the funnel thus affording a solid, which was identified as amorphous Tigecycline by means of XRD measurement. This material was further dried overnight at about 40° C. under vacuum and reanalyzed. XRD pattern of the dry solid still corresponded to the amorphous material.

Example 21

Preparation of Amorphous Tigecycline Via Precipitation

A solid Tigecycline sample was completely dissolved in methyl iso-butyl ketone whereupon n-heptane was added into the resulted solution so that precipitation took place. The suspension formed was stirred for an hour at ambient temperature and then filtered. The solid thus obtained was dried overnight at 40° C. under vacuum to afford amorphous (by XRD) Tigecycline.

Example 22

Preparation of Tigecycline Form XXV

Form I prepared from ethyl acetate (about 80 mg) as described in U.S. Application Ser. No. 60/796,800 was exposed to either 0% or 100% relative humidity for 7 days at room temperature. After the exposure the crystal form was monitored by XRD.

| % RH | Crystal form |
|---|---|
| 0 | New form XXV |
| 100 | Amorphous |

Example 23

Preparation of Tigecycline Form XXVI

Tigecycline solution in dichloromethane was prepared by reacting 30 g of 9-haloacetamidominocycline with an excess of t-butyl amine, diluting the reaction mixture with water, purifying the aqueous solution and extracting the product with the said organic solvent (7×300 mL). The obtained solution was saturated by evaporation.

320 mL saturated solution (about ⅓ of the total solution) of Tigecycline in dichloromethane was added dropwise to 80 mL cold Heptane for 1.5 h and the resulting suspension was stirred over 2 h at 0-5° C., whereupon it was filtered. The cake thus obtained was dried for 3 days in vacuum at 60° C. and identified as Form XXVI of Tigecycline.

Example 24

Preparation of Tigecycline Form XXVII

Tigecycline solution in dichloromethane was prepared by reacting 33.3 g of 9-haloacetamidominocycline with an excess of t-butyl amine, diluting the reaction mixture with water, purifying the aqueous solution and extracting the product with the said organic solvent (7×330 mL).

165 mL of EtOAc were added to 1 L of aforesaid solution. The resulted mixture was concentrated to about 80 mL and 330 mL of fresh EtOAc were added to the concentrate. The suspension thus obtained was concentrated again to about 80 mL, cooled at 0-5° C. for about half an hour and filtered. The orange solid material thus obtained was mixed with 140 mL of acetonitrile at 20-25° C. overnight, whereupon a yellow solid formed, having a G:R ratio of less than 1.3. This solid was filtered and air-dried to afford Form XXVII of Tigecycline.

Example 25

Polymorphic Transition Due to Heating in Oven

Tigecycline Form I was placed in oven at a temperature of between about 120-150° C. for about 0.5-1 hr (for example: 140° C. for 1 hr) The resulting solid was analyzed by XRD and showed Tigecycline amorphous form.

Tigecycline Form X was placed in oven at a temperature of between about 50-150° C. for about 0.5-2 hr (for example: 60 for 2 hr, 140° C. for 1 hr). The resulting solid was analyzed by XRD and showed Tigecycline amorphous form.

Tigecycline Form XI was placed in oven at a temperature of between about 50-80° C. for about 1-2 hr (for example: 60 for 2 hr). The resulting solid was analyzed by XRD and showed Tigecycline mixture of Form XI and Form VI.

Tigecycline Form XI was exposed to 0% relative humidity (RH) for 7 days at room temperature. The resulting solid was analyzed by XRD and showed Tigecycline mixture of Form XI and Form VI.

Tigecycline Form XVII was placed in oven at a temperature of between about 50-70° C. for about 1-2 hr (for example:

60 for 2 hr). The resulting solid was analyzed by XRD and showed Tigecycline mixture of Form XVII and Form VI.

Tigecycline Form XVII was placed in oven at a temperature of between about 90-110° C. for about 0.5-1 hr (for example: 100 for 0.5 hr). The resulting solid was analyzed by XRD and showed Tigecycline Form VI.

Tigecycline Form XVIII was placed in oven at a temperature of between about 120-150° C. for about 0.5-1 hr (for example: 140 for 1 hr). The resulting solid was analyzed by XRD and showed Tigecycline amorphous form.

Tigecycline Form XXIV was placed in oven at a temperature of between about 110-140° C. for about 0.5-1 hr (for example: 120 for 0.5 hr, 140° C. for 1 hr). The resulting solid was analyzed by XRD and showed Tigecycline amorphous form.

Tigecycline Form XI was pressed by a laboratory press by pressure of about 1-2 tons for about 1-3 min (for example: 2 tons for 1 min). The resulting solid was analyzed by XRD and showed Tigecycline mixture of Form XI and Form VI.

Tigecycline Form XVII was pressed by a laboratory press by pressure of about 1-2 tons for about 1-3 min (for example: 2 tons for 1 min). The resulting solid was analyzed by XRD and showed Tigecycline mixture of Form XVII and Form VI.

Tigecycline Form XVII was strongly ground by mortal and pestle for about 0.5-1 min. The resulting solid was analyzed by XRD and showed Tigecycline mixture of Form XVII and Form VI.

We claim:

1. A crystalline form of Tigecycline, designated Form IX, characterized by data selected from the group consisting of a powder XRD pattern with peaks at 5.2, 9.3, 13.1, 13.8, 16.5, 18.8, 20.6 and 22.1±0.2 degrees two-theta; a powder XRD pattern as depicted in FIG. 7; a solid-state $^{13}$C NMR spectrum with signals at 204.4, 192.8, 177.2, 174.7, and 169.5±0.2 ppm; a solid-state $^{13}$C NMR spectrum having chemical shift differences between the signal exhibiting the lowest chemical shift and another in the chemical shift range of 90 to 210 ppm of 108.6, 97.0, 81.4, 78.9, and 73.7±0.1 ppm; a solid-state $^{13}$C NMR spectrum depicted in FIG. 32; and a solid-state $^{13}$C NMR spectrum depicted in FIG. 33, wherein the signal in the solid-state $^{13}$C NMR exhibiting the lowest chemical shift in the chemical shift range of 90 to 210 ppm is at 95.8±1 ppm.

2. The crystalline form of Tigecycline of claim 1, wherein the crystalline form is an acetone solvate.

3. The crystalline form of Tigecyline of claim 1, wherein the crystalline form has a weight loss, as measured by TGA, of between 6.5-9.0% by weight.

4. The crystalline form of Tigecycline of claim 1, wherein the crystalline form has water content, as measured by KF, of between 1.0-1.5% by weight.

5. The Tigecycline as in claim 1, having less than 10% of Forms I, II, III, IV and V.

6. The Tigecycline as in claim 5, having less than 5% of Forms I, II, III, IV and V.

7. The Tigecycline as in claim 6, having less than 1% of Forms I, II, III, IV and V.

8. A pharmaceutical formulation comprising crystalline Tigecycline Form IX according to claim 1 and at least one pharmaceutically acceptable excipient.

9. A process for preparing a pharmaceutical formulation comprising combining crystalline Tigecycline Form IX according to claim 1 with at least one pharmaceutically acceptable excipient.

10. A process for the preparation of the crystalline Tigecycline Form IX according to claim 1 comprising: providing a mixture of Tigecycline Form I and a solvent selected from acetone, isopropanol and mixtures thereof; and maintaining the mixture for at least 20 minutes to obtain Form IX.

11. The process of claim 10, wherein the mixture is maintained for about 20 minutes to about 72 hours.

12. The process of claim 10, wherein when isopropanol is used, the process further comprises recovery including a drying step for about 10 to about 16 hours at 20° C. to about 60° C. under vacuum.

* * * * *